United States Patent
Lee et al.

(10) Patent No.: US 6,406,841 B1
(45) Date of Patent: Jun. 18, 2002

(54) METHODS FOR THE DETECTION OF HTLV-II ANTIBODIES EMPLOYING NOVEL HTLV-II NRA ENVELOPE PEPTIDES

(75) Inventors: Helen H. Lee, Lake Forest; Priscilla A. Swanson, Libertyville, both of IL (US); Kenneth B. Idler, Trevor, WI (US); Joseph D. Rosenblatt, Los Angeles; Irvin S. Y. Chen, Woodland Hills, both of CA (US); David W. Golde, New York, NY (US); Eugene Robertson, Grayslake, IL (US); John E. Stephens, Gurnee, IL (US); Emerson W. Chan, Libertyville, IL (US); Mark H. Buytendorp, Cary, IL (US); Joan E. Johnson, Libertyville, IL (US); Cheryl T. Motley, Waukegan, IL (US); Michelle Edwards, Kenosha, WI (US); Cynthia Tate, Chicago, IL (US); Bryan Peterson, Mundelein, IL (US); Peggy Guidinger, Chicago, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 08/259,451

(22) Filed: Jun. 20, 1994

Related U.S. Application Data

(63) Continuation-in-part of application No. 08/086,415, filed on Jul. 1, 1993, now abandoned.

(51) Int. Cl.[7] .................................................. C12Q 1/70

(52) U.S. Cl. ....................... 435/5; 435/7.1; 424/187.1; 424/207.1; 422/61

(58) Field of Search ...................... 435/4, 5, 2.1, 295.1; 530/350; 424/184.1, 187.1, 207.1, 204.1

(56) References Cited

U.S. PATENT DOCUMENTS

| 4,228,237 A | 10/1980 | Hevey et al. |
| 4,438,032 A | 3/1984 | Golde et al. |
| 4,683,195 A | 7/1987 | Mullis et al. |
| 4,683,202 A | 7/1987 | Mullis |
| 5,039,604 A | 8/1991 | Papsidero et al. |
| 5,041,385 A | 8/1991 | Kingsman et al. |
| 5,378,805 A * | 1/1995 | Lal ............................ 530/326 |

FOREIGN PATENT DOCUMENTS

| EP | A320308 | 6/1989 |
| EP | A336731 | 10/1989 |
| WO | 8601834 | 3/1986 |
| WO | 8909835 | 10/1989 |

(List continued on next page.)

OTHER PUBLICATIONS

Harlow et al., 1988, Antibodies: A Laboratory Manual. Cold Spring Harbor Laboratory, p. 179.*
Cockerell et al., 1991, Infectious Transmission of Human T–Cell Lymphotropic Virus Type II in Rabbits, Blood, 78(6):1532–1537.*

(List continued on next page.)

*Primary Examiner*—Laurie Scheiner
*Assistant Examiner*—Jeffrey S. Parkin
(74) *Attorney, Agent, or Firm*—Andreas M. Danckers; Dianne Casuto

(57) ABSTRACT

The present invention relates generally to a novel human T-cell lymphotropic, or leukemia, virus type II (HTLV-II) isolate designated NRA. HTLV-II$_{NRA}$ was originally isolated from a patient with atypical hairy cell leukemia. Preliminary restriction analysis of this isolate demonstrated that it differs genetically from the prototypical HTLV-II isolate Mo. HTLV-II$_{NRA}$ proviral molecular clones were obtained and the entire nucleotide sequence of the virus ascertained. The claimed invention is particularly directed toward the gp46 and p21e envelope proteins encoded by the env gene. Methods and kits for the detection of HTLV-II antibodies employing these envelope proteins are also described.

23 Claims, 8 Drawing Sheets-

HTLV-II NRA ISOLATE GENOMIC SEQUENCE DIAGRAM

FOREIGN PATENT DOCUMENTS

| | | |
|---|---|---|
| WO | 8912696 | 12/1989 |
| WO | 9010231 | 9/1990 |
| WO | 9015820 | 12/1990 |
| WO | 9204046 | 3/1992 |
| WO | 9301316 | 1/1993 |

OTHER PUBLICATIONS

Harlow, E. and D. Lane, 1988, "Immunoblotting", in Antibodies: A Laboratory Manual, Harlow, E. and D. Lane, eds., Cold Spring Harbor Laboratory, pp. 496 and 497.*
Barker et al., *Plant Mol. Bio.*, 2:335–350 (1983).
Berger et al., *Neurology*, 41:85–87 (1991).
Berneman et al., *Proc. Natl. Acad. Sci.*, 89:3005–3009 (1992).
Chen et al., *Nature*, 305:502–505 (1983).
Chen et al., *Proc. Natl. Acad. Sci.*, 80:7006–7009 (1983).
Ciminale et al., *J. Virology*, 66:1737–1745 (1992).
Daenke et al., *J. Virology*, 64:1278–1282 (1990).
De et al., *Virology*, 182:413–419 (1991).
Devereux et al., *Nucelic Acids Res.*, 12:387–395 (1984).
Dube et al., *J. Virol.*, 67:1175–1184 (1993).
Ehrlich et al., *Blood*,74:1658–1664 (1989).
Gessain et al., *Lancet*, II:407–409 (1985).
Gessain et al., *J. Virol.*, 66:2288–2295 (1992).
Goodenow et al., *J. Acquired Immune Defic. Syndr.*, 2:344–352 (1989).
Gray et al., *Virology*, 177:391–395 (1990).
P.L. Green et al., "Regulation of human T cell leukemia virus expression" FASEB Journal, vol. 4, pp. 169–179, Feb. 1990.
P.L. Green et al., "The Internal Methionine Codons of Human T–Cell Leukemia Virus Type II rex Gene Are Not Required for $p24^{rex}$ Production or Virus Replication and Transformation" Journal of Virology, vol. 64, No. 10, pp. 4914–4921, Oct. 1990.
Hall et al., *J. Virol.*, 66:2456–2463 (1992).
Hjelle et al., *Lancet*, 339:645–646 (1992).
Hjelle et al., *Blood*, 76:450–454 (1990).
Kalyanaraman et al., *Science*, 218:571–573 (1982).
Kinoshita et al., *Int. J. Cancer*, 47:491–495 (1991).
T. Kiyokawa et al., "Envelope proteins of human T–cell leukemia virus: Expression *Escherichia coli* and its application to studies of env gene functions" Prod. Nat'l. Acad. Sci. USA, vol. 81, pp. 6202–6206, Oct. 1984.
Komurian et al., *J. Virol.*, 65:3770–3778 (1991).
M. D. Lairmore et al., "Isolation of human T–cell lymphotripic virus type 2 from Guaymi Indians in Panama" Prod. Nat'l. Acad. Sci. USA, vol. 87, p.p. 8840–8844, Nov. 1990.
Lal et al., *J. Infectious Diseases*, 163:41–46 (Jan. 1991).
Lee et al., *Lancet*, 337:1435–1439 (1991).
Lee et al., *Science*, 244: 471–475 (1989).
H. Lee et al., "Complete Nucleotide Sequence of HTLV–II Isolated NRA: Comparison of Envelope Sequence Variation . . . " Virology 196, 57–69 (1993).
Maniatis et al., *Molecular Cloning, A Laboratory Manual*, Cold Spring Harbor (1982).
Needleman et al., *J. Mol. Biol.*, 48:443–453 (1970).
Paine et al., *Virology*, 182:111–123 (1991).
D. Pardi et al., "Complete Nucleotide Sequence of an Amerindian Human T–Cell Lymphotropic Virus Type II (HTLV–II) Isolate: Identification of a Variant . . . " Journal of Virology, vol. 67, No. 8, Aug. 1993, p.p. 4659–4664.
Poiesz et al., *Proc. Natl. Acad. Sci. USA*, 77:7415–7419 (1980).
Ratner et al., *AIDS Res. and Human Retroviruses*, 7:923–941 (1991).
Robert–Guroff et al., *JAMA*, 255:3133–3137 (1986).
Rosenblatt et al., *AIDS*, 6:1151–1158 (1992).
Rosenblatt et al., *New Engl. J. Med.*, 315:372–377 (1986).
Rosenblatt et al., *Blood*, 71:363–369 (1988).
Ruben et al., *Neu. Biol.*, 1:275 (1989).
Sambrook et al., *Molecular Cloning, A Laboratory Manual*, Second Edition, Cold Spring Harbor Laboratory Press, 4.39–4.43 (1989).
Sanger et al., *Proc. Natl. Acad. Sci. USA*, 74:5463–5467 (1977).
Saxon et al., *Ann. Intern. Med.*, 88:323–326 (1978).
Seiki et al., *Proc. Natl. Acad. Sci*. 80:3618–3622 (1983).
Sherman et al., *J. Virol*, 66:2556–2563 (1992).
Shimotohno et al., *Proc. Natl. Acad. Sci. USA*, 82:3101–3105 (1985).
Southern, *J. Mol. Biol.*, 98:503–517 (1975).
Starcich et al., *Cell*, 45:637–648 (1986).
Tedder et al., *Lancet*, 11:125–128 (1984).
Towbin et al., *Proc. Natl. Acad. Sci.*, 76:4350–4354 (1979).
Tsujimoto et al., *Mol. Biol. Med.*, 5:29–42 (1988).
Uchiyama et al., *Blood*, 50:481–492 (1977).
Vogt, Jr. et al., "Quantitative differences among various proteins as blocking agents for ELISA microtiter plates" Journal of Immunological Methods, 101 (1987) 43–50.
Yanagihara et al., *Proc. Natl. Acad. Sci.*, 88:1446–1450 (1991).
Zella et al., *Lancet*, 336:575–576 (1990).

* cited by examiner

HTLV-II NRA ISOLATE GENOMIC SEQUENCE DIAGRAM

Start 5' LTR

| | |
|---|---|
| TGACAATGGCGACcAGCCCTCCtg*AGCCAGCCgCCCAGGGGCGAGTCATGACCCGAGTCATGACCCAAAAGGTCAGACCGTCTCACACAAACAATCCCAAGTAAAGGCTCTGA | 100 |
| CGTCTCCCCC..TTTaTAGGAACTGAAACCAaGGCCCTGACGTCC...CCCCCagGaAcCAGGAAaGAGCTCTCAG..AAAAATAaACCTCgCCCTTACCCACTTC | 200 |
| CCTAGCaCTGAAAAACAAGGCTCTGACCATTACCCCCCCTGCCCTAGCCAAAAATAAAgGATGCCCAGTCTATAAAAGCCCAAGGACA | 300 |
| BamHI | |
| GTTCAGGAGGTCtCTCGCTCCttCACCGACCCTCCGGTCgGGaGACTCACTTGGGATCCATCCTCTCCAAGCGGCCTCCGTcGAGACCCTTCCGTG | 400 |
| GGACtGTCTCCCGGCCTCCaGCACCTCCTGAACTGCTCCTtCCAgGTAAGCTCTCCTCCAGGTCGAGCTtGGCTGCCtCTTAGGTAGTCGCTCCCGAGG | 500 |
| GTCTTAGAGACACACCCGGGTTcCGGCTACGCTCGGCTAGACTCTGgCTTGAAACcTCACTTCCCGGTTCTTGGTCTCGTTCTTTCCTCTTCGtCGTCAC | 600 |
| TGAAACGAAACtTCAACGCCCGCCCTtcTGGCAGGCTTGgCCGAGGGCCCAgCATACTGcCgcgGagGCCGCAgTAAGGGCTAGGGCTTCCTGAACCTCTCC | 700 |
| End 5' LTR | |
| GGGACAGGTCcATcGCTATAGGCAGGCCCGCCCcAGGAGCATCGTCTTCCCGGGAAGACAAACAAgTGGGGGCTCGTCCGGGATcTGAATTCCTCCAT | 800 |
| | |
| TCTCACATTATGGGgCAAATCCACGGGCTTTCCCCAACTCCAGTACCCAAgGCCCCCAGGGCTATCgACCCCAGGGCTGGCTTAATTTTCTCCAGGCTG | 900 |
| Start GAG | |
| CTTACCGCcTGCAGCCTgGCGCCTCCGATTTCGACTTCCACaCAGCTACGACGCTTCTtAAACTgCCCCTTAAAACCCCATTGGCTAAATCCTATcGA | 1000 |
| CTACTCGCTTTAGCTAGCCTTATCCCAAgGGATATCCgGAAGGGCTGGTAGAGATTATAAACATCCTTGTCAAAAACAAGTCTCCCCTTACGGCCCCC | 1100 |
| GCCCCCCAGTTCCGACACCTATCTGCCCTACCACTACCCCTCGGAGCCCCTCAGTCTCAcCAGGCCCTGGCACAGTTTGACCCCACGCCAAGGAGTCAG | 1200 |
| CtACCACGaCAATGCTTCCTATCTTACATCCCCCtGGAGCCCCTCAGCTCAcAGGGCTGGCGGTACAACTAATcACCGAGGCTGAACTGCGGgTACAGGACTTACAAGATCTCCTCCAGTAC | 1300 |
| CTCCCTGCcCcCTGGCAGCCCCCTCGtgTTTCCTTACACCATCAGCACCGCCCAcAcAAGGTCtGTTCCTTACACCATCAGCACAGCCCAcAcAAGGTCtGTACAGGCTACAACCCCATGGCAG | 1400 |
| CTATGCTCCTCCCTCGtgTTTCCTTACACCATCAGCACCGCCCAcAcAAGGTCtGTACAGGCTACAACCCCATGGCAG | 1500 |
| GGCCCCTAAGAATGCAGGCTAATAACCCCGCCAaCAAGGTCTTAGAGGGAGTACCCTAcTGCCGCGTTCGTAGAGCGCTTCAAAGATCTCCCACCCTTCCAGGCAATAC | 1600 |
| CCGTGACCCCTCTGGGCGgCTATCTACAAGGGCTACTCCCTAGGGTACTCAAATGCCAACAAGAATGCCAAAAATCTTACAGCCCGtGGACACACTAACAGCCCCC | 1700 |
| GGCaCCCCAAAGAGCCCCATATTACGcTCCCAAGGGTACTCAAATGCCAACAAGAATGCCAAAAATCTTACAGCCCGtGGACACACTAACAGCCCCC | 1800 |
| TcGGGGAGATGCTtCGgGCATGGCCAaGGTGGACACCCAAGGACCCAAAAACCAAGGTCCTTGTGTCCAACCACGAGCCCCCCACACAGCCCTGCTT | 1900 |
| End GAG | |
| TCGTGTGGCAAGaTAGGACACACTGGAGTCGGACTGcACCCAGCTGGACTGAAAAAACCCTGCCCCCTATGCCAgGATCCTTCTCTCATTGGAAAAGG | 2000 |
| GACTGCCCACAGCTtAAACCCCTCAGGAGGAAGGGGAACCCTCCGTTGGATCCTCtCCTCCACCTCAGGtCATACTGCAGGAAAAAACTCCTTAgGGG | 2100 |
| BamHI | |
| GGGAGAGATCAATCTCCCCCCCATCCCGATCAAGACATCTCaATCCCACTCATtCCCCTGCGGCAaCAACAaCAACCAATTCTAGGaGTCCGGATTCC | 2200 |
| Start Pol Precursor | |

FIG. 2A

```
GTTATGGGACAAAACCTCAGCTACCCAAGCGCTACTTGACACAGGAGCCGACCgTACGGTTATACCCCAGACACTCGTGCCtGGGCCCGTAAAGCTCC    2300
ACGACACCCTGgTCCTAGGCGCCAGTGGGCAAACtAAtACCCAGTTCAAACTCCTCAAACCCCCTACACATATTCTtaCCCTTCCGAAagTCCCCCGT    2400
```

Start POL                                                                                             Xbal

```
TATtCTTcCCTCCTGtCTCTTAGACACCCACAACAATGACCATCATTGAAGaGACGCCCTACAACAATGCCAGGGCTTCTATACCTtCCAGACGAt    2500
CCCAGCCCCCAtCAATTGCTGCCAATAGCCACTCCACACACTAGGCCTCGAACACTTCCCCCACCgCCCAgTGAACCACCTTCCTTAAACCTGA    2600
GCGCTCCAGGCCTTAAATGACCTGTCTCCAAGGCCCTGGaGGCCTGGcCACATTGAACCgTACTCAGGACCAGGCAATAACCCGTCTTCCCGTTAAA    2700
AAACCAAATGGcAAATGGAGGTTCATTCATGATGACCTTAAGAGCCACCACCAAGCCCATAGACCATACGAaCCTTACTGAGACCATAGACAAATCCCCCAAGCAGTtCAGCCATACTTCGCCTTCAC    2800
GCCTACCaACAGCCTTACCCCACCTACAGACCATAGACCTTACTGAGACCATACGAaCCTTACTGACGGCCTTTTTCCAAATCCCCTCCCAAGCAGTtCAGCCATACTTCGCCTTCAC    2900
CATTCCCCAGCCATGCTAAtTATGGCCCCGGACCAGATAcGCATGGACTGTCCTTCCACAGGGGTTTAAAAAACAGCCCACCCCTCTTCAgCAAGAATTA    3000
GCgGCTGTCCTCAACCCATGAGGGAAAAATGTTTCCCACgTCGACCATTGTCCAATACATGGATGACATACTTTTgGCCAGCCCCCACCAATaAGGAATTAC    3100
AACAACTCTCCCAGtTAACCCTCCAGGCCACTGACCACcACATGGCCTTCCAATcTCCCAGGAGAAAAAACgCAACgtACCCAGGCCAgATACGCTTCTTAGG    3200
ACAaGTCATCTCCCCTAATCACATTACAGAaGTACCCCTgCTATTCCCAATAAATCCCATATATTCTGCCCTTCAGCAGTCGACACTCACTGAgcTACAgGTTATCCTAGGAGAa    3300
AtCCAGTGGGTCTCtAAAGGtACCCCATCCTCAAAGACACCTTACAAACACTCAAGCTCTCAACAAGCATAACTGCCGtGGCCCCTCgACCCtaCCCTACCTCTCCTcGGCCTtAT    3400
TtACaCCACAACAACTCCATGCGcTACATGCAcTACAAGCTCTCAACAAGCATAACTGCCGtGGCCCCTCgACCCtaCCCCCACCCTCCGACCAGTTTATGT    3500
CTCGTtgAGTACATCTGTCATCTTTCAACCCAAGCAAAcTGGCCCCTGGCTTCCAtACCCCCACCCTCCGACCAGTTTATGT    3600

CCTTGGGGTCACCTACTGGCCTGtACCATtcTAACTCTAGACAAATAcACCCTACAACAATATGCCtGCTCTGCCAATCTTTCCACCACAACATGTCAA    3700
AaCAgSCCCTTTGCCACTTCCTaAGGAACTCCCCTCATCCAAGcGTGGGACATCCTCATTCACCACATGGGTGcTTCCATAACCTTGGCAGtCAACCGTC    3800
TGGcCCGTGGAAGACTCTTCTTACACCTCCAGAACCACCACGACTCCTCAGcCAATTTTCACCCTCTCCCCGTCGTCTGCTTGACACGGCC    3900
CCCTGCCTTTTTCCGATGGCTCCCCTCAAAAGGcGGCATAcGTCCTTGCCATATCTGTGGACCAGACTATCCTTCAACAaGACATtACTCCCCTGCCcCTCACGAAA    4000
CAaATTCCGCACAAAAGGGdGAaCTCCCTCGGCACTTCCTGCACTTATCTaTGGACTAGTGTGCTGCCAAGCCATGGCCcTCCCTTAAtATCTTcTTAGACTCTAAATAcTT    4100
AATCAAATACCTACAcTCCCTCGGCACTTCCTGCACTTATCTaTGGACTAGTGTGCTGCCAAGCCATGGCCcTCCCTTAAtATCTTcTTAGACTCTAAATAcTT    4200
AtCTACCTCCAtCATGTtCGtAGCCACAACCAATCTCCCGACCAATTCCACCTTCAACTTGTCTCtTTGCCCGGGGCCCTCcToCCCAACCACATATGCCtCoAGGcACATTGCCCGGTGCGTTCCGTCCGTAAgCCAAAGcCACAGAGACTTG    4300
TGACCCCCCAgGCCTCCACGGCCCTCACCGATTGCAAcCAAAGCGCTCTAGTCTCcTTTGCGGGGCCCTCcToCCCAACCACATATGCCAAGGTGATGTAACCCAT    4400
CCATACCTGTCAgAtCATCAACTCACAACATCATATGCCTCoAGGcACATTGCCCGGTGCGTTCCGTCCGTAAgCCAAAGcCACAGAGACTTG    4500
TATAAGTACAAAAAATACAAATACTGCCTCCACGTCCTCTGGTAGAACACCTTCCACATTAATACAGATAATGGGCCAGCCTTGtTgTCACAAGAATTCCAGGAGTT    4600
CTATACGGCCtTcCTTCAGGCCAtCtCCCTCCTgGGaAACCACTCACGCTCCACATTAATACAGATAATGGGCCAGCCTTGtTgTCACAAGAATTCCAGGAGTT    4700
TTGTACCTCCTATCaCCATCAAaCATTCTACCCACATACAACCCCACCAGTCCAGGCCTCAGCGCTCAGaGaGACCAAGTGGTaTAATCAAAAAtTTACTA    4800
AACAAATATCTACTAGAtTGTCCTAACCTTCCCATAGACAATGCCATtaACAAAGCCCtCtGGACcCTCAATCAGCTAAATGTCATGAACCCAGTGGTA    4900
AAACCCCATGGCAAATCCATCACAGCCCTCATtgCCACCATTCCTGAAGCCTCTACCCCTCCCAAACCACCACCAtCtAAATGGTTCTATTATAAACTCCC    5000
```

Start TAX/REX
CCTGTCTCCTCCTCAGCCCATTTCCCAGGATTCGGACAGAGCCTCCTATATGGATACCCCGTCTAGTGTTTGGCGATTGTGTACAGGCCGATTGGTGTCC    7300
          3' sj (tax, rex)                                                                                    REX
CGTCTCAGGTGGTCTATGTTCCACCCGCCTACATCGACATGCCCTCCTGGCCACCTGTCCAGAGCACCAgCTCACCTGGACCCCATGATGGACGCGTT        7400
                                                              CIaI
GTCAGCTCTCTCCAATACCTTATCCCTGCCTCCCTCCCCACCCAGAGAAACgCcAaGAGACCCTCAAGGTCCTTACCCCTCCACCACTCCTG              7500
TCTCCCCCAAGGTTCCACCgCCTTCTTCCAATCAATGGGAAAGCACACCCTATCGCAATGGATGCCTGGAACCAACCCCTCGGGATCAGCTCCCCTC          7600
                                                                          End REX
CCTCGGCCTTCCCTgAACCTGGCCTCCGTCCCCCAAAACATCTACACCACCTGGGGAAAAAACCGTAGTgTGCCTgTACCTATtCCAGCTTTCCCACCCATG    7700
ACcTGGCCACTTATACCCCATGTCATATTCTGCACCCaAGACACAATTgGGAGCCCTTCCTCACCAAGGTGCCTCTAAAACGAcTAGAAGAACTTCTATACA    7800
AAATGTTCCATACACAGGagCgGTCATAGTCCTCCCGGAGGAGACCTACCCACCACACAATGTTCCAgCCCGToAGGGCTCCCTGTATCCAGACTGCCTG    7900
GTGTACAGGAGGACTTCTCCCCTATCCATCCACTCCTAACAACCCCAGGcCTAATATGCCTTCAAcGAtGGCTCACCAATGATTTCCGGCCCTtgCCCtAAg  8000
GCAGGGCAGCCAGTCATCTTTAGTAGTTCAaTCCTCtCTATTAATCTTCGAAAAATTCAAACCAAAGCCTTCCATCCCTCTTATCTACTCTCATCAaCTTA    8100
                                                      Start 3' LTR
TACAAATACTCCTCCTTCACCTcCTATTCGAcGAgTACACCAACATCCCTGTCTCTATTTATTTAATAAGAAGAGGCGGAT[GACAATGG               8200
                                                                                    End TAX
CGACcAGCCTCCTgaGCCAGCCgCCCAGCCCGAGTCATCGACCCCAAAAGGTCAGACCTCGAGCTCTCACACAACAATCCCAAGTAA]AGGCTCTGAGCTCTCCCC   8300
C...TTTaTAGGAACTGAAACCAaGgGCCTGAGTCC...CCCCCCaggaAcCAGgaAaAGCTCTCCAG...AAAAATAaACCTCgCCCTTACCCACTCCCCTAGCaC  8400 8500
TGAAAAACAAGGCTCTGACGATTACCCCCCCTGCCCATAAAATTTGCCTAgCCAAAATAAaGAtGCGAGTCTATAAAGCGCAAGGCAAGGACAGTTCAGGAG      8500
                                                                                                            LTR
GTctCTCGGCTCCTtCACCGACCTCCGTCgCGaAGACTCACCTCCATCCTCTCCAAGCGCCCTTCCGTcGAGACGCCTTCCGTGGACtGTCT          8600
CCCGGCCCTCaGCACCCTCCTGAACTGCTCCTtCCAgGGCTAAGTCCTCCTCTCCAGGTCTGCTgGGCTGCCTtGGCTGCCTCCCTCCCGAGGGTCTTTAGA   8700
GACACCCGGGTtCCGGCTCGCCTCTGCCTAGACTCTGCCTTGAAACcTCACTTCCCGGTCTTGGTCTCTGGTCTCTGGTCTCTTCCTCTCGTCACTGAAAACGA    8800
AACtTCAACGCGCCCTtCTGGCAGGCTTGcCCCGGGGCCAgCATACTGcCgcgGcgGGCGCAGtAAGGGCTAGGGCTTCCGTAGGGCTTAGGGGCTCCGGGAGGT  8900
CcATcGCTATAGGCAGGCCCGCCCCaGGGAGCATCTGTCTCTTCCGGGGAAGACAAACA                                          8957
                    End 3' LTR

FIG. 2D

COMPLETE NUCLEOTIDE SEQUENCE OF HTLV-II NRA GENOME.
SMALL CASE LETTERS REPRESENT BASE CHANGES IN HTLV-II NRA AS COMPARED TO HTLV-II MO.
ENZYME RESTRICTION SITES FOR SUBCLONING, INITIATION CODONS AND TERMINATION CODONS ARE HIGHLIGHTED. NUCLEOTIDE DELETIONS IN HTLV-II NRA ARE REPRESENTED BY
(.) AND INSERTIONS ARE UNDERLINED.
BASE 23 AND 8214 (ASTERISKED) DIFFER FROM HTLV-II MO 5' LTR NUCLEOTIDE POSITION 23 BUT NOT FROM 3' LTR NUCLEOTIDE POSITION 8212.

FIG. 2E

SEQUENCE LISTING (1) GENERAL INFORMATION:

(iii) NUMBER OF SEQUENCES: 19

(2) INFORMATION FOR SEQ ID NO:1:

(i) SEQUENCE CHARACTERISTICS:
      (A) LENGTH: 8957 base pairs
      (B) TYPE: nucleic acid
      (C) STRANDEDNESS: single stranded
      (D) TOPOLOGY: linear (xi) SEQUENCE DESCRIPTION: SEQ ID NO:1:

```
TGACAATGGC GACCAGCCTC CTGAGCCAGC CGCCCAGGGC GAGTCATCGA          50

CCCAAAAGGT CAGACCGTCT CACACAAACA ATCCCAAGTA AAGGCTCTGA         100

CGTCTCCCCC TTTATAGGAA CTGAAACCAA GGCCCTGACG TCCCCCCCCA         150

GGAACCAGGA AAAGCTCTCC AGAAAAATAA ACCTCGCCCT TACCCACTTC         200

CCCTAGCACT GAAAACAAG GCTCTGACGA TTACCCCCCT GCCCATAAAA          250

TTTGCCTAGC CAAAAATAAA GGATGCCGAG TCTATAAAAG CGCAAGGACA         300

GTTCAGGAGG TCTCTCGCTC CTTCACCGAC CCTCCGGTCG CGAAGACTCA         350

CCTTGGGGAT CCATCCTCTC CAAGCGGCCT CGGTCGAGAC GCCTTCCGTG         400

GGACTGTCTC CCGGCCTCAG CACCTCCTGA ACTGCTCCTT CCAGGGTAAG         450

TCTCCTCTCA GGTCGAGCTT GGCTGCCTCT TAGGTAGTCG CTCCCCGAGG         500

GTCTTTAGAG ACACCCGGGT TCCCGCCTGC GCTCGGCTAG ACTCTGGCTT         550

GAAACCTCAC TTCCGCGTTC TTGGTCTCGT TCTTTCCTCT TCGTCGTCAC         600

TGAAAACGAA ACTTCAACGC CGCCCTTCTG GCAGGCTTGG CCCGGGGCCA         650

GCATACTGCC GCGGAGGCGC AGTAAGGGCT AGGGCTTCCT GAACCTCTCC         700

GGGAGAGGTC CATCGCTATA GGCAGGCCCG CCCCAGGAGC ATCTGTCTTC         750
```

```
CCGGGGAAGA CAAACAAGTG GGGGCTCGTC CGGGATCTGA ATTCCTCCAT         800

TCTCACATTA TGGGGCAAAT CCACGGGCTT TCCCCAACTC CAATACCCAA         850

GGCCCCCAGG GGGCTATCGA CCCACCACTG GCTTAATTTT CTCCAGGCTG         900

CTTACCGCCT GCAGCCTGGG CCCTCCGATT TCGACTTCCA ACAGCTACGA         950

CGCTTTCTTA AACTGGCCCT TAAAACGCCC ATTTGGCTAA ATCCTATCGA        1000

CTACTCGCTT TTAGCTAGCC TTATCCCCAA AGGATATCCG GGAAGGGTGG        1050

TAGAGATTAT AAACATCCTT GTCAAAAACC AAGTCTCCCC TAGCGCCCCC        1100

GCCGCCCCAG TTCCGACACC TATCTGCCCT ACCACTACCC CTCCGCCACC        1150

TCCCCCCCCT TCCCCGGAGG CCCATGTTCC CCCCCTTAC GTGGAACCCA         1200

CTACCACACA ATGCTTTCCT ATCTTACATC CCCCTGGAGC CCCCTCAGCT        1250

CACAGGCCCT GGCAGATGAA AGACTTACAG GCCATCAAGC AGGAGGTCAG        1300

CTCCTCTGCC CCTGGCAGCC CCCAGTTCAT GCAGACCCTC CGGCTGGCGG        1350

TACAACAGTT TGACCCCACC GCCAAGGACT TACAAGATCT CCTCCAGTAC        1400

CTATGCTCCT CCCTCGTGGT TTCCTTACAC CATCAGCAGC TCAACACACT        1450

AATCACCGAG GCTGAGACTC GCGGGGTGAC AGGCTACAAC CCCATGGCAG        1500

GGCCCCTAAG AATGCAGGCT AATAACCCCG CCCAACAAGG TCTTAGACGG        1550

GAGTACCAGA ACCTTTGGCT GGCTGCTTTC TCCACCCTTC CAGGCAATAC        1600

CCGTGACCCC TCTTGGGCGG CTATCCTACA GGGGCTGGAA GAACCCTACT        1650

GCGCGTTCGT AGAGCGCCTT AATGTGGCCC TTGACAACGG CCTCCCCGAG        1700

GGCACCCCCA AAGAGCCCAT CTTACGCTCC CTAGCGTACT CAAATGCCAA        1750

CAAAGAATGC CAAAAAATCT TACAAGCCCG TGGACACACT AACAGCCCCC        1800

TCGGGGAGAT GCTTCGGGCA TGCCAAGCGT GGACACCCAA GGACAAAACC        1850

AAGGTCCTTG TGGTCCAACC ACGGAGGCCC CCCCCACAC AGCCCTGCTT         1900

TCGTTGTGGC AAGATAGGAC ACTGGAGTCG GGACTGCACC CAGCCACGCC        1950

CCCCTCCTGG CCCCTGCCCC CTATGCCAGG ATCCTTCTCA TTGGAAAAGG        2000

GACTGCCCAC AGCTTAAACC CCCTCAGGAG GAAGGGGAAC CCCTCCTGTT        2050

GGATCTCTCC TCCACCTCAG GTACTACTGA GGAAAAAAAC TCCTTAGGGG        2100

GGGAGATCTA ATCTCCCCCC ATCCCGATCA AGACATCTCA ATACTCCCAC        2150

TCATTCCCCT GCGGCAACAA CAACAACCAA TTCTAGGAGT CCGGATTTCC        2200

GTTATGGGAC AAACACCTCA GCCTACCCAA GCGCTACTTG ACACAGGAGC        2250

CGACCGTACG GTTATACCCC AGACACTCGT GCCTGGGCCG GTAAAGCTCC        2300

ACGACACCCT GGTCCTAGGC GCCAGTGGGC AAACTAATAC CCAGTTCAAA        2350

CTCCTCCAAA CCCCCCTACA CATATTCTTA CCCTTCCGAA AGTCCCCCGT        2400

TATTCTTCCC TCCTGTCTCT TAGACACCCA CAACAAATGG ACCATCATTG        2450

GAAGAGACGC CCTACAACAA TGCCAGGGGC TTCTATACCT TCCAGACGAT        2500

CCCAGCCCCC ATCAATTGCT GCCAATAGCC ACTCCACACA CCATAGGCCT        2550

CGAACACCTT CCCCCACCGC CCCAGGTGGA CCAATTTCCT TTAAACCTGA        2600

GCGCCTCCAG GCCTTAAATG ACCTGGTCTC CAAGGCCCTG GAGGCTGGCC        2650

ACATTGAACC GTACTCAGGA CCAGGCAATA ACCCCGTCTT CCCCGTTAAA        2700

AAACCAAATG GCAAATGGAG GTTCATTCAT GACCTAAGAG CCACCAACGC        2750
```

```
CATCGCTACC ACCCTCACCT CTCCTTCCCC AGGGCCCCCC GACCTCACTA        2800

GCCTACCAAC AGCCTTACCC CACCTACAGA CCATAGACCT TACTGACGCC        2850

TTTTTCCAAA TCCCCCTCCC CAAGCAGTTC CAGCCATACT TCGCCTTCAC        2900

CATTCCCCAG CCATGTAATT ATGGCCCCGG GACCAGATAC GCATGGACTG        2950

TCCTTCCACA GGGGTTTAAA AACAGCCCCA CCCTCTTCGA GCAACAATTA        3000

GCGGCTGTCC TCAACCCCAT GAGGAAAATG TTTCCCACGT CGACCATTGT        3050

CCAATACATG GATGACATAC TTTTGGCCAG CCCCACCAAT AAGGAATTAC        3100

AACAACTCTC CCAGTTAACC CTCCAGGCAC TGACCACACA TGGCCTTCCA        3150

ATCTCCCAGG AAAAAACGCA ACGTACCCCA GGCCAGATAC GCTTCTTAGG        3200

ACAAGTCATC TCCCCTAATC ACATTACATA TGAAAGTACC CCTGCTATTC        3250

CCATAAAATC CCAATGGACA CTCACTGAGC TACAGGTTAT CCTAGGAGAA        3300

ATCCAGTGGG TCTCTAAAGG TACCCCCATC CTTCGCAAAC ACCTACAATC        3350

CCTATATTCT GCCCTTCACG GGTACCGGGA CCCAAGAGCC TGTATCACCC        3400

TTACACCACA ACAACTCCAT GCGCTACATG CCATCCAACA AGCTCTACAA        3450

CATAACTGCC GTGGCCGCCT CGACCCTACC CTACCTCTCC TCGGCCTTAT        3500

CTCGTTGAGT ACATCTGGCA CAACATCTGT CATCTTTCAA CCCAAGCAAA        3550

ACTGGCCCCT GGCTTGGCTC CATACCCCCC ACCCTCCGAC CAGTTTATGT        3600

CCTTGGGGTC ACCTACTGGC CTGTACCATT CTAACTCTAG ACAAATACAC        3650

CCTACAACAT TATGGCCTGC TCTGCCAATC TTTCCACCAC AACATGTCAA        3700

AACAGGCCCT TTGCGACTTC CTAAGGAACT CCCCTCATCC AAGCGTCGGC        3750

ATCCTCATTC ACCACATGGG TCGCTTCCAT AACCTTGGCA GTCAACCGTC        3800

TGGCCCGTGG AAGACTCTCT TACACCTCCC AACCCTTCTC CAGGAACCAC        3850

GACTCCTCAG ACCAATTTTC ACCCTCTCCC CCGTCGTGCT TGACACGGCC        3900

CCCTGCCTTT TTTCCGATGG CTCCCCTCAA AAGGCAGCAT ACGTCCTCTG        3950

GGACCAGACT ATCCTTCAAC AAGACATTAC TCCCCTGCCC CCTCACGAAA        4000

CAAATTCCGC ACAAAAGGGA GAACTCCTTG CACTTATCTA TGGACTACGT        4050

GCTGCCAAGC CATGGCCCTC CCTTAATATC TTCTTAGACT CTAAATACTT        4100

AATCAAATAC CTACACTCCC TCGCCATTGG GGCCTTCCTC GGCACGTCCG        4150

CCCATCAAAC CCTCCAGGCG GCCTTACCAC CCCTACTACA GGGCAAGACC        4200

ATCTACCTCC ATCATGTTCG TAGCCACACC AATCTCCCCG ACCCAATTTC        4250

CACCTTCAAT GAATACACAG ACTCCCTTAT TGTAGCTCCC CTTGTCCCCC        4300

TGACGCCCCA GGGCCTCCAC GGCCTCACCC ATTGCAACCA AAGGGCTCTA        4350

GTCTCCTTTG GCGCCACACC AAAGGAAGCC AAGTCCCTTG TACAGACTTG        4400

CCATACCTGT CAGATCATCA ACTCACAACA TCATATGCCT CAAGGGCACA        4450

TTCGCCGGGG CCTCCTACCC AACCACATAT GGCAAGGTGA TGTAACCCAT        4500

TATAAGTACA AAAAATACAA ATACTGCCTC CACGTCTGGG TAGACACCTT        4550

CTCCGGTGCG GTTTCCGTCT CCTGTAAGAA GAAAGAAACC AGCTGTGAGA        4600

CTATCAGCGC CTTCCTTCAG GCCATCTCCC TCCTGGGAAA ACCACTCCAC        4650

ATTAATACAG ATAATGGGCC AGCCTTCTTG TCACAAGAAT TCCAGGAGTT        4700
```

```
TTGTACCTCC TATCACATCA AACATTCTAC CCACATACCA TACAACCCCA    4750

CCAGCTCAGG CCTGGTCGAA AGGACCAATG GTATAATCAA AAATTTACTA    4800

AACAAATATC TACTAGATTG TCCTAACCTT CCCCTAGACA ATGCCATTAA    4850

CAAAGCCCTC TGGACCCTCA ATCAGCTAAA TGTCATGAAC CCCAGTGGTA    4900

AAACCCGATG GCAAATCCAT CACAGCCCTC CATTGCCACC CATTCCTGAA    4950

GCCTCTACCC CTCCCAAACC ACCATCTAAA TGGTTCTATT ATAAACTCCC    5000

CGGCCTTACC AATCAGCGGT GGAAAGGTCC ATTACAATCC CTCCAGGAAG    5050

CGGCTGGGGC AGCCCTGCTC TCCATAGACG GCTTCCCCCG GTGGATCCCG    5100

TGGCGATTCC TGAAAAAAGC TGCATGCCCA AGACCAGACG CCAGCGAACC    5150

CGCCGAGCAC GCCGCAACAG ACCACCAACA CCATGGGTAA CGTTTTCTTC    5200

CTACTTTTAT TCAGTCTCAC ACACTTCCCA CCAGTCCAGC AGAGCCGATG    5250

CACACTCACG GTTGGTATTT CCTCCTACCA CTCCAGCCCC TGTAGCCCAA    5300

CCCAACCCGT CTGCACGTGG AACCTCGACC TTAATTCCCT AACGACGGAC    5350

CAGCGACTAC ATCCCCCCTG CCCTAACCTA ATTACTTACT CTGGCTTCCA    5400

CAAAACTTAT TCCTTATACT TATTCCCACA TTGGATAAAG AAGCCAAATA    5450

GACAGGGCCT AGGATACTAC TCGCCCTCCT ATAATGACCC TTGCTCGCTA    5500

CAATGCCCCT ACTTAGGCTG CCAATCATGG ACATGCCCAT ACACGGGCCC    5550

CGTCTCCAGT CCATCCTGGA AGTTTCACTC AGATGTAAAT TTCACCCAAG    5600

AAGTCAGCCA AGTGTCCCTT CGACTACACT TCTCTAAGTG CGGCTCCTCC    5650

ATGACCCTTC TAGTAGATGC CCCTGGATAT GATCCTTTAT GGTTCATCAC    5700

CTCAGAACCC ACTCAGCCTC CCCCAACTCC TCCCCCACTG GTCCATGACT    5750

CCGACCTTGA ACACGTCCTA ACCCCCTCCA CGTCTTGGAC AACCAAAATG    5800

CTCAAGTTTA TCCAGCTGAC CTTGCAGAGC ACCAATTACT CCTGCATGGT    5850

TTGCGTGGAT AGATCCAGCC TCTCATCCTG GCATGTGCTC TACACCCCCA    5900

ACATCTCCAT TCCCCAACAA ACCTCCTCCC GAACCATCCT CTTTCCTTCT    5950

CTTGCCCTGC CCGCTCCTCC ATTCCAACCC TTCCCTTGGA CCCATTGCTA    6000

CCAACCTCGC CTACAGGCAA TAACGACAGA TGACTGCAAC AACTCCATTA    6050

TCCTCCCCCC TTTTTCCCTC GCCCCGTAC CTCCTCCGGC GACAAGACGC    6100

CGCCGTGCCG TTCCAATAGC AGTGTGGCTT GTCTCCGCTC TAGCGGCCGG    6150

GACAGGTATC GCTGGCGGAG TAACAGGCTC CCTATCTCTA GCTTCCAGTA    6200

AAAGCCTTCT CTTCGAGGTT GACAAAGATA TCTCCCACCT TACCCAGGCC    6250

ATAGTCAAAA ATCATCAAAA CATCCTCCGG GTTGCACAAT ATGCAGCCCA    6300

GAATAGACGA GGATTAGACC TCCTATTCTG GAACAAGGG GGTTTGTGCA    6350

AAGCCATACA GGAGCAATGT TGCTTCCTCA ATATCAGTAA CACTCATGTA    6400

TCCGTCCTCC AAGAACGGCC CCCTCTTGAA AAGCGTGTCA TCACCGGTTG    6450

GGGACTAAAC TGGGATCTTG GTCTGTCCCA GTGGGCACGA GAAGCCCTCC    6500

AGACAGGCAT AACCATTCTC ACCCTACTCC TCCTTGTCAT ATTGTTTGGC    6550

CCCTGCATCC TCCGCCAAAT CCAAGCCCTT CCGCAGCGGT TACAAAACCG    6600

ACATAGCCAG TATGCCCTTA TCAACCAAGA GACCATGCTA TAATAGACCC    6650

GCTAGCTTCT GCAGCAAATC CCCATGGTTC ATCCCCCTAC CATTGACCCA    6700
```

-continued

```
TCCACAGTCT TCTATGCCAG ATGAGTCACC CCCGATGTCC AGCCCCGACT      6750

CAAACTCAAT AATTGCCTCA AATAGCTCCT CCAACCCCCG CTCACATTCC      6800

TCCCATAGGG CCTTTTTTTC CTCTTCCAAG AAATCCACAT AACCCTGAAG      6850

CAAATCACAA AACCCATCAA AACCCAGGAG TCCTATACAC TCCAACTGCT      6900

GATGCCTCTC TTCCCTCTCC CGGCGCTTTT GATCCTTTTC CCGCAGGCGC      6950

TCCTTTCTGC GCCGCTCCCG CTCCTCACGC TCCTGCAGAA GCTTTAAGAT      7000

CTCCCGCTGC TCCTCCGCCA ACAGCTTCCG ACGAGAGTCT CGCACCTGCT      7050

CGCTGACCGA TCCCGACCCC AGAGGGCGGC CTTTTGCTGT CCTTCTTGGT      7100

TCCTCTCCAG GGGGAGGCAC ATCAGATGTC AGACTCTCCT CCCCCTGGTC      7150

TCCTAACGGC AATCTCCTAA AATAGTCTAA AAATTACACA TAATTACAAC      7200

CCTGTCTCCT CTCAGCCCAT TTCCCAGGAT TCGGACAGAG CCTCCTATAT      7250

GGATACCCCG TCTACGTGTT TGGCGATTGT GTACAGGCCG ATTGGTGTCC      7300

CGTCTCAGGT GGTCTATGTT CCACCCGCCT ACATCGACAT GCCCTCCTGG      7350

CCACCTGTCC AGAGCACCAG CTCACCTGGG ACCCCATCGA TGGACGCGTT      7400

GTCAGCTCTC CTCTCCAATA CCTTATCCCT CGCCTCCCCT CCTTCCCCAC      7450

CCAGAGAACC GCCAAGACCC TCAAGGTCCT TACCCCTCCC ACCACTCCTG      7500

TCTCCCCCAA GGTTCCACCC GCCTTCTTCC AATCAATGCG AAAGCACACC      7550

CCCTATCGCA ATGGATGCCT GGAACCAACC CTCGGGGATC AGCTCCCCTC      7600

CCTCGCCTTC CCTGAACCTG GCCTCCGTCC CCAAAACATC TACACCACCT      7650

GGGGAAAAAC CGTAGTGTGC CTGTACCTAT TCCAGCTTTC CCCACCCATG      7700

ACCTGGCCAC TTATACCCCA TGTCATATTC TGCCACCCAA GACAATTGGG      7750

AGCCTTCCTC ACCAAGGTGC CTCTAAAACG ACTAGAAGAA CTTCTATACA      7800

AAATGTTCCT ACACACAGGA GCGGTCATAG TCCTCCCGGA GGACGACCTA      7850

CCCACCACAA TGTTCCAGCC CGTAAGGGCT CCCTGTATCC AGACTGCCTG      7900

GTGTACAGGA CTTCTCCCCT ATCACTCCAT CCTAACAACC CCAGGCCTAA      7950

TATGGACCTT CAACGATGGC TCACCAATGA TTTCCGGCCC TTGCCCTAAG      8000

GCAGGGCAGC CATCTTTAGT AGTTCAATCC TCTCTATTAA TCTTCGAAAA      8050

ATTCCAAACC AAAGCCTTCC ATCCCTCTTA TCTACTCTCT CATCAACTTA      8100

TACAATACTC CTCCTTCCAT AACCTTCACC TCCTATTCGA CGAGTACACC      8150

AACATCCCTG TCTCTATTTT ATTTAATAAA GAAGAGGCGG ATGACAATGG      8200

CGACCAGCCT CCTGAGCCAG CCGCCCAGGG CGAGTCATCG ACCCAAAAGG      8250

TCAGACCGTC TCACACAAAC AATCCCAAGT AAAGGCTCTG ACGTCTCCCC      8300

CTTTATAGGA ACTGAAACCA AGGCCCTGAC GTCCCCCCCC AGGAACCAGG      8350

AAAAGCTCTC CAGAAAAATA AACCTCGCCC TTACCCACTT CCCCTAGCAC      8400

TGAAAAACAA GGCTCTGACG ATTACCCCCC TGCCCATAAA ATTTGCCTAG      8450

CCAAAAATAA AGGATGCCGA GTCTATAAAA GCGCAAGGAC AGTTCAGGAG      8500

GTCTCTCGCT CCTTCACCGA CCCTCCGGTC GCGAAGACTC ACCTTGGGGA      8550

TCCATCCTCT CCAAGCGGCC TCGGTCGAGA CGCCTTCCGT GGGACTGTCT      8600

CCCGGCCTCA GCACCTCCTG AACTGCTCCT TCCAGGGTAA GTCTCCTCTC      8650
```

-continued

| | |
|---|---|
| AGGTCGAGCT TGGCTGCCTC TTAGGTAGTC GCTCCCCGAG GGTCTTTAGA | 8700 |
| GACACCCGGG TTCCCGCCTG CGCTCGGCTA GACTCTGGCT TGAAACCTCA | 8750 |
| CTTCCGCGTT CTTGGTCTCG TTCTTTCCTC TTCGTCGTCA CTGAAAACGA | 8800 |
| AACTTCAACG CCGCCCTTCT GGCAGGCTTG GCCCGGGGCC AGCATACTGC | 8850 |
| CGCGGAGGCG CAGTAAGGGC TAGGGCTTCC TGAACCTCTC CGGGAGAGGT | 8900 |
| CCATCGCTAT AGGCAGGCCC GCCCCAGGAG CATCTGTCTT CCCGGGGAAG | 8950 |
| ACAAACA | 8957 |

(2) INFORMATION FOR SEQ ID NO:2:

(i) SEQUENCE CHARACTERISTICS:
        (A) LENGTH: 1302 base pairs
        (B) TYPE: nucleic acid
        (C) STRANDEDNESS: single stranded
        (D) TOPOLOGY: linear (xi) SEQUENCE DESCRIPTION: SEQ ID NO:2:

| | |
|---|---|
| ATG GGG CAA ATC CAC GGG CTT TCC CCA ACT CCA ATA CCC AAG<br>Met Gly Gln Ile His Gly Leu Ser Pro Thr Pro Ile Pro Lys<br>                    5                    10 | 42 |
| GCC CCC AGG GGG CTA TCG ACC CAC CAC TGG CTT AAT TTT CTC<br>Ala Pro Arg Gly Leu Ser Thr His His Trp Leu Asn Phe Leu<br>15                  20                  25 | 84 |
| CAG GCT GCT TAC CGC CTG CAG CCT GGG CCC TCC GAT TTC GAC<br>Gln Ala Ala Tyr Arg Leu Gln Pro Gly Pro Ser Asp Phe Asp<br>     30                   35                 40 | 126 |
| TTC CAA CAG CTA CGA CGC TTT CTT AAA CTG GCC CTT AAA ACG<br>Phe Gln Gln Leu Arg Arg Phe Leu Lys Leu Ala Leu Lys Thr<br>          45                    50               55 | 168 |
| CCC ATT TGG CTA AAT CCT ATC GAC TAC TCG CTT TTA GCT AGC<br>Pro Ile Trp Leu Asn Pro Ile Asp Tyr Ser Leu Leu Ala Ser<br>              60                    65               70 | 210 |
| CTT ATC CCC AAA GGA TAT CCG GGA AGG GTG GTA GAG ATT ATA<br>Leu Ile Pro Lys Gly Tyr Pro Gly Arg Val Val Glu Ile Ile<br>                 75                    80 | 252 |
| AAC ATC CTT GTC AAA AAC CAA GTC TCC CCT AGC GCC CCC GCC<br>Asn Ile Leu Val Lys Asn Gln Val Ser Pro Ser Ala Pro Ala<br>85                  90                  95 | 294 |
| GCC CCA GTT CCG ACA CCT ATC TGC CCT ACC ACT ACC CCT CCG<br>Ala Pro Val Pro Thr Pro Ile Cys Pro Thr Thr Thr Pro Pro<br>          100                 105               110 | 336 |
| CCA CCT CCC CCC CCT TCC CCG GAG GCC CAT GTT CCC CCC CCT<br>Pro Pro Pro Pro Pro Ser Pro Glu Ala His Val Pro Pro Pro<br>          115                 120               125 | 378 |
| TAC GTG GAA CCC ACT ACC ACA CAA TGC TTT CCT ATC TTA CAT<br>Tyr Val Glu Pro Thr Thr Thr Gln Cys Phe Pro Ile Leu His<br>              130                 135               140 | 420 |
| CCC CCT GGA GCC CCC TCA GCT CAC AGG CCC TGG CAG ATG AAA<br>Pro Pro Gly Ala Pro Ser Ala His Arg Pro Trp Gln Met Lys<br>                 145                 150 | 462 |
| GAC TTA CAG GCC ATC AAG CAG GAG GTC AGC TCC TCT GCC CCT<br>Asp Leu Gln Ala Ile Lys Gln Glu Val Ser Ser Ser Ala Pro<br>155                  160                 165 | 504 |
| GGC AGC CCC CAG TTC ATG CAG ACC CTC CGG CTG GCG GTA CAA<br>Gly Ser Pro Gln Phe Met Gln Thr Leu Arg Leu Ala Val Gln<br>          170                 175               180 | 546 |
| CAG TTT GAC CCC ACC GCC AAG GAC TTA CAA GAT CTC CTC CAG<br>Gln Phe Asp Pro Thr Ala Lys Asp Leu Gln Asp Leu Leu Gln | 588 |

```
              185                 190                      195
TAC CTA TGC TCC TCC CTC GTG GTT TCC TTA CAC CAT CAG CAG           630
Tyr Leu Cys Ser Ser Leu Val Val Ser Leu His His Gln Gln
            200                 205                  210

CTC AAC ACA CTA ATC ACC GAG GCT GAG ACT CGC GGG GTG ACA           672
Leu Asn Thr Leu Ile Thr Glu Ala Glu Thr Arg Gly Val Thr
                    215                 220

GGC TAC AAC CCC ATG GCA GGG CCC CTA AGA ATG CAG GCT AAT           714
Gly Tyr Asn Pro Met Ala Gly Pro Leu Arg Met Gln Ala Asn
225                 230                  235

AAC CCC GCC CAA CAA GGT CTT AGA CGG GAG TAC CAG AAC CTT           756
Asn Pro Ala Gln Gln Gly Leu Arg Arg Glu Tyr Gln Asn Leu
    240                 245                  250

TGG CTG GCT GCT TTC TCC ACC CTT CCA GGC AAT ACC CGT GAC           798
Trp Leu Ala Ala Phe Ser Thr Leu Pro Gly Asn Thr Arg Asp
        255                 260                  265

CCC TCT TGG GCG GCT ATC CTA CAG GGG CTG GAA GAA CCC TAC           840
Pro Ser Trp Ala Ala Ile Leu Gln Gly Leu Glu Glu Pro Tyr
            270                 275                  280

TGC GCG TTC GTA GAG CGC CTT AAT GTG GCC CTT GAC AAC GGC           882
Cys Ala Phe Val Glu Arg Leu Asn Val Ala Leu Asp Asn Gly
                285                 290

CTC CCC GAG GGC ACC CCC AAA GAG CCC ATC TTA CGC TCC CTA           924
Leu Pro Glu Gly Thr Pro Lys Glu Pro Ile Leu Arg Ser Leu
295                 300                  305

GCG TAC TCA AAT GCC AAC AAA GAA TGC CAA AAA ATC TTA CAA           966
Ala Tyr Ser Asn Ala Asn Lys Glu Cys Gln Lys Ile Leu Gln
    310                 315                  320

GCC CGT GGA CAC ACT AAC AGC CCC CTC GGG GAG ATG CTT CGG          1008
Ala Arg Gly His Thr Asn Ser Pro Leu Gly Glu Met Leu Arg
        325                 330                  335

GCA TGC CAA GCG TGG ACA CCC AAG GAC AAA ACC AAG GTC CTT          1050
Ala Cys Gln Ala Trp Thr Pro Lys Asp Lys Thr Lys Val Leu
            340                 345                  350

GTG GTC CAA CCA CGG AGG CCC CCC CCA ACA CAG CCC TGC TTT          1092
Val Val Gln Pro Arg Arg Pro Pro Pro Thr Gln Pro Cys Phe
                355                 360

CGT TGT GGC AAG ATA GGA CAC TGG AGT CGG GAC TGC ACC CAG          1134
Arg Cys Gly Lys Ile Gly His Trp Ser Arg Asp Cys Thr Gln
365                 370                  375

CCA CGC CCC CCT CCT GGC CCC TGC CCC CTA TGC CAG GAT CCT          1176
Pro Arg Pro Pro Pro Gly Pro Cys Pro Leu Cys Gln Asp Pro
    380                 385                  390

TCT CAT TGG AAA AGG GAC TGC CCA CAG CTT AAA CCC CCT CAG          1218
Ser His Trp Lys Arg Asp Cys Pro Gln Leu Lys Pro Pro Gln
        395                 400                  405

GAG GAA GGG GAA CCC CTC CTG TTG GAT CTC TCC TCC ACC TCA          1260
Glu Glu Gly Glu Pro Leu Leu Leu Asp Leu Ser Ser Thr Ser
            410                 415                  420

GGT ACT ACT GAG GAA AAA AAC TCC TTA GGG GGG GAG ATC TAA          1302
Gly Thr Thr Glu Glu Lys Asn Ser Leu Gly Gly Glu Ile
                425                 430
```

(2) INFORMATION FOR SEQ ID NO:3:

(i) SEQUENCE CHARACTERISTICS:
        (A) LENGTH: 433 amino acids
        (B) TYPE: amino acid
        (C) STRANDEDNESS:
        (D) TOPOLOGY: unknown (xi) SEQUENCE DESCRIPTION: SEQ ID NO:3:

```
Met Gly Gln Ile His Gly Leu Ser Pro Thr Pro Ile Pro Lys
                 5                  10

Ala Pro Arg Gly Leu Ser Thr His His Trp Leu Asn Phe Leu
 15              20                  25

Gln Ala Ala Tyr Arg Leu Gln Pro Gly Pro Ser Asp Phe Asp
         30                  35                  40

Phe Gln Gln Leu Arg Arg Phe Leu Lys Leu Ala Leu Lys Thr
             45                  50                  55

Pro Ile Trp Leu Asn Pro Ile Asp Tyr Ser Leu Leu Ala Ser
                 60                  65                  70

Leu Ile Pro Lys Gly Tyr Pro Gly Arg Val Val Glu Ile Ile
                     75                  80

Asn Ile Leu Val Lys Asn Gln Val Ser Pro Ser Ala Pro Ala
 85              90                  95

Ala Pro Val Pro Thr Pro Ile Cys Pro Thr Thr Thr Pro Pro
        100                 105                 110

Pro Pro Pro Pro Ser Pro Glu Ala His Val Pro Pro Pro
            115                 120                 125

Tyr Val Glu Pro Thr Thr Thr Gln Cys Phe Pro Ile Leu His
            130                 135                 140

Pro Pro Gly Ala Pro Ser Ala His Arg Pro Trp Gln Met Lys
                145                 150

Asp Leu Gln Ala Ile Lys Gln Glu Val Ser Ser Ser Ala Pro
155                 160                 165

Gly Ser Pro Gln Phe Met Gln Thr Leu Arg Leu Ala Val Gln
    170                 175                 180

Gln Phe Asp Pro Thr Ala Lys Asp Leu Gln Asp Leu Leu Gln
        185                 190                 195

Tyr Leu Cys Ser Ser Leu Val Val Ser Leu His His Gln Gln
            200                 205                 210

Leu Asn Thr Leu Ile Thr Glu Ala Glu Thr Arg Gly Val Thr
                215                 220

Gly Tyr Asn Pro Met Ala Gly Pro Leu Arg Met Gln Ala Asn
225                 230                 235

Asn Pro Ala Gln Gln Gly Leu Arg Arg Glu Tyr Gln Asn Leu
    240                 245                 250

Trp Leu Ala Ala Phe Ser Thr Leu Pro Gly Asn Thr Arg Asp
        255                 260                 265

Pro Ser Trp Ala Ala Ile Leu Gln Gly Leu Glu Glu Pro Tyr
            270                 275                 280

Cys Ala Phe Val Glu Arg Leu Asn Val Ala Leu Asp Asn Gly
                285                 290

Leu Pro Glu Gly Thr Pro Lys Glu Pro Ile Leu Arg Ser Leu
295                 300                 305

Ala Tyr Ser Asn Ala Asn Lys Glu Cys Gln Lys Ile Leu Gln
    310                 315                 320

Ala Arg Gly His Thr Asn Ser Pro Leu Gly Glu Met Leu Arg
        325                 330                 335

Ala Cys Gln Ala Trp Thr Pro Lys Asp Lys Thr Lys Val Leu
            340                 345                 350

Val Val Gln Pro Arg Arg Pro Pro Thr Gln Pro Cys Phe
                355                 360
```

```
Arg Cys Gly Lys Ile Gly His Trp Ser Arg Asp Cys Thr Gln
365                 370                 375

Pro Arg Pro Pro Pro Gly Pro Cys Pro Leu Cys Gln Asp Pro
380                 385                 390

Ser His Trp Lys Arg Asp Cys Pro Gln Leu Lys Pro Pro Gln
        395                 400                 405

Glu Glu Gly Glu Pro Leu Leu Leu Asp Leu Ser Ser Thr Ser
            410                 415                 420

Gly Thr Thr Glu Glu Lys Asn Ser Leu Gly Gly Glu Ile
                425                 430
```

(2) INFORMATION FOR SEQ ID NO:4:

(i) SEQUENCE CHARACTERISTICS:
        (A) LENGTH: 408 base pairs
        (B) TYPE: nucleic acid
        (C) STRANDEDNESS: single stranded
        (D) TOPOLOGY: linear (xi) SEQUENCE DESCRIPTION: SEQ ID NO:4:

```
ATG GGG CAA ATC CAC GGG CTT TCC CCA ACT CCA ATA CCC AAG                 42
Met Gly Gln Ile His Gly Leu Ser Pro Thr Pro Ile Pro Lys
                5                   10

GCC CCC AGG GGG CTA TCG ACC CAC CAC TGG CTT AAT TTT CTC                 84
Ala Pro Arg Gly Leu Ser Thr His His Trp Leu Asn Phe Leu
15                  20                  25

CAG GCT GCT TAC CGC CTG CAG CCT GGG CCC TCC GAT TTC GAC                126
Gln Ala Ala Tyr Arg Leu Gln Pro Gly Pro Ser Asp Phe Asp
        30                  35                  40

TTC CAA CAG CTA CGA CGC TTT CTT AAA CTG GCC CTT AAA ACG                168
Phe Gln Gln Leu Arg Arg Phe Leu Lys Leu Ala Leu Lys Thr
                45                  50                  55

CCC ATT TGG CTA AAT CCT ATC GAC TAC TCG CTT TTA GCT AGC                210
Pro Ile Trp Leu Asn Pro Ile Asp Tyr Ser Leu Leu Ala Ser
                    60                  65                  70

CTT ATC CCC AAA GGA TAT CCG GGA AGG GTG GTA GAG ATT ATA                252
Leu Ile Pro Lys Gly Tyr Pro Gly Arg Val Val Glu Ile Ile
            75                  80

AAC ATC CTT GTC AAA AAC CAA GTC TCC CCT AGC GCC CCC GCC                294
Asn Ile Leu Val Lys Asn Gln Val Ser Pro Ser Ala Pro Ala
85                  90                  95

GCC CCA GTT CCG ACA CCT ATC TGC CCT ACC ACT ACC CCT CCG                336
Ala Pro Val Pro Thr Pro Ile Cys Pro Thr Thr Thr Pro Pro
        100                 105                 110

CCA CCT CCC CCC CCT TCC CCG GAG GCC CAT GTT CCC CCC CCT                378
Pro Pro Pro Pro Pro Ser Pro Glu Ala His Val Pro Pro Pro
            115                 120                 125

TAC GTG GAA CCC ACT ACC ACA CAA TGC TTT                                408
Tyr Val Glu Pro Thr Thr Thr Gln Cys Phe
                130
```

(2) INFORMATION FOR SEQ ID NO:5:

(i) SEQUENCE CHARACTERISTICS:
        (A) LENGTH: 136 amino acids
        (B) TYPE: amino acid
        (C) STRANDEDNESS:
        (D) TOPOLOGY: unknown (xi) SEQUENCE DESCRIPTION: SEQ ID NO:5:

Met Gly Gln Ile His Gly Leu Ser Pro Thr Pro Ile Pro Lys

```
                   5                          10
Ala Pro Arg Gly Leu Ser Thr His His Trp Leu Asn Phe Leu
 15                  20                      25

Gln Ala Ala Tyr Arg Leu Gln Pro Gly Pro Ser Asp Phe Asp
         30                  35                      40

Phe Gln Gln Leu Arg Arg Phe Leu Lys Leu Ala Leu Lys Thr
             45                  50                  55

Pro Ile Trp Leu Asn Pro Ile Asp Tyr Ser Leu Leu Ala Ser
                 60                  65                  70

Leu Ile Pro Lys Gly Tyr Pro Gly Arg Val Val Glu Ile Ile
                     75                  80

Asn Ile Leu Val Lys Asn Gln Val Ser Pro Ser Ala Pro Ala
 85                  90                  95

Ala Pro Val Pro Thr Pro Ile Cys Pro Thr Thr Thr Pro Pro
100                 105                 110

Pro Pro Pro Pro Pro Ser Pro Glu Ala His Val Pro Pro Pro
            115                 120                 125

Tyr Val Glu Pro Thr Thr Thr Gln Cys Phe
            130                 135
```

(2) INFORMATION FOR SEQ ID NO:6:

(i) SEQUENCE CHARACTERISTICS:
        (A) LENGTH: 642 base pairs
        (B) TYPE: nucleic acid
        (C) STRANDEDNESS: single stranded
        (D) TOPOLOGY: linear (xi) SEQUENCE DESCRIPTION: SEQ ID NO:6:

```
CCT ATC TTA CAT CCC CCT GGA GCC CCC TCA GCT CAC AGG CCC          42
Pro Ile Leu His Pro Pro Gly Ala Pro Ser Ala His Arg Pro
                 5                  10

TGG CAG ATG AAA GAC TTA CAG GCC ATC AAG CAG GAG GTC AGC          84
Trp Gln Met Lys Asp Leu Gln Ala Ile Lys Gln Glu Val Ser
 15                  20                  25

TCC TCT GCC CCT GGC AGC CCC CAG TTC ATG CAG ACC CTC CGG         126
Ser Ser Ala Pro Gly Ser Pro Gln Phe Met Gln Thr Leu Arg
         30                  35                  40

CTG GCG GTA CAA CAG TTT GAC CCC ACC GCC AAG GAC TTA CAA         168
Leu Ala Val Gln Gln Phe Asp Pro Thr Ala Lys Asp Leu Gln
             45                  50                  55

GAT CTC CTC CAG TAC CTA TGC TCC TCC CTC GTG GTT TCC TTA         210
Asp Leu Leu Gln Tyr Leu Cys Ser Ser Leu Val Val Ser Leu
                 60                  65                  70

CAC CAT CAG CAG CTC AAC ACA CTA ATC ACC GAG GCT GAG ACT         252
His His Gln Gln Leu Asn Thr Leu Ile Thr Glu Ala Glu Thr
                     75                  80

CGC GGG GTG ACA GGC TAC AAC CCC ATG GCA GGG CCC CTA AGA         294
Arg Gly Val Thr Gly Tyr Asn Pro Met Ala Gly Pro Leu Arg
 85                  90                  95

ATG CAG GCT AAT AAC CCC GCC CAA CAA GGT CTT AGA CGG GAG         336
Met Gln Ala Asn Asn Pro Ala Gln Gln Gly Leu Arg Arg Glu
        100                 105                 110

TAC CAG AAC CTT TGG CTG GCT GCT TTC TCC ACC CTT CCA GGC         378
Tyr Gln Asn Leu Trp Leu Ala Ala Phe Ser Thr Leu Pro Gly
            115                 120                 125

AAT ACC CGT GAC CCC TCT TGG GCG GCT ATC CTA CAG GGG CTG         420
Asn Thr Arg Asp Pro Ser Trp Ala Ala Ile Leu Gln Gly Leu
                130                 135                 140
```

```
GAA GAA CCC TAC TGC GCG TTC GTA GAG CGC CTT AAT GTG GCC          462
Glu Glu Pro Tyr Cys Ala Phe Val Glu Arg Leu Asn Val Ala
                145                 150

CTT GAC AAC GGC CTC CCC GAG GGC ACC CCC AAA GAG CCC ATC          504
Leu Asp Asn Gly Leu Pro Glu Gly Thr Pro Lys Glu Pro Ile
155                 160                 165

TTA CGC TCC CTA GCG TAC TCA AAT GCC AAC AAA GAA TGC CAA          546
Leu Arg Ser Leu Ala Tyr Ser Asn Ala Asn Lys Glu Cys Gln
        170                 175                 180

AAA ATC TTA CAA GCC CGT GGA CAC ACT AAC AGC CCC CTC GGG          588
Lys Ile Leu Gln Ala Arg Gly His Thr Asn Ser Pro Leu Gly
            185                 190                 195

GAG ATG CTT CGG GCA TGC CAA GCG TGG ACA CCC AAG GAC AAA          630
Glu Met Leu Arg Ala Cys Gln Ala Trp Thr Pro Lys Asp Lys
                200                 205                 210

ACC AAG GTC CTT                                                  642
Thr Lys Val Leu
```

(2) INFORMATION FOR SEQ ID NO:7:

(i) SEQUENCE CHARACTERISTICS:
　　　　(A) LENGTH: 214 amino acids
　　　　(B) TYPE: amino acid
　　　　(C) STRANDEDNESS:
　　　　(D) TOPOLOGY: unknown (xi) SEQUENCE DESCRIPTION: SEQ ID NO:7:

```
Pro Ile Leu His Pro Pro Gly Ala Pro Ser Ala His Arg Pro
                5                  10

Trp Gln Met Lys Asp Leu Gln Ala Ile Lys Gln Glu Val Ser
15                  20                  25

Ser Ser Ala Pro Gly Ser Pro Gln Phe Met Gln Thr Leu Arg
        30                  35                  40

Leu Ala Val Gln Gln Phe Asp Pro Thr Ala Lys Asp Leu Gln
            45                  50                  55

Asp Leu Leu Gln Tyr Leu Cys Ser Ser Leu Val Val Ser Leu
                60                  65                  70

His His Gln Gln Leu Asn Thr Leu Ile Thr Glu Ala Glu Thr
                    75                  80

Arg Gly Val Thr Gly Tyr Asn Pro Met Ala Gly Pro Leu Arg
85                  90                  95

Met Gln Ala Asn Asn Pro Ala Gln Gln Gly Leu Arg Arg Glu
        100                 105                 110

Tyr Gln Asn Leu Trp Leu Ala Ala Phe Ser Thr Leu Pro Gly
            115                 120                 125

Asn Thr Arg Asp Pro Ser Trp Ala Ala Ile Leu Gln Gly Leu
                130                 135                 140

Glu Glu Pro Tyr Cys Ala Phe Val Glu Arg Leu Asn Val Ala
                145                 150

Leu Asp Asn Gly Leu Pro Glu Gly Thr Pro Lys Glu Pro Ile
155                 160                 165

Leu Arg Ser Leu Ala Tyr Ser Asn Ala Asn Lys Glu Cys Gln
        170                 175                 180

Lys Ile Leu Gln Ala Arg Gly His Thr Asn Ser Pro Leu Gly
            185                 190                 195

Glu Met Leu Arg Ala Cys Gln Ala Trp Thr Pro Lys Asp Lys
                200                 205                 210
```

Thr Lys Val Leu (2) INFORMATION FOR SEQ ID NO:8:

(i) SEQUENCE CHARACTERISTICS:
        (A) LENGTH: 252 base pairs
        (B) TYPE: nucleic acid
        (C) STRANDEDNESS: single stranded
        (D) TOPOLOGY: linear (xi) SEQUENCE DESCRIPTION: SEQ ID NO:8:

```
GTG GTC CAA CCA CGG AGG CCC CCC CCC ACA CAG CCC TGC TTT           42
Val Val Gln Pro Arg Arg Pro Pro Pro Thr Gln Pro Cys Phe
                 5                  10

CGT TGT GGC AAG ATA GGA CAC TGG AGT CGG GAC TGC ACC CAG           84
Arg Cys Gly Lys Ile Gly His Trp Ser Arg Asp Cys Thr Gln
 15              20                  25

CCA CGC CCC CCT CCT GGC CCC TGC CCC CTA TGC CAG GAT CCT          126
Pro Arg Pro Pro Pro Gly Pro Cys Pro Leu Cys Gln Asp Pro
     30              35                  40

TCT CAT TGG AAA AGG GAC TGC CCA CAG CTT AAA CCC CCT CAG          168
Ser His Trp Lys Arg Asp Cys Pro Gln Leu Lys Pro Pro Gln
         45              50                  55

GAG GAA GGG GAA CCC CTC CTG TTG GAT CTC TCC TCC ACC TCA          210
Glu Glu Gly Glu Pro Leu Leu Leu Asp Leu Ser Ser Thr Ser
             60                  65                  70

GGT ACT ACT GAG GAA AAA AAC TCC TTA GGG GGG GAG ATC TAA          252
Gly Thr Thr Glu Glu Lys Asn Ser Leu Gly Gly Glu Ile
                 75                  80
```

(2) INFORMATION FOR SEQ ID NO:9:

(i) SEQUENCE CHARACTERISTICS:
        (A) LENGTH: 83 amino acids
        (B) TYPE: amino acid
        (C) STRANDEDNESS:
        (D) TOPOLOGY: unknown (xi) SEQUENCE DESCRIPTION: SEQ ID NO:9:

```
Val Val Gln Pro Arg Arg Pro Pro Pro Thr Gln Pro Cys Phe
                 5                  10

Arg Cys Gly Lys Ile Gly His Trp Ser Arg Asp Cys Thr Gln
 15              20                  25

Pro Arg Pro Pro Pro Gly Pro Cys Pro Leu Cys Gln Asp Pro
     30              35                  40

Ser His Trp Lys Arg Asp Cys Pro Gln Leu Lys Pro Pro Gln
         45              50                  55

Glu Glu Gly Glu Pro Leu Leu Leu Asp Leu Ser Ser Thr Ser
             60                  65                  70

Gly Thr Thr Glu Glu Lys Asn Ser Leu Gly Gly Glu Ile
                 75                  80
```

(2) INFORMATION FOR SEQ ID NO:10:

(i) SEQUENCE CHARACTERISTICS:
        (A) LENGTH: 2949 base pairs
        (B) TYPE: nucleic acid
        (C) STRANDEDNESS: single stranded
        (D) TOPOLOGY: linear (xi) SEQUENCE DESCRIPTION: SEQ ID NO:10:

```
CACAGGAGCC GACCGTACGG TTATACCCCA GACACTCGTG CCTGGGCCGG           50
```

```
TAAAGCTCCA CGACACCCTG GTCCTAGGCG CCAGTGGGCA AACTAATACC              100

CAGTTCAAAC TCCTCCAAAC CCCCCTACAC ATATTCTTAC CCTTCCGAAA              150

GTCCCCCGTT ATTCTTCCCT CCTGTCTCTT AGACACCCAC AACAA ATG              198
                                                   Met

GAC CAT CAT TGG AAG AGA CGC CCT ACA ACA ATG CCA GGG GCT             240
Asp His His Trp Lys Arg Arg Pro Thr Thr Met Pro Gly Ala
                5                   10                  15

TCT ATA CCT TCC AGA CGA TCC CAG CCC CCA TCA ATT GCT GCC             282
Ser Ile Pro Ser Arg Arg Ser Gln Pro Pro Ser Ile Ala Ala
                20                  25

AAT AGC CAC TCC ACA CAC CAT AGG CCT CGA ACA CCT TCC CCC             324
Asn Ser His Ser Thr His His Arg Pro Arg Thr Pro Ser Pro
30              35                  40

ACC GCC CCA GGT GGA CCA ATT TCC TTT AAA CCT GAG CGC CTC             366
Thr Ala Pro Gly Gly Pro Ile Ser Phe Lys Pro Glu Arg Leu
        45                  50                  55

CAG GCC TTA AAT GAC CTG GTC TCC AAG GCC CTG GAG GCT GGC             408
Gln Ala Leu Asn Asp Leu Val Ser Lys Ala Leu Glu Ala Gly
            60                  65                  70

CAC ATT GAA CCG TAC TCA GGA CCA GGC AAT AAC CCC GTC TTC             450
His Ile Glu Pro Tyr Ser Gly Pro Gly Asn Asn Pro Val Phe
                75                  80                  85

CCC GTT AAA AAA CCA AAT GGC AAA TGG AGG TTC ATT CAT GAC             492
Pro Val Lys Lys Pro Asn Gly Lys Trp Arg Phe Ile His Asp
                90                  95

CTA AGA GCC ACC AAC GCC ATC GCT ACC ACC CTC ACC TCT CCT             534
Leu Arg Ala Thr Asn Ala Ile Ala Thr Thr Leu Thr Ser Pro
100             105                 110

TCC CCA GGG CCC CCC GAC CTC ACT AGC CTA CCA ACA GCC TTA             576
Ser Pro Gly Pro Pro Asp Leu Thr Ser Leu Pro Thr Ala Leu
        115                 120                 125

CCC CAC CTA CAG ACC ATA GAC CTT ACT GAC GCC TTT TTC CAA             618
Pro His Leu Gln Thr Ile Asp Leu Thr Asp Ala Phe Phe Gln
            130                 135                 140

ATC CCC CTC CCC AAG CAG TTC CAG CCA TAC TTC GCC TTC ACC             660
Ile Pro Leu Pro Lys Gln Phe Gln Pro Tyr Phe Ala Phe Thr
                145                 150                 155

ATT CCC CAG CCA TGT AAT TAT GGC CCC GGG ACC AGA TAC GCA             702
Ile Pro Gln Pro Cys Asn Tyr Gly Pro Gly Thr Arg Tyr Ala
                160                 165

TGG ACT GTC CTT CCA CAG GGG TTT AAA AAC AGC CCC ACC CTC             744
Trp Thr Val Leu Pro Gln Gly Phe Lys Asn Ser Pro Thr Leu
170             175                 180

TTC GAG CAA CAA TTA GCG GCT GTC CTC AAC CCC ATG AGG AAA             786
Phe Glu Gln Gln Leu Ala Ala Val Leu Asn Pro Met Arg Lys
        185                 190                 195

ATG TTT CCC ACG TCG ACC ATT GTC CAA TAC ATG GAT GAC ATA             828
Met Phe Pro Thr Ser Thr Ile Val Gln Tyr Met Asp Asp Ile
            200                 205                 210

CTT TTG GCC AGC CCC ACC AAT AAG GAA TTA CAA CAA CTC TCC             870
Leu Leu Ala Ser Pro Thr Asn Lys Glu Leu Gln Gln Leu Ser
                215                 220                 225

CAG TTA ACC CTC CAG GCA CTG ACC ACA CAT GGC CTT CCA ATC             912
Gln Leu Thr Leu Gln Ala Leu Thr Thr His Gly Leu Pro Ile
                230                 235

TCC CAG GAA AAA ACG CAA CGT ACC CCA GGC CAG ATA CGC TTC             954
Ser Gln Glu Lys Thr Gln Arg Thr Pro Gly Gln Ile Arg Phe
240             245                 250
```

```
TTA GGA CAA GTC ATC TCC CCT AAT CAC ATT ACA TAT GAA AGT              996
Leu Gly Gln Val Ile Ser Pro Asn His Ile Thr Tyr Glu Ser
        255                 260                 265

ACC CCT GCT ATT CCC ATA AAA TCC CAA TGG ACA CTC ACT GAG             1038
Thr Pro Ala Ile Pro Ile Lys Ser Gln Trp Thr Leu Thr Glu
            270                 275                 280

CTA CAG GTT ATC CTA GGA GAA ATC CAG TGG GTC TCT AAA GGT             1080
Leu Gln Val Ile Leu Gly Glu Ile Gln Trp Val Ser Lys Gly
                285                 290                 295

ACC CCC ATC CTT CGC AAA CAC CTA CAA TCC CTA TAT TCT GCC             1122
Thr Pro Ile Leu Arg Lys His Leu Gln Ser Leu Tyr Ser Ala
                    300                 305

CTT CAC GGG TAC CGG GAC CCA AGA GCC TGT ATC ACC CTT ACA             1164
Leu His Gly Tyr Arg Asp Pro Arg Ala Cys Ile Thr Leu Thr
310                 315                 320

CCA CAA CAA CTC CAT GCG CTA CAT GCC ATC CAA CAA GCT CTA             1206
Pro Gln Gln Leu His Ala Leu His Ala Ile Gln Gln Ala Leu
        325                 330                 335

CAA CAT AAC TGC CGT GGC CGC CTC GAC CCT ACC CTA CCT CTC             1248
Gln His Asn Cys Arg Gly Arg Leu Asp Pro Thr Leu Pro Leu
            340                 345                 350

CTC GGC CTT ATC TCG TTG AGT ACA TCT GGC ACA ACA TCT GTC             1290
Leu Gly Leu Ile Ser Leu Ser Thr Ser Gly Thr Thr Ser Val
                355                 360                 365

ATC TTT CAA CCC AAG CAA AAC TGG CCC CTG GCT TGG CTC CAT             1332
Ile Phe Gln Pro Lys Gln Asn Trp Pro Leu Ala Trp Leu His
                    370                 375

ACC CCC CAC CCT CCG ACC AGT TTA TGT CCT TGG GGT CAC CTA             1374
Thr Pro His Pro Pro Thr Ser Leu Cys Pro Trp Gly His Leu
380                 385                 390

CTG GCC TGT ACC ATT CTA ACT CTA GAC AAA TAC ACC CTA CAA             1416
Leu Ala Cys Thr Ile Leu Thr Leu Asp Lys Tyr Thr Leu Gln
        395                 400                 405

CAT TAT GGC CTG CTC TGC CAA TCT TTC CAC CAC AAC ATG TCA             1458
His Tyr Gly Leu Leu Cys Gln Ser Phe His His Asn Met Ser
            410                 415                 420

AAA CAG GCC CTT TGC GAC TTC CTA AGG AAC TCC CCT CAT CCA             1500
Lys Gln Ala Leu Cys Asp Phe Leu Arg Asn Ser Pro His Pro
                425                 430                 435

AGC GTC GGC ATC CTC ATT CAC CAC ATG GGT CGC TTC CAT AAC             1542
Ser Val Gly Ile Leu Ile His His Met Gly Arg Phe His Asn
                    440                 445

CTT GGC AGT CAA CCG TCT GGC CCG TGG AAG ACT CTC TTA CAC             1584
Leu Gly Ser Gln Pro Ser Gly Pro Trp Lys Thr Leu Leu His
450                 455                 460

CTC CCA ACC CTT CTC CAG GAA CCA CGA CTC CTC AGA CCA ATT             1626
Leu Pro Thr Leu Leu Gln Glu Pro Arg Leu Leu Arg Pro Ile
        465                 470                 475

TTC ACC CTC TCC CCC GTC GTG CTT GAC ACG GCC CCC TGC CTT             1668
Phe Thr Leu Ser Pro Val Val Leu Asp Thr Ala Pro Cys Leu
            480                 485                 490

TTT TCC GAT GGC TCC CCT CAA AAG GCA GCA TAC GTC CTC TGG             1710
Phe Ser Asp Gly Ser Pro Gln Lys Ala Ala Tyr Val Leu Trp
                495                 500                 505

GAC CAG ACT ATC CTT CAA CAA GAC ATT ACT CCC CTG CCC CCT             1752
Asp Gln Thr Ile Leu Gln Gln Asp Ile Thr Pro Leu Pro Pro
                    510                 515

CAC GAA ACA AAT TCC GCA CAA AAG GGA GAA CTC CTT GCA CTT             1794
His Glu Thr Asn Ser Ala Gln Lys Gly Glu Leu Leu Ala Leu
```

```
                520                 525                 530
ATC TAT GGA CTA CGT GCT GCC AAG CCA TGG CCC TCC CTT AAT        1836
Ile Tyr Gly Leu Arg Ala Ala Lys Pro Trp Pro Ser Leu Asn
    535                 540                 545

ATC TTC TTA GAC TCT AAA TAC TTA ATC AAA TAC CTA CAC TCC        1878
Ile Phe Leu Asp Ser Lys Tyr Leu Ile Lys Tyr Leu His Ser
        550                 555                 560

CTC GCC ATT GGG GCC TTC CTC GGC ACG TCC GCC CAT CAA ACC        1920
Leu Ala Ile Gly Ala Phe Leu Gly Thr Ser Ala His Gln Thr
            565                 570                 575

CTC CAG GCG GCC TTA CCA CCC CTA CTA CAG GGC AAG ACC ATC        1962
Leu Gln Ala Ala Leu Pro Pro Leu Leu Gln Gly Lys Thr Ile
                580                 585

TAC CTC CAT CAT GTT CGT AGC CAC ACC AAT CTC CCC GAC CCA        2004
Tyr Leu His His Val Arg Ser His Thr Asn Leu Pro Asp Pro
590                 595                 600

ATT TCC ACC TTC AAT GAA TAC ACA GAC TCC CTT ATT GTA GCT        2046
Ile Ser Thr Phe Asn Glu Tyr Thr Asp Ser Leu Ile Val Ala
    605                 610                 615

CCC CTT GTC CCC CTG ACG CCC CAG GGC CTC CAC GGC CTC ACC        2088
Pro Leu Val Pro Leu Thr Pro Gln Gly Leu His Gly Leu Thr
        620                 625                 630

CAT TGC AAC CAA AGG GCT CTA GTC TCC TTT GGC GCC ACA CCA        2130
His Cys Asn Gln Arg Ala Leu Val Ser Phe Gly Ala Thr Pro
            635                 640                 645

AAG GAA GCC AAG TCC CTT GTA CAG ACT TGC CAT ACC TGT CAG        2172
Lys Glu Ala Lys Ser Leu Val Gln Thr Cys His Thr Cys Gln
                650                 655

ATC ATC AAC TCA CAA CAT CAT ATG CCT CAA GGG CAC ATT CGC        2214
Ile Ile Asn Ser Gln His His Met Pro Gln Gly His Ile Arg
660                 665                 670

CGG GGC CTC CTA CCC AAC CAC ATA TGG CAA GGT GAT GTA ACC        2256
Arg Gly Leu Leu Pro Asn His Ile Trp Gln Gly Asp Val Thr
    675                 680                 685

CAT TAT AAG TAC AAA AAA TAC AAA TAC TGC CTC CAC GTC TGG        2298
His Tyr Lys Tyr Lys Lys Tyr Lys Tyr Cys Leu His Val Trp
        690                 695                 700

GTA GAC ACC TTC TCC GGT GCG GTT TCC GTC TCC TGT AAG AAG        2340
Val Asp Thr Phe Ser Gly Ala Val Ser Val Ser Cys Lys Lys
            705                 710                 715

AAA GAA ACC AGC TGT GAG ACT ATC AGC GCC TTC CTT CAG GCC        2382
Lys Glu Thr Ser Cys Glu Thr Ile Ser Ala Phe Leu Gln Ala
                720                 725

ATC TCC CTC CTG GGA AAA CCA CTC CAC ATT AAT ACA GAT AAT        2424
Ile Ser Leu Leu Gly Lys Pro Leu His Ile Asn Thr Asp Asn
730                 735                 740

GGG CCA GCC TTC TTG TCA CAA GAA TTC CAG GAG TTT TGT ACC        2466
Gly Pro Ala Phe Leu Ser Gln Glu Phe Gln Glu Phe Cys Thr
    745                 750                 755

TCC TAT CAC ATC AAA CAT TCT ACC CAC ATA CCA TAC AAC CCC        2508
Ser Tyr His Ile Lys His Ser Thr His Ile Pro Tyr Asn Pro
        760                 765                 770

ACC AGC TCA GGC CTG GTC GAA AGG ACC AAT GGT ATA ATC AAA        2550
Thr Ser Ser Gly Leu Val Glu Arg Thr Asn Gly Ile Ile Lys
            775                 780                 785

AAT TTA CTA AAC AAA TAT CTA CTA GAT TGT CCT AAC CTT CCC        2592
Asn Leu Leu Asn Lys Tyr Leu Leu Asp Cys Pro Asn Leu Pro
                790                 795

CTA GAC AAT GCC ATT AAC AAA GCC CTC TGG ACC CTC AAT CAG        2634
```

```
Leu Asp Asn Ala Ile Asn Lys Ala Leu Trp Thr Leu Asn Gln
800                 805                 810

CTA AAT GTC ATG AAC CCC AGT GGT AAA ACC CGA TGG CAA ATC      2676
Leu Asn Val Met Asn Pro Ser Gly Lys Thr Arg Trp Gln Ile
    815                 820                 825

CAT CAC AGC CCT CCA TTG CCA CCC ATT CCT GAA GCC TCT ACC      2718
His His Ser Pro Pro Leu Pro Pro Ile Pro Glu Ala Ser Thr
                830                 835                 840

CCT CCC AAA CCA CCA TCT AAA TGG TTC TAT TAT AAA CTC CCC      2760
Pro Pro Lys Pro Pro Ser Lys Trp Phe Tyr Tyr Lys Leu Pro
            845                 850                 855

GGC CTT ACC AAT CAG CGG TGG AAA GGT CCA TTA CAA TCC CTC      2802
Gly Leu Thr Asn Gln Arg Trp Lys Gly Pro Leu Gln Ser Leu
                860                 865

CAG GAA GCG GCT GGG GCA GCC CTG CTC TCC ATA GAC GGC TTC      2844
Gln Glu Ala Ala Gly Ala Ala Leu Leu Ser Ile Asp Gly Phe
870                 875                 880

CCC CGG TGG ATC CCG TGG CGA TTC CTG AAA AAA GCT GCA TGC      2886
Pro Arg Trp Ile Pro Trp Arg Phe Leu Lys Lys Ala Ala Cys
        885                 890                 895

CCA AGA CCA GAC GCC AGC GAA CCC GCC GAG CAC GCC GCA ACA      2928
Pro Arg Pro Asp Ala Ser Glu Pro Ala Glu His Ala Ala Thr
            900                 905                 910

GAC CAC CAA CAC CAT GGG TAA                                  2949
Asp His Gln His His Gly
            915
```

(2) INFORMATION FOR SEQ ID NO:11:

(i) SEQUENCE CHARACTERISTICS:
        (A) LENGTH: 917 amino acids
        (B) TYPE: amino acid
        (C) STRANDEDNESS:
        (D) TOPOLOGY: unknown (xi) SEQUENCE DESCRIPTION: SEQ ID NO:11:

```
Met Asp His His Trp Lys Arg Arg Pro Thr Thr Met Pro Gly
                5                   10

Ala Ser Ile Pro Ser Arg Arg Ser Gln Pro Pro Ser Ile Ala
15                  20                  25

Ala Asn Ser His Ser Thr His His Arg Pro Arg Thr Pro Ser
    30                  35                  40

Pro Thr Ala Pro Gly Gly Pro Ile Ser Phe Lys Pro Glu Arg
                45                  50                  55

Leu Gln Ala Leu Asn Asp Leu Val Ser Lys Ala Leu Glu Ala
                    60                  65                  70

Gly His Ile Glu Pro Tyr Ser Gly Pro Gly Asn Asn Pro Val
                75                  80

Phe Pro Val Lys Lys Pro Asn Gly Lys Trp Arg Phe Ile His
85                  90                  95

Asp Leu Arg Ala Thr Asn Ala Ile Ala Thr Thr Leu Thr Ser
        100                 105                 110

Pro Ser Pro Gly Pro Pro Asp Leu Thr Ser Leu Pro Thr Ala
            115                 120                 125

Leu Pro His Leu Gln Thr Ile Asp Leu Thr Asp Ala Phe Phe
                130                 135                 140

Gln Ile Pro Leu Pro Lys Gln Phe Gln Pro Tyr Phe Ala Phe
                    145                 150
```

```
Thr Ile Pro Gln Pro Cys Asn Tyr Gly Pro Gly Thr Arg Tyr
155                 160                 165

Ala Trp Thr Val Leu Pro Gln Gly Phe Lys Asn Ser Pro Thr
170                 175                 180

Leu Phe Glu Gln Gln Leu Ala Ala Val Leu Asn Pro Met Arg
            185                 190                 195

Lys Met Phe Pro Thr Ser Thr Ile Val Gln Tyr Met Asp Asp
                200                 205                 210

Ile Leu Leu Ala Ser Pro Thr Asn Lys Glu Leu Gln Gln Leu
                215                 220

Ser Gln Leu Thr Leu Gln Ala Leu Thr Thr His Gly Leu Pro
225                 230                 235

Ile Ser Gln Glu Lys Thr Gln Arg Thr Pro Gly Gln Ile Arg
    240                 245                 250

Phe Leu Gly Gln Val Ile Ser Pro Asn His Ile Thr Tyr Glu
            255                 260                 265

Ser Thr Pro Ala Ile Pro Ile Lys Ser Gln Trp Thr Leu Thr
            270                 275                 280

Glu Leu Gln Val Ile Leu Gly Glu Ile Gln Trp Val Ser Lys
            285                 290

Gly Thr Pro Ile Leu Arg Lys His Leu Gln Ser Leu Tyr Ser
295                 300                 305

Ala Leu His Gly Tyr Arg Asp Pro Arg Ala Cys Ile Thr Leu
    310                 315                 320

Thr Pro Gln Gln Leu His Ala Leu His Ala Ile Gln Gln Ala
            325                 330                 335

Leu Gln His Asn Cys Arg Gly Arg Leu Asp Pro Thr Leu Pro
            340                 345                 350

Leu Leu Gly Leu Ile Ser Leu Ser Thr Ser Gly Thr Thr Ser
                355                 360

Val Ile Phe Gln Pro Lys Gln Asn Trp Pro Leu Ala Trp Leu
365                 370                 375

His Thr Pro His Pro Pro Thr Ser Leu Cys Pro Trp Gly His
    380                 385                 390

Leu Leu Ala Cys Thr Ile Leu Thr Leu Asp Lys Tyr Thr Leu
            395                 400                 405

Gln His Tyr Gly Leu Leu Cys Gln Ser Phe His His Asn Met
            410                 415                 420

Ser Lys Gln Ala Leu Cys Asp Phe Leu Arg Asn Ser Pro His
                425                 430

Pro Ser Val Gly Ile Leu Ile His Met Gly Arg Phe His
435                 440                 445

Asn Leu Gly Ser Gln Pro Ser Gly Pro Trp Lys Thr Leu Leu
    450                 455                 460

His Leu Pro Thr Leu Leu Gln Glu Pro Arg Leu Leu Arg Pro
    465                 470                 475

Ile Phe Thr Leu Ser Pro Val Val Leu Asp Thr Ala Pro Cys
            480                 485                 490

Leu Phe Ser Asp Gly Ser Pro Gln Lys Ala Ala Tyr Val Leu
            495                 500

Trp Asp Gln Thr Ile Leu Gln Gln Asp Ile Thr Pro Leu Pro
505                 510                 515

Pro His Glu Thr Asn Ser Ala Gln Lys Gly Glu Leu Leu Ala
```

```
                    520                 525                 530
Leu Ile Tyr Gly Leu Arg Ala Ala Lys Pro Trp Pro Ser Leu
            535                 540                 545

Asn Ile Phe Leu Asp Ser Lys Tyr Leu Ile Lys Tyr Leu His
            550                 555                 560

Ser Leu Ala Ile Gly Ala Phe Leu Gly Thr Ser Ala His Gln
            565                 570

Thr Leu Gln Ala Ala Leu Pro Pro Leu Leu Gln Gly Lys Thr
575                 580                 585

Ile Tyr Leu His His Val Arg Ser His Thr Asn Leu Pro Asp
            590                 595                 600

Pro Ile Ser Thr Phe Asn Glu Tyr Thr Asp Ser Leu Ile Val
            605                 610                 615

Ala Pro Leu Val Pro Leu Thr Pro Gln Gly Leu His Gly Leu
                620                 625                 630

Thr His Cys Asn Gln Arg Ala Leu Val Ser Phe Gly Ala Thr
            635                 640

Pro Lys Glu Ala Lys Ser Leu Val Gln Thr Cys His Thr Cys
645                 650                 655

Gln Ile Ile Asn Ser Gln His His Met Pro Gln Gly His Ile
            660                 665                 670

Arg Arg Gly Leu Leu Pro Asn His Ile Trp Gln Gly Asp Val
            675                 680                 685

Thr His Tyr Lys Tyr Lys Lys Tyr Lys Tyr Cys Leu His Val
            690                 695                 700

Trp Val Asp Thr Phe Ser Gly Ala Val Ser Val Ser Cys Lys
                705                 710

Lys Lys Glu Thr Ser Cys Glu Thr Ile Ser Ala Phe Leu Gln
715                 720                 725

Ala Ile Ser Leu Leu Gly Lys Pro Leu His Ile Asn Thr Asp
            730                 735                 740

Asn Gly Pro Ala Phe Leu Ser Gln Glu Phe Gln Glu Phe Cys
            745                 750                 755

Thr Ser Tyr His Ile Lys His Ser Thr His Ile Pro Tyr Asn
                760                 765                 770

Pro Thr Ser Ser Gly Leu Val Glu Arg Thr Asn Gly Ile Ile
                775                 780

Lys Asn Leu Leu Asn Lys Tyr Leu Leu Asp Cys Pro Asn Leu
785                 790                 795

Pro Leu Asp Asn Ala Ile Asn Lys Ala Leu Trp Thr Leu Asn
            800                 805                 810

Gln Leu Asn Val Met Asn Pro Ser Gly Lys Thr Arg Trp Gln
            815                 820                 825

Ile His His Ser Pro Pro Leu Pro Pro Ile Pro Glu Ala Ser
            830                 835                 840

Thr Pro Pro Lys Pro Pro Ser Lys Trp Phe Tyr Tyr Lys Leu
                845                 850

Pro Gly Leu Thr Asn Gln Arg Trp Lys Gly Pro Leu Gln Ser
855                 860                 865

Leu Gln Glu Ala Ala Gly Ala Ala Leu Leu Ser Ile Asp Gly
            870                 875                 880

Phe Pro Arg Trp Ile Pro Trp Arg Phe Leu Lys Lys Ala Ala
            885                 890                 895
```

```
Cys Pro Arg Pro Asp Ala Ser Glu Pro Ala Glu His Ala Ala
        900                 905                 910

Thr Asp His Gln His His Gly
                915

(2) INFORMATION FOR SEQ ID NO:12:

(i) SEQUENCE CHARACTERISTICS:
        (A) LENGTH: 1461 base pairs
        (B) TYPE: nucleic acid
        (C) STRANDEDNESS: single stranded
        (D) TOPOLOGY: linear (xi) SEQUENCE DESCRIPTION: SEQ ID NO:12:

ATG GGT AAC GTT TTC TTC CTA CTT TTA TTC AGT CTC ACA CAC              42
Met Gly Asn Val Phe Phe Leu Leu Leu Phe Ser Leu Thr His
                  5                  10

TTC CCA CCA GTC CAG CAG AGC CGA TGC ACA CTC ACG GTT GGT              84
Phe Pro Pro Val Gln Gln Ser Arg Cys Thr Leu Thr Val Gly
 15                  20                  25

ATT TCC TCC TAC CAC TCC AGC CCC TGT AGC CCA ACC CAA CCC             126
Ile Ser Ser Tyr His Ser Ser Pro Cys Ser Pro Thr Gln Pro
     30                  35                  40

GTC TGC ACG TGG AAC CTC GAC CTT AAT TCC CTA ACG ACG GAC             168
Val Cys Thr Trp Asn Leu Asp Leu Asn Ser Leu Thr Thr Asp
             45                  50                  55

CAG CGA CTA CAT CCC CCC TGC CCT AAC CTA ATT ACT TAC TCT             210
Gln Arg Leu His Pro Pro Cys Pro Asn Leu Ile Thr Tyr Ser
                 60                  65                  70

GGC TTC CAC AAA ACT TAT TCC TTA TAC TTA TTC CCA CAT TGG             252
Gly Phe His Lys Thr Tyr Ser Leu Tyr Leu Phe Pro His Trp
                     75                  80

ATA AAG AAG CCA AAT AGA CAG GGC CTA GGA TAC TAC TCG CCC             294
Ile Lys Lys Pro Asn Arg Gln Gly Leu Gly Tyr Tyr Ser Pro
 85                  90                  95

TCC TAT AAT GAC CCT TGC TCG CTA CAA TGC CCC TAC TTA GGC             336
Ser Tyr Asn Asp Pro Cys Ser Leu Gln Cys Pro Tyr Leu Gly
    100                 105                 110

TGC CAA TCA TGG ACA TGC CCA TAC ACG GGC CCC GTC TCC AGT             378
Cys Gln Ser Trp Thr Cys Pro Tyr Thr Gly Pro Val Ser Ser
            115                 120                 125

CCA TCC TGG AAG TTT CAC TCA GAT GTA AAT TTC ACC CAA GAA             420
Pro Ser Trp Lys Phe His Ser Asp Val Asn Phe Thr Gln Glu
                130                 135                 140

GTC AGC CAA GTG TCC CTT CGA CTA CAC TTC TCT AAG TGC GGC             462
Val Ser Gln Val Ser Leu Arg Leu His Phe Ser Lys Cys Gly
                    145                 150

TCC TCC ATG ACC CTT CTA GTA GAT GCC CCT GGA TAT GAT CCT             504
Ser Ser Met Thr Leu Leu Val Asp Ala Pro Gly Tyr Asp Pro
155                 160                 165

TTA TGG TTC ATC ACC TCA GAA CCC ACT CAG CCT CCC CCA ACT             546
Leu Trp Phe Ile Thr Ser Glu Pro Thr Gln Pro Pro Pro Thr
        170                 175                 180

CCT CCC CCA CTG GTC CAT GAC TCC GAC CTT GAA CAC GTC CTA             588
Pro Pro Pro Leu Val His Asp Ser Asp Leu Glu His Val Leu
                185                 190                 195

ACC CCC TCC ACG TCT TGG ACA ACC AAA ATG CTC AAG TTT ATC             630
Thr Pro Ser Thr Ser Trp Thr Thr Lys Met Leu Lys Phe Ile
                    200                 205                 210

CAG CTG ACC TTG CAG AGC ACC AAT TAC TCC TGC ATG GTT TGC             672
```

```
Gln Leu Thr Leu Gln Ser Thr Asn Tyr Ser Cys Met Val Cys
            215                 220

GTG GAT AGA TCC AGC CTC TCA TCC TGG CAT GTG CTC TAC ACC         714
Val Asp Arg Ser Ser Leu Ser Ser Trp His Val Leu Tyr Thr
225             230                 235

CCC AAC ATC TCC ATT CCC CAA CAA ACC TCC TCC CGA ACC ATC         756
Pro Asn Ile Ser Ile Pro Gln Gln Thr Ser Ser Arg Thr Ile
        240                 245                 250

CTC TTT CCT TCT CTT GCC CTG CCC GCT CCT CCA TTC CAA CCC         798
Leu Phe Pro Ser Leu Ala Leu Pro Ala Pro Pro Phe Gln Pro
            255                 260                 265

TTC CCT TGG ACC CAT TGC TAC CAA CCT CGC CTA CAG GCA ATA         840
Phe Pro Trp Thr His Cys Tyr Gln Pro Arg Leu Gln Ala Ile
                270                 275                 280

ACG ACA GAT GAC TGC AAC AAC TCC ATT ATC CTC CCC CCT TTT         882
Thr Thr Asp Asp Cys Asn Asn Ser Ile Ile Leu Pro Pro Phe
                    285                 290

TCC CTC GCC CCC GTA CCT CCT CCG GCG ACA AGA CGC CGC CGT         924
Ser Leu Ala Pro Val Pro Pro Pro Ala Thr Arg Arg Arg Arg
295             300                 305

GCC GTT CCA ATA GCA GTG TGG CTT GTC TCC GCT CTA GCG GCC         966
Ala Val Pro Ile Ala Val Trp Leu Val Ser Ala Leu Ala Ala
        310                 315                 320

GGG ACA GGT ATC GCT GGC GGA GTA ACA GGC TCC CTA TCT CTA        1008
Gly Thr Gly Ile Ala Gly Gly Val Thr Gly Ser Leu Ser Leu
            325                 330                 335

GCT TCC AGT AAA AGC CTT CTC TTC GAG GTT GAC AAA GAT ATC        1050
Ala Ser Ser Lys Ser Leu Leu Phe Glu Val Asp Lys Asp Ile
                340                 345                 350

TCC CAC CTT ACC CAG GCC ATA GTC AAA AAT CAT CAA AAC ATC        1092
Ser His Leu Thr Gln Ala Ile Val Lys Asn His Gln Asn Ile
                    355                 360

CTC CGG GTT GCA CAA TAT GCA GCC CAG AAT AGA CGA GGA TTA        1134
Leu Arg Val Ala Gln Tyr Ala Ala Gln Asn Arg Arg Gly Leu
365             370                 375

GAC CTC CTA TTC TGG GAA CAA GGG GGT TTG TGC AAA GCC ATA        1176
Asp Leu Leu Phe Trp Glu Gln Gly Gly Leu Cys Lys Ala Ile
        380                 385                 390

CAG GAG CAA TGT TGC TTC CTC AAT ATC AGT AAC ACT CAT GTA        1218
Gln Glu Gln Cys Cys Phe Leu Asn Ile Ser Asn Thr His Val
            395                 400                 405

TCC GTC CTC CAA GAA CGG CCC CCT CTT GAA AAG CGT GTC ATC        1260
Ser Val Leu Gln Glu Arg Pro Pro Leu Glu Lys Arg Val Ile
                410                 415                 420

ACC GGT TGG GGA CTA AAC TGG GAT CTT GGT CTG TCC CAG TGG        1302
Thr Gly Trp Gly Leu Asn Trp Asp Leu Gly Leu Ser Gln Trp
                    425                 430

GCA CGA GAA GCC CTC CAG ACA GGC ATA ACC ATT CTC ACC CTA        1344
Ala Arg Glu Ala Leu Gln Thr Gly Ile Thr Ile Leu Thr Leu
435             440                 445

CTC CTC CTT GTC ATA TTG TTT GGC CCC TGC ATC CTC CGC CAA        1386
Leu Leu Leu Val Ile Leu Phe Gly Pro Cys Ile Leu Arg Gln
        450                 455                 460

ATC CAA GCC CTT CCG CAG CGG TTA CAA AAC CGA CAT AGC CAG        1428
Ile Gln Ala Leu Pro Gln Arg Leu Gln Asn Arg His Ser Gln
            465                 470                 475

TAT GCC CTT ATC AAC CAA GAG ACC ATG CTA TAA                    1461
Tyr Ala Leu Ile Asn Gln Glu Thr Met Leu
                480                 485
```

(2) INFORMATION FOR SEQ ID NO:13:

(i) SEQUENCE CHARACTERISTICS:
        (A) LENGTH: 486 amino acids
        (B) TYPE: amino acid
        (C) STRANDEDNESS:
        (D) TOPOLOGY: unknown (xi) SEQUENCE DESCRIPTION: SEQ ID NO:13:

```
Met Gly Asn Val Phe Phe Leu Leu Phe Ser Leu Thr His
                  5                  10

Phe Pro Pro Val Gln Gln Ser Arg Cys Thr Leu Thr Val Gly
 15              20                  25

Ile Ser Ser Tyr His Ser Ser Pro Cys Ser Pro Thr Gln Pro
 30                  35                  40

Val Cys Thr Trp Asn Leu Asp Leu Asn Ser Leu Thr Thr Asp
             45              50                  55

Gln Arg Leu His Pro Pro Cys Pro Asn Leu Ile Thr Tyr Ser
                 60              65                  70

Gly Phe His Lys Thr Tyr Ser Leu Tyr Leu Phe Pro His Trp
             75                  80

Ile Lys Lys Pro Asn Arg Gln Gly Leu Gly Tyr Tyr Ser Pro
 85              90                  95

Ser Tyr Asn Asp Pro Cys Ser Leu Gln Cys Pro Tyr Leu Gly
100                 105                 110

Cys Gln Ser Trp Thr Cys Pro Tyr Thr Gly Pro Val Ser Ser
            115                 120                 125

Pro Ser Trp Lys Phe His Ser Asp Val Asn Phe Thr Gln Glu
            130                 135                 140

Val Ser Gln Val Ser Leu Arg Leu His Phe Ser Lys Cys Gly
                145                 150

Ser Ser Met Thr Leu Leu Val Asp Ala Pro Gly Tyr Asp Pro
155                 160                 165

Leu Trp Phe Ile Thr Ser Glu Pro Thr Gln Pro Pro Pro Thr
170                 175                 180

Pro Pro Pro Leu Val His Asp Ser Asp Leu Glu His Val Leu
            185                 190                 195

Thr Pro Ser Thr Ser Trp Thr Thr Lys Met Leu Lys Phe Ile
                200                 205                 210

Gln Leu Thr Leu Gln Ser Thr Asn Tyr Ser Cys Met Val Cys
                215                 220

Val Asp Arg Ser Ser Leu Ser Ser Trp His Val Leu Tyr Thr
225                 230                 235

Pro Asn Ile Ser Ile Pro Gln Gln Thr Ser Ser Arg Thr Ile
240                 245                 250

Leu Phe Pro Ser Leu Ala Leu Pro Ala Pro Phe Gln Pro
            255                 260                 265

Phe Pro Trp Thr His Cys Tyr Gln Pro Arg Leu Gln Ala Ile
            270                 275                 280

Thr Thr Asp Asp Cys Asn Asn Ser Ile Ile Leu Pro Pro Phe
                285                 290

Ser Leu Ala Pro Val Pro Pro Ala Thr Arg Arg Arg Arg
295                 300                 305

Ala Val Pro Ile Ala Val Trp Leu Val Ser Ala Leu Ala Ala
310                 315                 320
```

```
Gly Thr Gly Ile Ala Gly Gly Val Thr Gly Ser Leu Ser Leu
            325                 330                 335

Ala Ser Ser Lys Ser Leu Leu Phe Glu Val Asp Lys Asp Ile
            340                 345                 350

Ser His Leu Thr Gln Ala Ile Val Lys Asn His Gln Asn Ile
            355                 360

Leu Arg Val Ala Gln Tyr Ala Ala Gln Asn Arg Arg Gly Leu
365                 370                 375

Asp Leu Leu Phe Trp Glu Gln Gly Gly Leu Cys Lys Ala Ile
        380                 385                 390

Gln Glu Gln Cys Cys Phe Leu Asn Ile Ser Asn Thr His Val
            395                 400                 405

Ser Val Leu Gln Glu Arg Pro Pro Leu Glu Lys Arg Val Ile
            410                 415                 420

Thr Gly Trp Gly Leu Asn Trp Asp Leu Gly Leu Ser Gln Trp
                    425                 430

Ala Arg Glu Ala Leu Gln Thr Gly Ile Thr Ile Leu Thr Leu
435                 440                 445

Leu Leu Leu Val Ile Leu Phe Gly Pro Cys Ile Leu Arg Gln
            450                 455                 460

Ile Gln Ala Leu Pro Gln Arg Leu Gln Asn Arg His Ser Gln
            465                 470                 475

Tyr Ala Leu Ile Asn Gln Glu Thr Met Leu
                480                 485

(2) INFORMATION FOR SEQ ID NO:14:

(i) SEQUENCE CHARACTERISTICS:
        (A) LENGTH: 537 base pairs
        (B) TYPE: nucleic acid
        (C) STRANDEDNESS: single stranded
        (D) TOPOLOGY: linear (xi) SEQUENCE DESCRIPTION: SEQ ID NO:14:

GCC GTT CCA ATA GCA GTG TGG CTT GTC TCC GCT CTA GCG GCC            42
Ala Val Pro Ile Ala Val Trp Leu Val Ser Ala Leu Ala Ala
            5                   10

GGG ACA GGT ATC GCT GGC GGA GTA ACA GGC TCC CTA TCT CTA            84
Gly Thr Gly Ile Ala Gly Gly Val Thr Gly Ser Leu Ser Leu
15                  20                  25

GCT TCC AGT AAA AGC CTT CTC TTC GAG GTT GAC AAA GAT ATC           126
Ala Ser Ser Lys Ser Leu Leu Phe Glu Val Asp Lys Asp Ile
        30                  35                  40

TCC CAC CTT ACC CAG GCC ATA GTC AAA AAT CAT CAA AAC ATC           168
Ser His Leu Thr Gln Ala Ile Val Lys Asn His Gln Asn Ile
            45                  50                  55

CTC CGG GTT GCA CAA TAT GCA GCC CAG AAT AGA CGA GGA TTA           210
Leu Arg Val Ala Gln Tyr Ala Ala Gln Asn Arg Arg Gly Leu
            60                  65                  70

GAC CTC CTA TTC TGG GAA CAA GGG GGT TTG TGC AAA GCC ATA           252
Asp Leu Leu Phe Trp Glu Gln Gly Gly Leu Cys Lys Ala Ile
                    75                  80

CAG GAG CAA TGT TGC TTC CTC AAT ATC AGT AAC ACT CAT GTA           294
Gln Glu Gln Cys Cys Phe Leu Asn Ile Ser Asn Thr His Val
85                  90                  95

TCC GTC CTC CAA GAA CGG CCC CCT CTT GAA AAG CGT GTC ATC           336
Ser Val Leu Gln Glu Arg Pro Pro Leu Glu Lys Arg Val Ile
            100                 105                 110
```

```
ACC GGT TGG GGA CTA AAC TGG GAT CTT GGT CTG TCC CAG TGG              378
Thr Gly Trp Gly Leu Asn Trp Asp Leu Gly Leu Ser Gln Trp
        115                 120                 125

GCA CGA GAA GCC CTC CAG ACA GGC ATA ACC ATT CTC ACC CTA              420
Ala Arg Glu Ala Leu Gln Thr Gly Ile Thr Ile Leu Thr Leu
            130                 135                 140

CTC CTC CTT GTC ATA TTG TTT GGC CCC TGC ATC CTC CGC CAA              462
Leu Leu Leu Val Ile Leu Phe Gly Pro Cys Ile Leu Arg Gln
                145                 150

ATC CAA GCC CTT CCG CAG CGG TTA CAA AAC CGA CAT AGC CAG              504
Ile Gln Ala Leu Pro Gln Arg Leu Gln Asn Arg His Ser Gln
155             160                 165

TAT GCC CTT ATC AAC CAA GAG ACC ATG CTA TAA                          537
Tyr Ala Leu Ile Asn Gln Glu Thr Met Leu
170                 175
```

(2) INFORMATION FOR SEQ ID NO:15:

(i) SEQUENCE CHARACTERISTICS:
        (A) LENGTH: 178 amino acids
        (B) TYPE: amino acid
        (C) STRANDEDNESS:
        (D) TOPOLOGY: unknown (xi) SEQUENCE DESCRIPTION: SEQ ID NO:15:

```
Ala Val Pro Ile Ala Val Trp Leu Val Ser Ala Leu Ala Ala
            5                   10

Gly Thr Gly Ile Ala Gly Val Thr Gly Ser Leu Ser Leu
15          20                  25

Ala Ser Ser Lys Ser Leu Leu Phe Glu Val Asp Lys Asp Ile
    30                  35                  40

Ser His Leu Thr Gln Ala Ile Val Lys Asn His Gln Asn Ile
        45                  50                  55

Leu Arg Val Ala Gln Tyr Ala Ala Gln Asn Arg Arg Gly Leu
            60                  65                  70

Asp Leu Leu Phe Trp Glu Gln Gly Gly Leu Cys Lys Ala Ile
                75                  80

Gln Glu Gln Cys Cys Phe Leu Asn Ile Ser Asn Thr His Val
85                  90                  95

Ser Val Leu Gln Glu Arg Pro Pro Leu Glu Lys Arg Val Ile
    100                 105                 110

Thr Gly Trp Gly Leu Asn Trp Asp Leu Gly Leu Ser Gln Trp
        115                 120                 125

Ala Arg Glu Ala Leu Gln Thr Gly Ile Thr Ile Leu Thr Leu
            130                 135                 140

Leu Leu Leu Val Ile Leu Phe Gly Pro Cys Ile Leu Arg Gln
                145                 150

Ile Gln Ala Leu Pro Gln Arg Leu Gln Asn Arg His Ser Gln
155             160                 165

Tyr Ala Leu Ile Asn Gln Glu Thr Met Leu
    170                 175
```

(2) INFORMATION FOR SEQ ID NO:16:

(i) SEQUENCE CHARACTERISTICS:
        (A) LENGTH: 3100 base pairs
        (B) TYPE: nucleic acid
        (C) STRANDEDNESS: single stranded
        (D) TOPOLOGY: linear (xi) SEQUENCE DESCRIPTION: SEQ ID NO:16:

```
ATG G GTAACGTTTT CTTCCTACTT TTATTCAGTC TCACACACTT            44
Met
CCCACCAGTC CAGCAGAGCC GATGCACACT CACGGTTGGT ATTTCCTCCT       94
ACCACTCCAG CCCCTGTAGC CCAACCCAAC CCGTCTGCAC GTGGAACCTC      144
GACCTTAATT CCCTAACGAC GGACCAGCGA CTACATCCCC CCTGCCCTAA      194
CCTAATTACT TACTCTGGCT TCCACAAAAC TTATTCCTTA TACTTATTCC      244
CACATTGGAT AAAGAAGCCA AATAGACAGG GCCTAGGATA CTACTCGCCC      294
TCCTATAATG ACCCTTGCTC GCTACAATGC CCCTACTTAG GCTGCCAATC      344
ATGGACATGC CCATACACGG GCCCCGTCTC CAGTCCATCC TGGAAGTTTC      394
ACTCAGATGT AAATTTCACC CAAGAAGTCA GCCAAGTGTC CCTTCGACTA      444
CACTTCTCTA AGTGCGGCTC CTCCATGACC CTTCTAGTAG ATGCCCCTGG      494
ATATGATCCT TTATGGTTCA TCACCTCAGA ACCCACTCAG CCTCCCCCAA      544
CTCCTCCCCC ACTGGTCCAT GACTCCGACC TTGAACACGT CCTAACCCCC      594
TCCACGTCTT GGACAACCAA AATGCTCAAG TTTATCCAGC TGACCTTGCA      644
GAGCACCAAT TACTCCTGCA TGGTTTGCGT GGATAGATCC AGCCTCTCAT      694
CCTGGCATGT GCTCTACACC CCCAACATCT CCATTCCCCA ACAAACCTCC      744
TCCCGAACCA TCCTCTTTCC TTCTCTTGCC CTGCCCGCTC CTCCATTCCA      794
ACCCTTCCCT TGGACCCATT GCTACCAACC TCGCCTACAG GCAATAACGA      844
CAGATGACTG CAACAACTCC ATTATCCTCC CCCTTTTTC CCTCGCCCCC       894
GTACCTCCTC CGGCGACAAG ACGCCGCCGT GCCGTTCCAA TAGCAGTGTG      944
GCTTGTCTCC GCTCTAGCGG CCGGGACAGG TATCGCTGGC GGAGTAACAG      994
GCTCCCTATC TCTAGCTTCC AGTAAAAGCC TTCTCTTCGA GGTTGACAAA     1044
GATATCTCCC ACCTTACCCA GGCCATAGTC AAAAATCATC AAAACATCCT     1094
CCGGGTTGCA CAATATGCAG CCCAGAATAG ACGAGGATTA GACCTCCTAT     1144
TCTGGGAACA AGGGGGTTTG TGCAAAGCCA TACAGGAGCA ATGTTGCTTC     1194
CTCAATATCA GTAACACTCA TGTATCCGTC CTCCAAGAAC GGCCCCCTCT     1244
TGAAAAGCGT GTCATCACCG GTTGGGGACT AAACTGGGAT CTTGGTCTGT     1294
CCCAGTGGGC ACGAGAAGCC CTCCAGACAG GCATAACCAT TCTCACCCTA     1344
CTCCTCCTTG TCATATTGTT TGGCCCCTGC ATCCTCCGCC AAATCCAAGC     1394
CCTTCCGCAG CGGTTACAAA ACCGACATAG CCAGTATGCC CTTATCAACC     1444
AAGAGACCAT GCTATAATAG ACCCGCTAGC TTCTGCAGCA AATCCCCATG     1494
GTTCATCCCC CTACCATTGA CCCATCCACA GTCTTCTATG CCAGATGAGT     1544
CACCCCCGAT GTCCAGCCCC GACTCAAACT CAATAATTGC CTCAAATAGC     1594
TCCTCCAACC CCCGCTCACA TTCCTCCCAT AGGGCCTTTT TTTCCTCTTC     1644
CAAGAAATCC ACATAACCCT GAAGCAAATC ACAAAACCCA TCAAAACCCA     1694
GGAGTCCTAT ACACTCCAAC TGCTGATGCC TCTCTTCCCT CTCCCGGCGC     1744
TTTTGATCCT TTTCCCGCAG GCGCTCCTTT CTGCGCCGCT CCCGCTCCTC     1794
ACGCTCCTGC AGAAGCTTTA AGATCTCCCG CTGCTCCTCC GCCAACAGCT     1844
TCCGACGAGA GTCTCGCACC TGCTCGCTGA CCGATCCCGA CCCCAGAGGG     1894
```

```
CGGCCTTTTG CTGTCCTTCT TGGTTCCTCT CCAGGGGGAG GCACATCAGA              1944

TGTCAGACTC TCCTCCCCCT GGTCTCCTAA CGGCAATCTC CTAAAATAGT              1994

CTAAAAATTA CACATAATTA CAACCCTGTC TCCTCTCAG CC CAT TTC               2041
                                            Ala His Phe

CCA GGA TTC GGA CAG AGC CTC CTA TAT GGA TAC CCC GTC TAC             2083
Pro Gly Phe Gly Gln Ser Leu Leu Tyr Gly Tyr Pro Val Tyr
 5               10                  15

GTG TTT GGC GAT TGT GTA CAG GCC GAT TGG TGT CCC GTC TCA             2125
Val Phe Gly Asp Cys Val Gln Ala Asp Trp Cys Pro Val Ser
     20              25                  30

GGT GGT CTA TGT TCC ACC CGC CTA CAT CGA CAT GCC CTC CTG             2167
Gly Gly Leu Cys Ser Thr Arg Leu His Arg His Ala Leu Leu
         35              40                  45

GCC ACC TGT CCA GAG CAC CAG CTC ACC TGG GAC CCC ATC GAT             2209
Ala Thr Cys Pro Glu His Gln Leu Thr Trp Asp Pro Ile Asp
             50              55                  60

GGA CGC GTT GTC AGC TCT CCT CTC CAA TAC CTT ATC CCT CGC             2251
Gly Arg Val Val Ser Ser Pro Leu Gln Tyr Leu Ile Pro Arg
                 65              70

CTC CCC TCC TTC CCC ACC CAG AGA ACC GCC AAG ACC CTC AAG             2293
Leu Pro Ser Phe Pro Thr Gln Arg Thr Ala Lys Thr Leu Lys
75               80                  85

GTC CTT ACC CCT CCC ACC ACT CCT GTC TCC CCC AAG GTT CCA             2335
Val Leu Thr Pro Pro Thr Thr Pro Val Ser Pro Lys Val Pro
     90              95                  100

CCC GCC TTC TTC CAA TCA ATG CGA AAG CAC ACC CCC TAT CGC             2377
Pro Ala Phe Phe Gln Ser Met Arg Lys His Thr Pro Tyr Arg
         105             110                 115

AAT GGA TGC CTG GAA CCA ACC CTC GGG GAT CAG CTC CCC TCC             2419
Asn Gly Cys Leu Glu Pro Thr Leu Gly Asp Gln Leu Pro Ser
             120             125                 130

CTC GCC TTC CCT GAA CCT GGC CTC CGT CCC CAA AAC ATC TAC             2461
Leu Ala Phe Pro Glu Pro Gly Leu Arg Pro Gln Asn Ile Tyr
                 135             140

ACC ACC TGG GGA AAA ACC GTA GTG TGC CTG TAC CTA TTC CAG             2503
Thr Thr Trp Gly Lys Thr Val Val Cys Leu Tyr Leu Phe Gln
145              150                 155

CTT TCC CCA CCC ATG ACC TGG CCA CTT ATA CCC CAT GTC ATA             2545
Leu Ser Pro Pro Met Thr Trp Pro Leu Ile Pro His Val Ile
     160             165                 170

TTC TGC CAC CCA AGA CAA TTG GGA GCC TTC CTC ACC AAG GTG             2587
Phe Cys His Pro Arg Gln Leu Gly Ala Phe Leu Thr Lys Val
         175             180                 185

CCT CTA AAA CGA CTA GAA GAA CTT CTA TAC AAA ATG TTC CTA             2629
Pro Leu Lys Arg Leu Glu Glu Leu Leu Tyr Lys Met Phe Leu
             190             195                 200

CAC ACA GGA GCG GTC ATA GTC CTC CCG GAG GAC GAC CTA CCC             2671
His Thr Gly Ala Val Ile Val Leu Pro Glu Asp Asp Leu Pro
                 205             210

ACC ACA ATG TTC CAG CCC GTA AGG GCT CCC TGT ATC CAG ACT             2713
Thr Thr Met Phe Gln Pro Val Arg Ala Pro Cys Ile Gln Thr
215              220                 225

GCC TGG TGT ACA GGA CTT CTC CCC TAT CAC TCC ATC CTA ACA             2755
Ala Trp Cys Thr Gly Leu Leu Pro Tyr His Ser Ile Leu Thr
     230             235                 240

ACC CCA GGC CTA ATA TGG ACC TTC AAC GAT GGC TCA CCA ATG             2797
Thr Pro Gly Leu Ile Trp Thr Phe Asn Asp Gly Ser Pro Met
         245             250                 255
```

```
ATT TCC GGC CCT TGC CCT AAG GCA GGG CAG CCA TCT TTA GTA        2839
Ile Ser Gly Pro Cys Pro Lys Ala Gly Gln Pro Ser Leu Val
            260                 265                 270

GTT CAA TCC TCT CTA TTA ATC TTC GAA AAA TTC CAA ACC AAA        2881
Val Gln Ser Ser Leu Leu Ile Phe Glu Lys Phe Gln Thr Lys
                275                 280

GCC TTC CAT CCC TCT TAT CTA CTC TCT CAT CAA CTT ATA CAA        2923
Ala Phe His Pro Ser Tyr Leu Leu Ser His Gln Leu Ile Gln
285                 290                 295

TAC TCC TCC TTC CAT AAC CTT CAC CTC CTA TTC GAC GAG TAC        2965
Tyr Ser Ser Phe His Asn Leu His Leu Leu Phe Asp Glu Tyr
    300                 305                 310

ACC AAC ATC CCT GTC TCT ATT TTA TTT AAT AAA GAA GAG GCG        3007
Thr Asn Ile Pro Val Ser Ile Leu Phe Asn Lys Glu Glu Ala
        315                 320                 325

GAT GAC AAT GGC GAC CAG CCT CCT GAG CCA GCC GCC CAG GGC        3049
Asp Asp Asn Gly Asp Gln Pro Pro Glu Pro Ala Ala Gln Gly
            330                 335                 340

GAG TCA TCG ACC CAA AAG GTC AGA CCG TCT CAC ACA AAC AAT        3091
Glu Ser Ser Thr Gln Lys Val Arg Pro Ser His Thr Asn Asn
                345                 350

CCC AAG TAA                                                    3100
Pro Lys
355

(2) INFORMATION FOR SEQ ID NO:17:

(i) SEQUENCE CHARACTERISTICS:
        (A) LENGTH: 356 amino acids
        (B) TYPE: amino acid
        (C) STRANDEDNESS:
        (D) TOPOLOGY: unknown (xi) SEQUENCE DESCRIPTION: SEQ ID NO:17:

Met Ala His Phe Pro Gly Phe Gly Gln Ser Leu Leu Tyr Gly
                5                   10

Tyr Pro Val Tyr Val Phe Gly Asp Cys Val Gln Ala Asp Trp
15                  20                  25

Cys Pro Val Ser Gly Gly Leu Cys Ser Thr Arg Leu His Arg
        30                  35                  40

His Ala Leu Leu Ala Thr Cys Pro Glu His Gln Leu Thr Trp
                45                  50                  55

Asp Pro Ile Asp Gly Arg Val Val Ser Ser Pro Leu Gln Tyr
                    60                  65                  70

Leu Ile Pro Arg Leu Pro Ser Phe Pro Thr Gln Arg Thr Ala
                    75                  80

Lys Thr Leu Lys Val Leu Thr Pro Pro Thr Thr Pro Val Ser
85                  90                  95

Pro Lys Val Pro Pro Ala Phe Phe Gln Ser Met Arg Lys His
        100                 105                 110

Thr Pro Tyr Arg Asn Gly Cys Leu Glu Pro Thr Leu Gly Asp
                115                 120                 125

Gln Leu Pro Ser Leu Ala Phe Pro Glu Pro Gly Leu Arg Pro
                    130                 135                 140

Gln Asn Ile Tyr Thr Thr Trp Gly Lys Thr Val Val Cys Leu
                    145                 150

Tyr Leu Phe Gln Leu Ser Pro Pro Met Thr Trp Pro Leu Ile
155                 160                 165
```

```
Pro His Val Ile Phe Cys His Pro Arg Gln Leu Gly Ala Phe
    170                 175                 180

Leu Thr Lys Val Pro Leu Lys Arg Leu Glu Glu Leu Leu Tyr
        185                 190                 195

Lys Met Phe Leu His Thr Gly Ala Val Ile Val Leu Pro Glu
            200                 205                 210

Asp Asp Leu Pro Thr Thr Met Phe Gln Pro Val Arg Ala Pro
                215                 220

Cys Ile Gln Thr Ala Trp Cys Thr Gly Leu Leu Pro Tyr His
225                 230                 235

Ser Ile Leu Thr Thr Pro Gly Leu Ile Trp Thr Phe Asn Asp
    240                 245                 250

Gly Ser Pro Met Ile Ser Gly Pro Cys Pro Lys Ala Gly Gln
        255                 260                 265

Pro Ser Leu Val Val Gln Ser Ser Leu Ile Phe Glu Lys
            270                 275                 280

Phe Gln Thr Lys Ala Phe His Pro Ser Tyr Leu Leu Ser His
                285                 290

Gln Leu Ile Gln Tyr Ser Ser Phe His Asn Leu His Leu Leu
295                 300                 305

Phe Asp Glu Tyr Thr Asn Ile Pro Val Ser Ile Leu Phe Asn
    310                 315                 320

Lys Glu Glu Ala Asp Asp Asn Gly Asp Gln Pro Pro Glu Pro
        325                 330                 335

Ala Ala Gln Gly Glu Ser Ser Thr Gln Lys Val Arg Pro Ser
            340                 345                 350

His Thr Asn Asn Pro Lys
                355

(2) INFORMATION FOR SEQ ID NO:18:

(i) SEQUENCE CHARACTERISTICS:
        (A) LENGTH: 2542 base pairs
        (B) TYPE: nucleic acid
        (C) STRANDEDNESS: single stranded
        (D) TOPOLOGY: linear (xi) SEQUENCE DESCRIPTION: SEQ ID NO:18:

ATG CCC AAG ACC AGA CGC CAG CGA ACC CGC CGA GCA CGC CGC              42
Met Pro Lys Thr Arg Arg Gln Arg Thr Arg Arg Ala Arg Arg
                5                   10

AAC AGA CCA CCA ACA CCA TGG GTAACGTTTT CTTCCTACTT                    83
Asn Arg Pro Pro Thr Pro Trp
 15              20

TTATTCAGTC TCACACACTT CCCACCAGTC CAGCAGAGCC GATGCACACT              133

CACGGTTGGT ATTTCCTCCT ACCACTCCAG CCCCTGTAGC CCAACCCAAC              183

CCGTCTGCAC GTGGAACCTC GACCTTAATT CCCTAACGAC GGACCAGCGA              233

CTACATCCCC CCTGCCCTAA CCTAATTACT TACTCTGGCT TCCACAAAAC              283

TTATTCCTTA TACTTATTCC CACATTGGAT AAAGAAGCCA AATAGACAGG              333

GCCTAGGATA CTACTCGCCC TCCTATAATG ACCCTTGCTC GCTACAATGC              383

CCCTACTTAG GCTGCCAATC ATGGACATGC CCATACACGG GCCCCGTCTC              433

CAGTCCATCC TGGAAGTTTC ACTCAGATGT AAATTTCACC CAAGAAGTCA              483

GCCAAGTGTC CCTTCGACTA CACTTCTCTA AGTGCGGCTC CTCCATGACC              533
```

```
CTTCTAGTAG ATGCCCCTGG ATATGATCCT TTATGGTTCA TCACCTCAGA         583
ACCCACTCAG CCTCCCCCAA CTCCTCCCCC ACTGGTCCAT GACTCCGACC         633
TTGAACACGT CCTAACCCCC TCCACGTCTT GGACAACCAA AATGCTCAAG         683
TTTATCCAGC TGACCTTGCA GAGCACCAAT TACTCCTGCA TGGTTTGCGT         733
GGATAGATCC AGCCTCTCAT CCTGGCATGT GCTCTACACC CCCAACATCT         783
CCATTCCCCA ACAAACCTCC TCCCGAACCA TCCTCTTTCC TTCTCTTGCC         833
CTGCCCGCTC CTCCATTCCA ACCCTTCCCT TGGACCCATT GCTACCAACC         883
TCGCCTACAG GCAATAACGA CAGATGACTG CAACAACTCC ATTATCCTCC         933
CCCCTTTTTC CCTCGCCCCC GTACCTCCTC CGGCGACAAG ACGCCGCCGT         983
GCCGTTCCAA TAGCAGTGTG GCTTGTCTCC GCTCTAGCGG CCGGGACAGG        1033
TATCGCTGGC GGAGTAACAG GCTCCCTATC TCTAGCTTCA AGTAAAAGCC        1083
TTCTCTTCGA GGTTGACAAA GATATCTCCC ACCTTACCCA GGCCATAGTC        1133
AAAAATCATC AAAACATCCT CCGGGTTGCA CAATATGCAG CCCAGAATAG        1183
ACGAGGATTA GACCTCCTAT TCTGGGAACA AGGGGGTTTG TGCAAAGCCA        1233
TACAGGAGCA ATGTTGCTTC CTCAATATCA GTAACACTCA TGTATCCGTC        1283
CTCCAAGAAC GGCCCCCTCT TGAAAAGCGT GTCATCACCG GTTGGGGACT        1333
AAACTGGGAT CTTGGTCTGT CCCAGTGGGC ACGAGAAGCC CTCCAGACAG        1383
GCATAACCAT TCTCACCCTA CTCCTCCTTG TCATATTGTT TGGCCCCTGC        1433
ATCCTCCGCC AAATCCAAGC CCTTCCGCAG CGGTTACAAA ACCGACATAG        1483
CCAGTATGCC CTTATCAACC AAGAGACCAT GCTATAATAG ACCCGCTAGC        1533
TTCTGCAGCA AATCCCCATG GTTCATCCCC CTACCATTGA CCCATCCACA        1583
GTCTTCTATG CCAGATGAGT CACCCCCGAT GTCCAGCCCC GACTCAAACT        1633
CAATAATTGC CTCAAATAGC TCCTCCAACC CCCGCTCACA TTCCTCCCAT        1683
AGGGCCTTTT TTTCCTCTTC CAAGAAATCC ACATAACCCT GAAGCAAATC        1733
ACAAAACCCA TCAAAACCCA GGAGTCCTAT ACACTCCAAC TGCTGATGCC        1783
TCTCTTCCCT CTCCCGGCGC TTTTGATCCT TTTCCCGCAG GCGCTCCTTT        1833
CTGCGCCGCT CCCGCTCCTC ACGCTCCTGC AGAAGCTTTA AGATCTCCCG        1883
CTGCTCCTCC GCCAACAGCT TCCGACGAGA GTCTCGCACC TGCTCGCTGA        1933
CCGATCCCGA CCCCAGAGGG CGGCCTTTTG CTGTCCTTCT TGGTTCCTCT        1983
CCAGGGGGAG GCACATCAGA TGTCAGACTC TCCTCCCCCT GGTCTCCTAA        2033
CGGCAATCTC CTAAAATAGT CTAAAAATTA CACATAATTA CAACCCTGTC        2083
TCCTCTCAG CCC ATT TCC CAG GAT TCG GAC AGA GCC TCC TAT        2125
          Pro Ile Ser Gln Asp Ser Asp Arg Ala Ser Tyr
                   25                  30
ATG GAT ACC CCG TCT ACG TGT TTG GCG ATT GTG TAC AGG CCG        2167
Met Asp Thr Pro Ser Thr Cys Leu Ala Ile Val Tyr Arg Pro
         35                  40                  45
ATT GGT GTC CCG TCT CAG GTG GTC TAT GTT CCA CCC GCC TAC        2209
Ile Gly Val Pro Ser Gln Val Val Tyr Val Pro Pro Ala Tyr
         50                  55                  60
ATC GAC ATG CCC TCC TGG CCA CCT GTC CAG AGC ACC AGC TCA        2251
Ile Asp Met Pro Ser Trp Pro Pro Val Gln Ser Thr Ser Ser
         65                  70
```

```
CCT GGG ACC CCA TCG ATG GAC GCG TTG TCA GCT CTC CTC TCC                    2293
Pro Gly Thr Pro Ser Met Asp Ala Leu Ser Ala Leu Leu Ser
 75                  80                  85

AAT ACC TTA TCC CTC GCC TCC CCT CCT TCC CCA CCC AGA GAA                    2335
Asn Thr Leu Ser Leu Ala Ser Pro Pro Ser Pro Pro Arg Glu
         90                  95                 100

CCG CCA AGA CCC TCA AGG TCC TTA CCC CTC CCA CCA CTC CTG                    2377
Pro Pro Arg Pro Ser Arg Ser Leu Pro Leu Pro Pro Leu Leu
            105                 110                 115

TCT CCC CCA AGG TTC CAC CCG CCT TCT TCC AAT CAA TGC GAA                    2419
Ser Pro Pro Arg Phe His Pro Pro Ser Ser Asn Gln Cys Glu
                120                 125                 130

AGC ACA CCC CCT ATC GCA ATG GAT GCC TGG AAC CAA CCC TCG                    2461
Ser Thr Pro Pro Ile Ala Met Asp Ala Trp Asn Gln Pro Ser
                    135                 140

GGG ATC AGC TCC CCT CCC TCG CCT TCC CTG AAC CTG GCC TCC                    2503
Gly Ile Ser Ser Pro Pro Ser Pro Ser Leu Asn Leu Ala Ser
145                 150                 155

GTC CCC AAA ACA TCT ACA CCA CCT GGG GAA AAA CCG TAG                        2542
Val Pro Lys Thr Ser Thr Pro Pro Gly Glu Lys Pro
    160                 165                 170

(2) INFORMATION FOR SEQ ID NO:19:

(i) SEQUENCE CHARACTERISTICS:
        (A) LENGTH: 170 amino acids
        (B) TYPE: amino acid
        (C) STRANDEDNESS:
        (D) TOPOLOGY: unknown (xi) SEQUENCE DESCRIPTION: SEQ ID NO:19:

Met Pro Lys Thr Arg Arg Gln Arg Thr Arg Ala Arg Arg
                 5                  10

Asn Arg Pro Pro Thr Pro Trp Pro Ile Ser Gln Asp Ser Asp
 15                  20                  25

Arg Ala Ser Tyr Met Asp Thr Pro Ser Thr Cys Leu Ala Ile
         30                  35                  40

Val Tyr Arg Pro Ile Gly Val Pro Ser Gln Val Val Tyr Val
            45                  50                  55

Pro Pro Ala Tyr Ile Asp Met Ser Trp Pro Pro Val Gln
                60                  65                  70

Ser Thr Ser Ser Pro Gly Thr Pro Ser Met Asp Ala Leu Ser
                    75                  80

Ala Leu Leu Ser Asn Thr Leu Ser Leu Ala Ser Pro Pro Ser
 85                  90                  95

Pro Pro Arg Glu Pro Pro Arg Pro Ser Arg Ser Leu Pro Leu
        100                 105                 110

Pro Pro Leu Leu Ser Pro Pro Arg Phe His Pro Pro Ser Ser
            115                 120                 125

Asn Gln Cys Glu Ser Thr Pro Pro Ile Ala Met Asp Ala Trp
                130                 135                 140

Asn Gln Pro Ser Gly Ile Ser Ser Pro Pro Ser Pro Ser Leu
                    145                 150

Asn Leu Ala Ser Val Pro Lys Thr Ser Thr Pro Pro Gly Glu
155                 160                 165

Lys Pro
    170
```

METHODS FOR THE DETECTION OF HTLV-II ANTIBODIES EMPLOYING NOVEL HTLV-II NRA ENVELOPE PEPTIDES

RELATED APPLICATIONS

The present application is a continuation-in-part application of U.S. application Ser. No. 08/086,415, filed Jul. 1, 1993, incorporated herein by reference, now abandoned.

FIELD OF THE INVENTION

The present invention relates generally to an isolate of human T-cell lymphotropic virus type II ("HTLV-II") referred to as "NRA." More particularly, the invention relates to compositions derived from the NRA provirus, and to the use of such compositions in assays and kits to detect HTLV infection.

BACKGROUND OF THE INVENTION

Human T-cell lymphotropic virus type I ("HTLV-I") has been established as the etiologic agent of two diseases, adult T-cell leukemia ("ATL") [Poiesz et al., *Proc. Natl. Acad. Sci. USA*, 77:7415–7419 (1980); Uchiyama et al., *Blood*, 50:481–492 (1977)] and a neurologic disorder known either as HTLV-associated myelopathy ("HAM") [Tsujimoto et al., *Mol. Biol. Med.*, 5:29–42 (1988)] or tropical spastic paraparesis ("TSP") [Gessain et al., *Lancet*, II:407–409 (1985)].

Genetic analysis of HTLV-I genomes has been performed. [Ratner et al., *AIDS Res. and Human Retroviruses*, 7:923–941 (1991); Goodenow et al., *J. Acquired Immune Defic. Syndr.*, 2:344–352 (1989); Gray et al., *Virology*, 177:391–395 (1990)]. Genetic diversity within the HTLV-I genome has been reported to be associated with the geographical origin of the isolate. [Gessain et al., *J. Virol.*, 66:2288–2295 (1992); Sherman et al., *J. Virol*, 66:2556–2563 (1992)].

Another type of human lymphotropic virus, HTLV-II, has been identified among approximately half of the U.S. blood donors with anti-HTLV reactivity [Hjelle et al., *Blood*, 76:450–454 (1990); Lee et al., *Lancet*, 337:1435–1439 (1991)], and a high risk association has been reported in intravenous drug users ("IVDU") from New Orleans [Lee et al., *Science*, 244:471–475 (1989)], New York City [Robert-Guroff et al., *JAMA*, 255:3133–3137 (1986); Ehrlich et al., *Blood*, 74:1658–1664 (1989)], the United Kingdom [Tedder et al., *Lancet*, 11:125–128 (1984)], and Italy [Zella et al., *Lancet*, 336:575–576 (1990)]. HAM/TSP-like myelopathy has also been described in one patient coinfected with HIV-1 and HTLV-II [Berger et al., *Neurology*, 41:85–87 (1991)] and in several additional HTLV-II infected individuals. [Hjelle et al., *Lancet*, 339:645–646 (1992); Rosenblatt et al., *AIDS*, 6:1151–1158 (1992)].

HTLV-II was first identified in a patient ("Mo") with a T-cell variant hairy cell leukemia. [Saxon et al., *Ann. Intern. Med.*, 88:323–326 (1978); Kalyanaraman et al., *Science*, 218:571–573 (1982)]. A "Mo" cell line was established from the spleen cells of that patient, and the Mo provirus was characterized. [Chen et al., *Nature*, 305:502–505 (1983)]. U.S. Pat. No. 4,438,032 to Golde et al. further describes the Mo T-lymphoblast cell line and the proteinaceous products produced by that cell line. The nucleotide sequence of the Mo provirus has also been determined. [Shimotohno et al., *Proc. Natl. Acad. Sci. USA*, 82:3101–3105 (1985)].

In 1986, Rosenblatt et al. reported the second isolation of HTLV-II in a patient ("NRA") with an atypical hairy cell leukemia. [Rosenblatt et al., *New Engl. J. Med.*, 315:372–377 (1986)]. Cell lines, NRA, NRA-P, NRA-WM 2, and NRA-SH were established and restriction enzyme analysis of the new HTLV-II isolate was performed. The data from the genetic analysis of the NRA isolate showed that the genomes of HTLV-II$_{Mo}$ and HTLV-II$_{NRA}$ are not identical. [Id]. Rosenblatt et al., *Blood*, 71:363–369 (1988), later reported in a follow-up analysis of the NRA patient's HTLV infection that the patient had two coexistent lymphoproliferative disorders of distinct T and B cell origin.

Recently, Hall et al. and Dube et al. have described and compared various HTLV-II isolates. Based on partial sequencing of the gp21e envelope region and restriction mapping of several HTLV-II isolates from intravenous drug users, Hall et al. have proposed that HTLV-II$_{Mo}$ and HTLV-II$_{NRA}$ are two different HTLV-II subtypes. [Hall et al., *J. Virol.*, 66:2456–2463 (1992)]. Particularly, Hall et al. describe HTLV-II$_{Mo}$ as being subtype A and HTLV-II$_{NRA}$ as being subtype B.

Dube et al., *J. Virol.*, 67:1175–1184 (1993) have also investigated the heterogeneity of HTLV-II in different patients residing in the Western hemisphere. Dube et al. report that at least two genetically distinct HTLV-II strains are present in the Western hemisphere. Based on the data obtained in the study, Dube et al. suggest that HTLV-II isolates introduced into the New World were more heterogeneous than the HTLV-I strains.

Various compositions and assays for detecting HTLV-I infection have been described. [See, for example, WO 85/01803 to Slamon, published Mar. 27, 1986]. The Abbott Laboratories' HTLV-I EIA is a commercially available kit assaying for HTLV-I antibodies. The kit employs HTLV-I viral lysate-coated beads. There is also commercially available from Cambridge Technologies a kit assaying for HTLV-I antibodies. That kit employs HTLV-I viral lysate and recombinant gp21E protein attached to microtiter plate wells.

Compositions and assays for detecting and/or differentiating HTLV-I and HTLV-II infection have also been described. [See, for example, co-owned and co-pending U.S. patent application Ser. No. 08/170,063, filed Dec. 20, 1993; WO 90/10231 to Blomberg, published Mar. 5, 1990; WO 90/15820 to Vahlne, published Dec. 27, 1990; Lal et al., *J. Infectious Diseases*, 163:41–46 (January 1991)].

To Applicants' knowledge, prior to the filing of the present application the NRA provirus and NRA infected cell lines were not publicly available. Moreover, Applicants are not aware of any publications reporting the use of the presently disclosed NRA compositions in assays or kits to detect HTLV infection.

SUMMARY OF THE INVENTION

One embodiment of the invention is directed to various DNA sequences derived from HTLV-II$_{NRA}$ provirus. More particularly, there is provided:

a DNA sequence coding the genome of HTLV-II$_{NRA}$ provirus;

a DNA sequence coding for the HTLV-II$_{NRA}$ gag region and for gag p19, p24, and p15;

a DNA sequence coding for the HTLV-II$_{NRA}$ pol region;

a DNA sequence coding for the HTLV-II$_{NRA}$ env region and for env p21e;

a DNA sequence coding for the HTLV-II$_{NRA}$ tax region; and a DNA sequence coding for the HTLV-II$_{NRA}$ rex region. Amino acid sequences corresponding to the respective DNA sequences are also provided.

Another embodiment of the invention is directed to HTLV-II$_{NRA}$ compositions, including polypeptides and proteins coded by the sequences disclosed in the present application, purified HTLV-II$_{NRA}$ viral lysate, purified HTLV-II$_{NRA}$, and tissue culture grown cells infected with HTLV-II$_{NRA}$.

Another embodiment of the invention is directed to methods and assays for detecting anti-HTLV antibodies in a test sample.

A further embodiment of the invention is directed to kits for detecting anti-HTLV antibodies in a test sample.

BRIEF DESCRIPTION OF THE DRAWINGS

FIG. 2 shows the complete nucleotide sequence of the HTLV-II$_{NRA}$ genome.

DETAILED DESCRIPTION OF THE PRESENTLY PREFERRED EMBODIMENTS

The present invention provides various compositions derived from HTLV-II$_{NRA}$ provirus and HTLV-II$_{NRA}$ infected cell lines. The compositions of the invention include HTLV-II$_{NRA}$ provirus lysates and DNA sequences coding the entire genome of the NRA provirus and parts thereof. These and other compositions are described further below. The NRA isolate of HTLV-II was first identified in a patient diagnosed with an atypical hairy cell leukemia. [Rosenblatt et al., *New Engl. J. Med.*, 315:372–377 (1986)]. Cell lines infected with the NRA isolate, NRA, NRA-P, NRA-WM 2, and NRA-SH, were then established. The NRA-P cell line is a Leu 4+ T-cell line established from a culture of Patient NRA's peripheral blood lymphocytes in the presence of phytohemagglutinin. [Rosenblatt et al., *New Engl. J. Med.*, 315:372–377 (1986)]. The WIL-NRA cell line, produced from cocultivation of Patient NRA's peripheral blood lymphocytes with the EBV-transformed B-cell line, WIL-2, is a B cell line that does not produce factors such as cytokines, colony stimulating factor, interferon, or growth factors. Prior to the filing of the present application, the NRA provirus and NRA infected cell lines were not publicly available.

The WIL-NRA cell line has been deposited at the American Type Culture Collection, 12301 Parklawn Drive, Rockville, Md. 20852, as of Mar. 15, 1994, under the terms of the Budapest Treaty, and will be maintained for a period of thirty (30) years from the date of deposit, or for five (5) years after the last request for the deposit, or for the enforceable period of the U.S. patent, whichever is longer. The deposit described herein is provided for convenience only, and is not required to practice the invention in view of the teachings provided herein. The WIL-NRA cell line was accorded ATCC No. CRL 11580.

One embodiment of the invention relates to a NRA lysate. NRA lysates useful in the practice of the invention include lysates of NRA infected cell lines and NRA provirus which may be prepared in a variety of ways. For example, the lysate may be prepared by standard procedures known in the art. Modifications of standard procedures for preparing the NRA lysate can also be used. For instance, a purified NRA lysate may be prepared according to the process described in Example 1 below. Other suitable and equivalent modifications and preparations of NRA lysate are also contemplated and will be apparent to those skilled in the art.

Nucleotide and amino acid sequences derived from the NRA provirus are also provided by the invention. The NRA provirus was cloned and sequenced, as described in Example 2 below. The entire genomic sequence of the NRA provirus is disclosed in FIG. 2. The genomic sequence of the NRA provirus is also provided in SEQ ID NO:1 in the SEQUENCE LISTING below.

Figure 1:
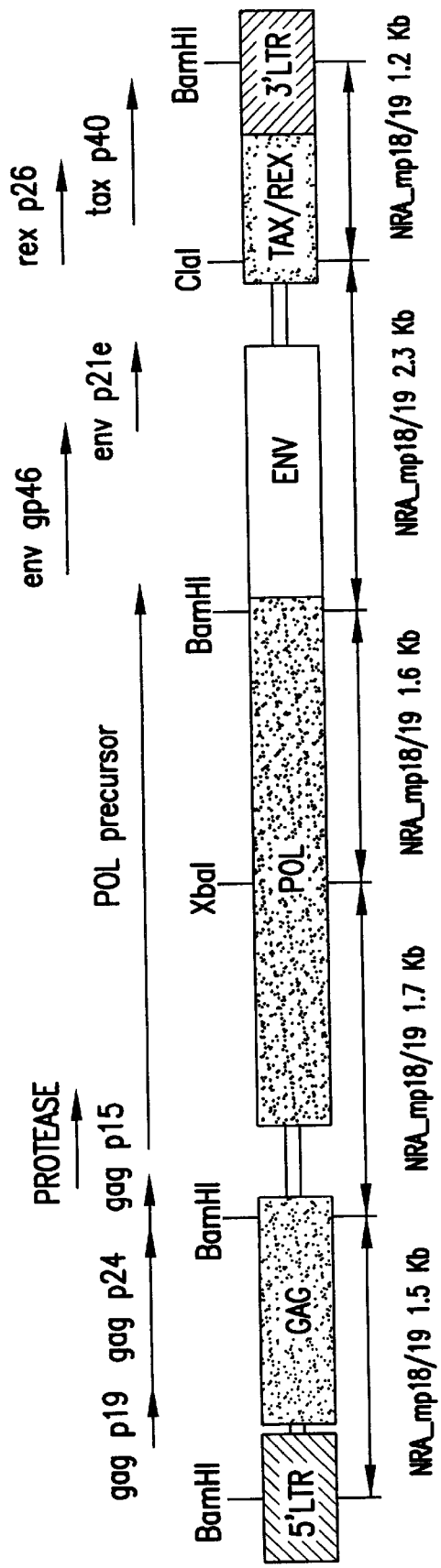
FIG. 1 shows a genomic sequence diagram and restriction map of the HTLV-II$_{NRA}$ provirus.

The nucleotide sequence encoding the NRA provirus gag region is also provided. The gag region comprises nucleotides 810–2111 of the genomic sequence shown in FIG. 2 and SEQ ID NO:2. The corresponding amino acid sequence is shown in SEQ ID NO:3. As shown in FIG. 1, the gag region encodes p19, p24, and p15. Gag p19 comprises nucleotides 810–1217. Gag p24 comprises nucleotides 1218–1859, and gag p15 comprises nucleotides 1860–2111. These nucleotide sequences are shown in SEQ ID NOs 4, 6, and 8, respectively, of the SEQUENCE LISTING. The amino acid sequences corresponding to the p19, p24, and p15 nucleotide sequences are provided in SEQ ID NOs 5, 7, and 9, respectively.

The nucleotide sequence encoding the NRA pol region is also provided. The pol region, which includes the gal precursor, comprises nucleotides 2242–5190 in the sequence shown in FIG. 2 and SEQ ID NO:10. The amino acid sequence corresponding to the nucleotide sequence encoding the pol region is provided in SEQ ID NO:11 in the SEQUENCE LISTING.

The invention further provides the nucleotide sequence encoding the NRA env region. The env region comprises nucleotides 5183–6643 in the sequence shown in FIG. 2 and SEQ ID NO:12. The corresponding amino acid sequence is shown in SEQ ID NO:13. As shown in FIG. 1, the env region encodes gp46 and p21e. Env p21e comprises nucleotides 6107–6643. (See, SEQ ID NO:14). The amino acid sequence corresponding to the p21e nucleotide sequence is shown in SEQ ID NO:15.

The nucleotide sequence encoding the NRA tax/rex region is also provided. The NRA tax region comprises nucleotides 5183–5186 and 7216–8282 in the sequence of FIG. 2 and SEQ ID NO:16. As shown in FIG. 1, the tax region encodes p40x. The rex region comprises nucleotides 5124–5186 and 7216–7665 in the sequence shown in FIG. 2 and SEQ ID NO:18. The rex region encodes p26. (FIG. 1). The amino acid sequences corresponding to the tax and rex region nucleotide sequences are shown in SEQ ID NOs 17 and 19, respectively. As described in Example 3 below, the sequence encoding the NRA tax/rex region comprises an additional 25 amino acids as compared to the tax/rex region of the HTLV-II$_{Mo}$ provirus. Further comparisons are shown in Table 4d below. Typically, the tax/rex region is involved in regulating or controlling expression of genes. Although not fully understood, it is believed that the additional amino acids may alter the function of the tax gene since it has been reported that carboxy terminal mutants of HTLV-I tax may affect specificity of cellular targets by altering transactivation through specific pathways such as the NFkB pathway. [Ruben et al., *Neu. Biol.*, 1:275 (1989)].

The sequences described above may be produced by techniques known in the art. For example, the sequences may be obtained by purification of proviral DNA by phenol/chloroform extraction or PCR, or produced by recombinant cloning techniques or chemical synthesis. The nucleotide sequences may be single stranded or double stranded. It is contemplated that NRA peptides, polypeptides, and proteins corresponding to the disclosed sequences or fragments thereof may also be produced by techniques known in the art.

Fragments of the disclosed nucleotide and amino acid sequences may have the functionality or capacity of the NRA sequences specified herein. Nucleotide and amino acid sequences having certain deletions, insertions, or substitutions may also have the functionality or capacity of the NRA sequences specified herein. All such sequences and the use of such sequences are considered to come within the scope of the present invention.

The NRA compositions disclosed by the invention may be utilized in a variety of ways. For instance, the nucleotide sequences may be used to detect the presence of complementary sequences associated with HTLV. The sequences may also be used as primers or probes in ligase chain reaction ("LCR") or polymerase chain reaction ("PCR") techniques. PCR amplification is known in the art and is further described in U.S. Pat. Nos. 4,683,195 and 4,683,202. LCR techniques are also known in the art and are described further in EP-A-320-308, EP-A-336-731, WO 89/09835, and WO 89/12696. The NRA compositions may also be used as either probes or antigens in Southern or Western Blot techniques known in the art. [Towbin et al., *Proc. Natl. Acad. Sci.*, 76:4350–4354 (1979); Southern, *J. Mol. Biol.*, 98:503–517 (1975)]. It is also contemplated that the NRA compositions may be used to produce antibodies and vaccines. Further, the NRA compositions may be employed in the methods and kits described below.

The methods of the present invention relate to assays for detecting antibodies associated with HTLV in a test sample. The assays include but are not limited to, conventional immunoassays such as agglutination, radioimmunoassays, enzyme immunoassays, luminescence assays and fluorescence assays. Various assay formats known in the art may be utilized, such as direct and indirect sandwich assays and dot blot assays. In one embodiment, HTLV-II antibodies are detected. In an alternative embodiment, HTLV-I and/or HTLV-II antibodies are detected. The methods of the invention employ at least one NRA composition. The NRA composition may include viral lysate, purified, synthetic, or recombinant-produced protein, polypeptide or peptide, nucleic acid sequence, or combinations thereof. It is contemplated that the NRA composition may be used alone or in combination with other diagnostic reagents. For instance, as described in Example 1 below, NRA lysate and HTLV-I viral lysate are used to detect HTLV-I and/or HTLV-II antibodies. It is contemplated that the NRA lysate can be used in combination with a spike antigen or recombinant or synthetic proteins. It is further contemplated that the NRA composition can be employed in combination with other known reagents to detect antibodies and/or antigens, including but not limited to those antibodies and/or antigens associated with human immunodeficiency virus ("HIV"), hepatitis B virus ("HBV") or hepatitis C virus ("HCV").

In a preferred embodiment of the present methods, antibodies to HTLV-I and/or HTLV-II are detected. The method comprises contacting a test sample with NRA lysate and HTLV-I viral lysate to form a reaction mixture. One or more solid phases may be used in the assay. As used in the present application, the term "test sample" refers to a sample of human or animal biological fluid, including but not limited to, serum, plasma, ascites, urine, cerebral spinal fluid or any other body constituents or tissue culture supernatants. The term "solid phase" is used in a broad sense and refers to any material which is insoluble, or can be made insoluble by a subsequent reaction. The solid phase can be a variety of materials and can be selected by one skilled in the art without undue experimentation. Examples of solid phases for use in the invention include, but are not limited to, porous and non-porous materials, latex particles, microparticles, beads, membranes, plastic tubes, and microtiter wells. The size, dimensions, and shape of the solid phase may be selected by one skilled in the art. Those skilled in the art may determine empirically suitable solid phases for the assay and will readily appreciate that the selection of the solid phase will depend on various factors such as the quantity of test sample, the steps involved in the assay, and the means utilized for detecting and measuring the labels.

Suitable methods for attaching the lysate on the solid phase include ionic, hydrophobic and covalent bonding. Such techniques for attaching the lysate are within the ordinary skill in the art. Linking agents known in the art may also be utilized to secure attachment of the lysate on the solid phase. The linking agent may be incorporated as part of, or derivatized onto, the solid phase before the lysate is added.

The reaction mixture is incubated for a time and under conditions sufficient for HTLV antigen/antibody complexes to form. Selecting appropriate times, temperature, and other conditions of the incubation are well within the skill in the art. The reaction mixture may be simultaneously contacted, or subsequently contacted, with an indicator reagent comprising a binding member attached to a signal generating compound, to form a second reaction mixture. The binding member can be any molecule capable of specifically binding HTLV antigen or antibody, including a hapten or anti-hapten such as biotin or anti-biotin, avidin or biotin, carbohydrate, lectin, complementary nucleotide sequence, and enzymes. Such binding members are known in the art and are commercially available. The signal generating compounds, or "labels," contemplated by the invention include chromogens, catalysts such as enzymes, luminescent compounds such as fluorescein and rhodamine, chemiluminescent compounds, radioactive labels and direct visual labels. Examples of enzymes include alkaline phosphatase, horseradish peroxidase, beta-galactosidase. The selection of suitable labels is within the skill in the art. Preferably, the label is capable of producing a signal either by itself or in conjunction with one or more additional substances. It will also be readily apparent to those persons skilled in the art that various techniques known in the art may be employed to attach or "conjugate" the label to the binding member. The second reaction mixture is incubated for a time and under conditions sufficient to form HTLV antigen/antibody/ indicator reagent complexes. The presence of HTLV is determined by detecting the label associated with or bound to the solid phase or by detecting the label associated with or bound to the unreacted indicator reagent. Any, or all, steps in the disclosed methods may be automated or performed manually.

Although the methods above describe the use of NRA lysate, it is contemplated that purified, synthesized, or recombinantly-produced NRA peptides, polypeptides and proteins may be employed in such methods to detect antibodies to HTLV. Moreover, while the present invention discloses the preference for use of one or more solid phases, it is contemplated that the NRA compositions may be utilized in non-solid phase, or homogeneous, assays. These assays are known to those skilled in the art and are considered to lie within the scope of the present invention.

The present invention also provides kits for detecting HTLV antibodies. Generally, the kit comprises one or more containers holding NRA lysate. Alternatively, the one or more containers may hold purified, synthetic or recombinant NRA protein, polypeptide or peptide. Suitable containers include bottles, vials, trays, test tubes and microtiter plates. Preferably, the kit also includes a label or package insert which indicates that the NRA composition in the kit is used to detect HTLV antibodies. The label or package insert may also indicate directions for conducting HTLV assay, such as those disclosed in the present application. The kit may also comprise suitable reagents such as buffers, diluents, enzymes and the like.

In a preferred embodiment, the kit comprises trays containing multiple beads or microparticles having attached thereto NRA lysate; peroxidase-labeled goat antibody to human IgG; antibody diluent; test sample diluent; OPD tablets; and color detection diluent. In a more preferred embodiment, the kit further comprises HTLV-I lysate.

The following Examples illustrate ways of making the novel compositions of the present invention and performing assays using those compositions. The Examples, however, are intended only to be illustrative, and are not to be construed as placing limitations upon the scope of the invention.

EXAMPLES

The methods employed in the examples below were performed according to standard tissue culture and molecular genetics techniques known in the art, and as described by Maniatis et al., *Molecular Cloning a Laboratory Manual*, Cold Spring Harbor (1982), unless indicated otherwise. The restriction enzymes used in the following examples were obtained from Gibco BRL, Gaithersburg, Md., and New England Biolabs, Beverly, Mass. They were used according to the manufacturer's instructions unless indicated otherwise.

Example 1

Assays Employing HTLV-I and HTLV-II Viral Lysates to Detect HTLV-I and/or HTLV-II Antibodies A. Viral Lysate Preparation Viral lysates were prepared as follows. HTLV-I was isolated from cell line HUT-102:B2 (Advanced Biotechnologies, Inc. Bethesda, Md.). HUT-102:B2 is a clone of HUT-102 (available from the American Type Culture Collection, Rockville, Md.), and produces the same virus as HUT-102. HTLV-II was isolated from NRA infected cell line WIL-NRA, described above. First, the viruses were grown in tissue culture. A serum-containing medium was used, such as RPMI-1640 (Gibco BRL, Gaithersburg, Md.) supplemented with 10% fetal bovine serum. The viruses excreted into the culture medium were then harvested and used to prepare the lysates. The cells in which the viruses are grown were not lysed.

The harvested viruses were purified by continuous flow ultracentrifugation and passed over a 20%–45% sucrose density gradient using a CF32 rotor. Intact virus was selected based on buoyant density of 1.15 for HTLV-I and 1.14 for HTLV-II. Sucrose concentrations from 28.5% to 38.7% were pooled. Next, the pooled viruses were lysed using 0.25% TRITON X100 in Tris saline buffer (10 mM Tris, 150 mM NaCl) and sonication, followed by centrifugation. The supernatant obtained after centrifugation contained the viral lysate.

B. HTLV-I/HTLV-II NRA Lysate Bead Assay Testing HTLV-I Positive Samples and HTLV-II Positive Samples The HTLV-I and HTLV-II viral lysates (prepared as described in Section A above) were combined at about a 50:50 ratio and then coated by hydrophobic adsorption onto about ¼ inch diameter polystyrene beads (Unity, Des Plaines, Ill.), described in further detail below.

All washing and recirculation steps were performed in a bead coating column. A coating solution was prepared by adding the lysates and TRITON X100 to phosphate buffered solution ("PBS") and mixing. Beads were loaded into a column and washed with 15% propanol for 25–35 minutes. The coating solution was added and recirculated for 2 hours±5 minutes at about 40° C. The beads were rinsed with PBS, washed with PBS containing TRITON X100 for 30±2 minutes at about 40° C., and rinsed again with PBS. A blocking solution (PBS containing bovine serum albumin) was added, recirculated for 30±2 minutes at about 40° C., and followed by a PBS rinse. Next, an overcoat solution (PBS containing 2% sucrose) was added and recirculated for 10–20 minutes. The beads were then dried with nitrogen for 60–90 minutes initially at 40° C. and then at 25° C., unloaded from the column, filled into containers and stored dessicated at 2–8° C.

Assays were conducted by testing thirty three samples (8 HTLV-I confirmed positive samples, 20 HTLV-II confirmed positive samples, and 5 non-differentiated samples). The samples (10 $\mu$l) were diluted (1:41) with a diluent (400 $\mu$l) which blocks nonspecific binding. The diluent was sterile filtered and contained 10% calf serum, 20% goat serum, 2% nonfat dry milk, 0.15% TRITON X100, sodium azide, EDTA, and EGTA in a standard Tris-PBS buffer containing 0.15 M NaCl. The nonfat dry milk was not denatured or heated. Normal human serum which did not contain HTLV-I or HTLV-II antibodies (negative control) and human sera confirmed for HTLV-I or HTLV-II antibodies (positive controls) were also tested.

The diluted samples and controls (200 $\mu$l) were added to the wells of a 5"×11" plate (Courtesy, Wheeling, Ill.) containing 60 wells per plate. Lysate-coated beads were placed in the plates, one bead per well, and the plates were covered with a seal. The plates were incubated for 60±5 minutes at about 40±2° C. in a COMMANDER® Dynamic Incubator (Abbott Laboratories, Abbott Park, Ill.) using the rotational mode.

The cover seal from the plates was removed and the beads were washed with distilled water. Goat antibody to human IgG (gamma specific) labeled with horseradish peroxidase (Kirkegaard & Perry, Gaithersburg, Md.) was then added to each well. The labeled goat antibody was provided in Tris-saline buffer containing 10% fetal calf serum and 0.25% TRITON X100. The labeled goat antibody was diluted before use with a diluent containing 15% fetal calf serum, 5% goat serum, 0.25% TRITON X100 in Tris buffer. New cover seals were then applied to each plate.

After a further incubation for 30±5 minutes at about 40±2° C. (in the COMMANDER® Dynamic Incubator described above) and washing the beads with distilled water, 300 $\mu$l freshly prepared substrate solution (hydrogen peroxide and orthophenylenediamine, "OPD," J. P. Baker, Phillipsburg, N.J.) was added to each well. The plates were covered to protect from light. The plates were then incubated at room temperature for 30±2 minutes. Color development was stopped by adding about 300 $\mu$l to 1 ml 1N sulfuric acid to each well. The absorbance of the liquid phase was then measured at Å492 nm.

For comparison, the samples described above were also assayed using the Cambridge Technologies HTLV-I kit, conducted in accordance with manufacturer's instructions. The Cambridge Technologies HTLV-I assay failed to detect several HTLV-II positive samples (which were detected in the HTLV-I/II NRA lysate bead assay) and performed particularly poor when HTLV-II samples were diluted 1:125–1:2000 (0 detected) as compared to the same dilutions in the HTLV-I/II NRA lysate bead assay (5 positive samples detected). Results of the HTLV-I/II NRA lysate bead assay showed that the use of the HTLV-I and HTLV-II NRA lysate increased the detectability of HTLV-II positive samples and increased sensitivity for HTLV-I positive samples. The HTLV-I/II NRA lysate bead assay also showed increased specificity (at a rate of 99.93%).

C. HTLV-I/HTLV-II NRA Lysate Bead Assay Testing Random Plasma Samples

A panel of plasma samples was obtained from donors and screened for ALT, HBsAg, HCV antibodies, HIV-1, HIV-2, HBcAg, syphilis, and HTLV-I. A total of 1057 plasma samples were tested in Abbott's HTLV-I EIA (according to manufacturer's instructions) and the HTLV-I/II NRA lysate bead assay, as described in Section B above. Samples were considered reactive when the S/CO was ≧1.000. The results are shown in Table 1 below.

TABLE 1

| ASSAY | Number Tested | OD | SD | S/CO | SD | SD to CO | # Reactive |
|---|---|---|---|---|---|---|---|
| HTLV-I EIA | 1057 | 0.142 | 0.048 | 0.278 | 0.092 | 7.82 | 1* |
| HTLV-I/II Lysate | 1057 | 0.093 | 0.031 | 0.177 | 0.057 | 14.44 | 1* |

S/CO = sample/cutoff value
SD = standard deviation
OD = optical density
SD to CO = number of sample standard deviations from population mean to assay cutoff
*Sample was indeterminant by supplemental tests.

The data indicates that within the panel of plasma samples tested, there was improved performance by the HTLV-I/II NRA lysate bead assay. In the HTLV-I/II NRA lysate bead assay, the sample population mean was separated from the assay cutoff by 14.44 population standard deviations compared to 7.82 population standard deviations for the HTLV-I EIA assay. The increased number of standard deviations from the population mean to the assay standard cutoff is advantageous because it decreases the potential for false reactivity and false positives.

D. Effect of Potentially Interfering Substances on Specificity of the HTLV-I/HTLV-II NRA Lysate Bead Assay A panel of potentially interfering substance samples was assayed in the HTLV-I/II NRA lysate bead assay (as described in Section B above) and the Abbott HTLV-I EIA (according to manufacturer's instructions) to examine specificity. A total of 167 individual specimens, from 18 sample categories (shown in Table 2 below) were tested. The results of the assays are shown in Table 2.

TABLE 2

| Sample Category | Number Tested | HTLV-I EIA Lysate (Lot A) # Reactive | HTLV-I/II Lysate (Lot B) # Reactive | HTLV-I/HTLV-II #Reactive |
|---|---|---|---|---|
| Anti-HCV Positive | 10 | 1* | 0 | 0 |
| Acute Hepatitis B | 7 | 0 | 0 | 0 |
| Chronic Hepatitis B | 13 | 0 | 0 | 0 |
| Anti-CMV Positive | 10 | 0 | 0 | 0 |
| Anti-Rubella Positive | 10 | 0 | 0 | 0 |
| Anti-Toxo Positive | 10 | 0 | 0 | 0 |
| Anti-VZV Positive | 9 | 0 | 0 | 0 |
| Anti-EBV Positive | 10 | 0 | 0 | 0 |
| Anti-HSV Positive | 10 | 0 | 0 | 0 |
| Pregnant Females | 10 | 0 | 0 | 0 |
| Myeloma Patients | 10 | 1** | 0 | 0 |
| Autoimmune Disease | 10 | 0 | 0 | 0 |
| Milk Allergic Donors | 8 | 0 | 0 | 0 |
| Hyper-Gammaglobulinemia | 10 | 0 | 0 | 0 |
| Elevated Bilirubin | 10 | 0 | 0 | 0 |
| Elevated Triglycerides | 5 | 0 | 0 | 0 |
| Elevated Cholesterol | 5 | 0 | 0 | 0 |
| Elevated Hemoglobin | 10 | 0 | 0 | 0 |

*Panel member HCV #8 is indeterminant in a supplemental test.
**Panel member Myeloma #10 is negative in a supplemental test.

No false reactivity was exhibited in the HTLV-I/II NRA lysate bead assay. In the panel, HCV (#8) and Myeloma (#10) were reactive in the HTLV-I EIA assay. Supplemental testing of the HCV (#8) and Myeloma (#10) samples by the Diagnostic Biotechnologies Laboratories HTLV-I/II Western Blot (Version 2.3) kit showed HCV (#8) indeterminant and Myeloma (#10) negative.

E. HTLV-I/HTLV-II NRA Lysate Bead Assay Testing Serially Diluted HTLV-I Positive Samples and HTLV-II Positive Samples PCR confirmed HTLV-I positive and HTLV-II positive samples were serially diluted and assayed in the HTLV-I EIA (according to manufacturer's instructions) and the HTLV-I/II NRA lysate bead assay (as described in Section B above) to assess the relative sensitivity of the assays. Two panels each of the HTLV-I and HTLV-II samples were prepared by diluting the respective positive plasmas into recalcified negative plasma.

Figure 3:
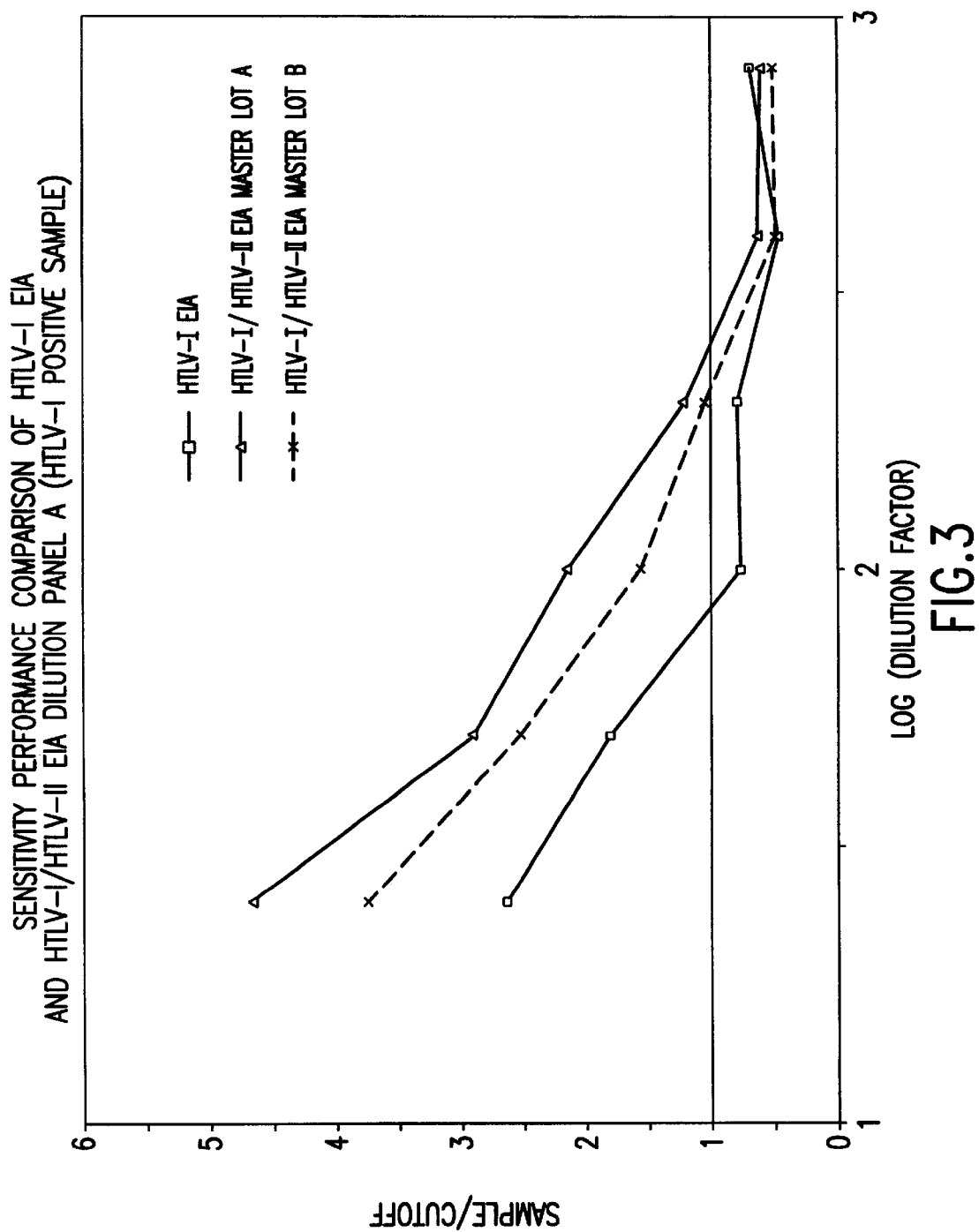
FIG. 3 is a graph comparing results of the HTLV-I EIA and the HTLV-I/HTLV-II NRA lysate bead assay for a dilution panel of HTLV-I positive samples.
Figure 4:
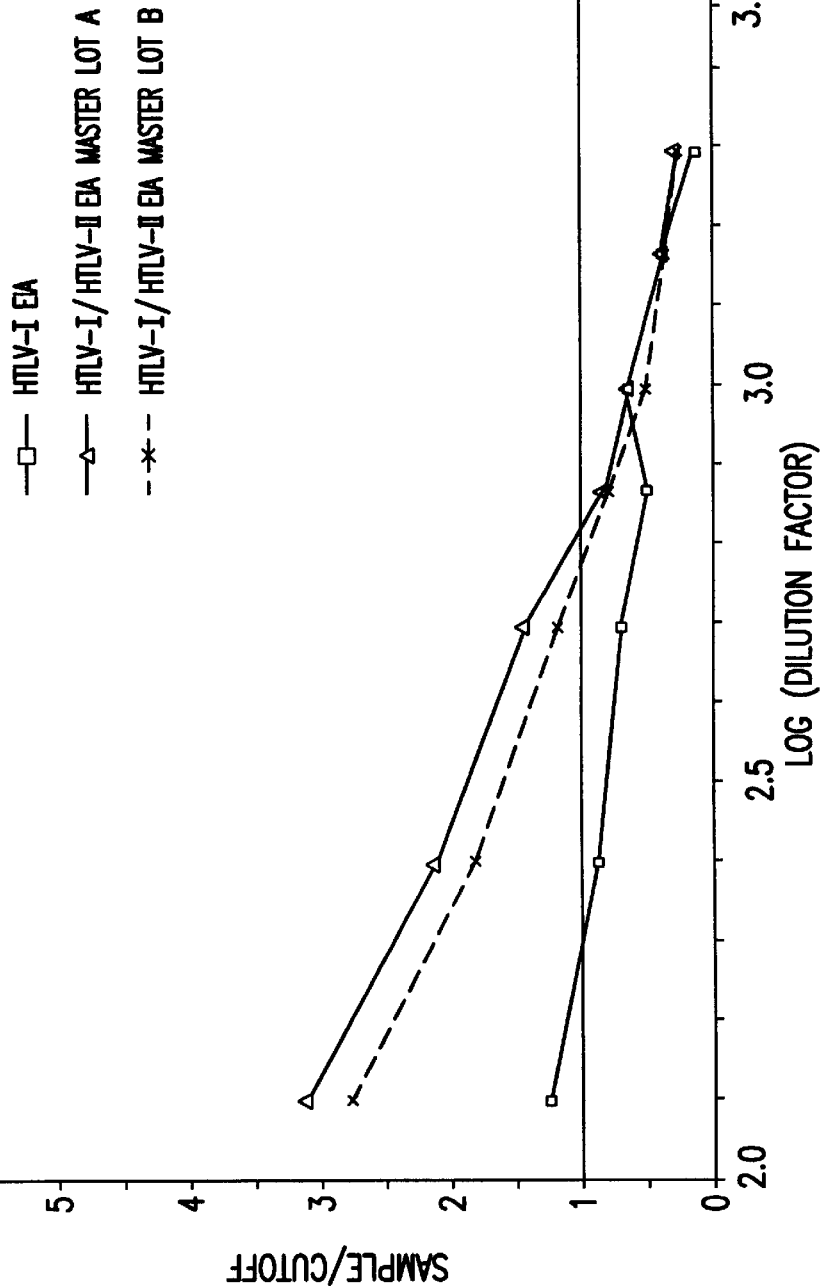
FIG. 4 is a graph comparing results of the HTLV-I EIA and the HTLV-I/HTLV-II NRA lysate bead assay for a dilution panel of HTLV-II positive samples.

Graphs of the results of the assays are shown in FIGS. 3 and 4. The data is summarized in Table 3 below.

TABLE 3

| Sample/Dilution Range | Number Tested | HTLV-I EIA (Lot A) # Reactive | HTLV-I/II Lysate (Lot B) # Reactive | HTLV-I/II # Reactive |
|---|---|---|---|---|
| A. HTLV-I (1:25–1:800) | 6 | 2 | 4 | 4 |
| B. HTLV-I (Neat–1:2048) | 12 | 8 | 9 | 9 |
| C. HTLV-I (Neat–1:2048) | 12 | 7 | 9 | 8 |
| D. HTLV-II (1:125–1:2000) | 7 | 1 | 3 | 3 |
| E. HTLV-II (Neat–1:2048) | 12 | 8 | 11 | 11 |
| F. HTLV-II (Neat–1:2048) | 12 | 8 | 10 | 10 |
| TOTALS | 61 | 34 | 46 | 45 |

The overall dilution series reactivity for the HTLV-I/II NRA lysate bead assays (46/61 for Lot A and 45/61 for Lot B) exceeded the HTLV-I EIA (34/61). The data also showed that the HTLV-I/II NRA lysate bead assay had increased sensitivity for HTLV-I and HTLV-II antibody compared to the HTLV-I EIA as demonstrated by an elevated sample cutoff value for all diluted samples.

F. HTLV-I/HTLV-II NRA Lysate Microparticle Assay

Microparticles of approximately 0.2–0.3. micron (purchased from Serodyne, Indianapolis, Ind.) were coated with either the HTLV-I or HTLV-II NRA lysate (prepared as described in Section A above) so that there were two types of microparticles—microparticles coated only with HTLV-I viral lysate and microparticles coated only with HTLV-II NRA viral lysate. HTLV-I lysate coated microparticles were coated at about 35° C. for 16–24 hours at about 5 times the working concentration (60 μg/ml with 0.6% solids). HTLV-II lysate coated microparticles were coated at room temperature for 16–24 hours at about 10 times the working concentration (60 μg/ml with 0.6% solids). The types of microparticles were then combined to form a mixture containing 12 μg/ml HTLV-I, 6 μg/ml HTLV-II, 9% sucrose, 50 mM EDTA, 0.1 M phosphate, 0.1% BSA, 0.1% Tween, 0.1% azide, pH 7.5.

Assays were conducted by testing HTLV-I confirmed positive samples, HTLV-II confirmed positive samples, and non-differentiated samples. Approximately 100 μl of test sample plasma or serum was added to wells in a reaction tray. Next, 50 μl of the microparticle mixture was added to the wells and the sample/microparticle mixtures were incubated for about 18 minutes at 35° C. The incubation took place in the reaction well portion of the reaction tray.

Following the incubation, the reaction mixture was transferred to a capture membrane positioned in the reaction tray by two washes with 300 μl of a transfer buffer (0.01 M phosphate, 150 mM NaCl, 0.1% polyethylene glycol, 0.1% sodium azide, pH 7.2). About 10 minutes was allowed to complete drainage of the liquid from the reaction well.

Then, 50 μl of a probe mixture was added to the microparticles on the capture membrane. The probe mixture included a blend of biotinylated HTLV-I (about 10 ng/ml), HTLV-II (about 20 ng/ml), glycoprotein (40 ng/ml), 0.1 M Tris, 2% bovine serum, 0.1 M NaCl, 0.1% azide, pH 8.0. The mixture was then incubated at 35° C. for about 20 minutes. HTLV-I probes were biotinylated at between 2–8° C. for 16–24 hours at 500 μg/ml (0.4:1 wt:wt ratio biotin/antigen). HTLV-II probes were biotinylated at 2–8° C. for 16–24 hours at 200 μg/ml (0.8:1 wt:wt ratio biotin/antigen). Glycoprotein was biotinylated at 2–8° C. for 16–24 hours at 200 μg/ml (0.5:1 wt:wt ratio biotin/antigen). All biotinylated preparations were dialyzed prior to use. The glycoprotein was also precipitated using ammonium sulfate prior to use.

Unbound probe was washed into an absorbent blotter in the reaction tray by 300 μl of a wash solution containing 0.1 M Tris, 0.1% TRITON X100, 150 mM NaCl, 0.1% sodium azide, pH 8.5. Next, 50 μl of an acridinium labeled anti-biotin mouse monoclonal antibody (160 ng/ml diluted in 0.01 M phosphate, 0.15 M NaCl, 4% BSA, 1% TRITON X100, 0.1% azide, pH 6.3; labeling performed by reacting for 10 min. about 5:1 molar ratio acridinium/antibody to reach ratio of 1.8:1, then fractionated over an HPLC sizing column) was added and incubated for an additional 10 minutes at 35° C. Unbound conjugate was washed into the blotter with 300 μl of a wash solution (0.025 M MES, 0.9% NaCl, 0.1% Proclin, pH 5.7). After 10 minutes, the acridinium label was triggered by injecting 50 μl of an alkaline peroxide activator solution (0.2 N NaOH, 0.2% hydrogen peroxide, 0.03% DTPA) and photons were collected and counted.

For comparison, the test samples were also assayed using the Cambridge Technologies HTLV-I kit and Abbott HTLV-I EIA, both conducted in accordance with manufacturer instructions. Samples were considered reactive when the sample value to cut off value ratio (S/CO) was ≧1.00. The results are shown below in Tables 3a, 3b, and 3c.

TABLE 3a

HTLV-I Confirmed Positive Test Samples

| Sample ID | Microparticle Assay | HTLV-I EIA | Cambridge Assay |
|---|---|---|---|
| Prism 1B | 4.1 | 1.7 | 3.99 |
| Prism 1C | 2.75 | 1.5 | 3.51 |
| Prism 5B | 3.75 | | 2.79 |
| Prism 7D | 1.5 | 2.8 | 2.05 |
| Prism 7G | 2.25 | 1.3 | 1.41 |
| Prism 7H | 7.4 | 2.6 | 4.9 |
| Prism 7U | 10.05 | | 5.41 |
| Prism 7V | 14 | | 6 |

TABLE 3b

HTLV-II Confirmed Positive Test Samples

| Sample ID | Microparticle Assay | HTLV-I EIA | Cambridge Assay |
|---|---|---|---|
| Prism 3–4 | 7.15 | 1 | 3.38 |
| Prism 5E | 7.8 | | 2.47 |
| Prism 5G | 4.5 | | 1.06 |
| Prism 6–219 | 6.35 | 0.8 | 2.13 |
| Prism 6C | 22.7 | 1.4 | 3.92 |
| Prism 6K | 14.25 | 0.3 | 2.93 |
| Prism 6M | 11.95 | 0.2 | 2.01 |
| Prism 6P | 14.6 | | 2.05 |
| Prism 8I | 16.8 | 1.6 | 1.76 |
| BH 4338 | 5.4 | 0.8 | 1.12 |
| BH 9483 | 6.2 | 0.7 | 0.98 |
| BH 5328 | 2.75 | 1 | 1.7 |
| BH 9725 | 10.85 | 1.3 | 2.14 |
| BH 9726 | 14.45 | 3 | 6.18 |

TABLE 3c

Non-Differentiated Test Samples

| Sample ID | Microparticle Assay | HTLV-I EIA | Cambridge Assay |
|---|---|---|---|
| Prism 3–8 | 10.35 | 1.6 | 5.62 |
| Prism 3–9 | 14.35 | 1.1 | 3.34 |
| Prism 3–10 | 12.15 | 1.5 | 2.86 |
| Prism 3–15 | 19.4 | 2 | 2.98 |
| Prism 3–17 | 10.7 | 1.1 | 2.33 |
| Prism 3–25 | 10.35 | 1.2 | 4.37 |
| Prism 3–28 | 14.35 | 1.6 | 3.1 |
| Prism 3–46 | 12 | 1.5 | 3.53 |
| Prism 3–47 | 12.3 | 1.6 | 2.07 |
| Prism 3–55 | 12.5 | 1.2 | 4.05 |
| Prism 3–57 | 9.95 | 1.4 | 3.57 |
| Prism 3–75 | 7.3 | 1 | 1.04 |
| Prism 5C | 4.8 | | 3.64 |
| Prism 5F | 9.1 | | 3.16 |
| Prism 5H | 11.35 | | 3.97 |
| Prism 5I | 13.6 | | 3.6 |
| Prism 5J | 13.05 | | 1.69 |

Example 2

Cloning and Sequencing the Genome of HTLV-II$_{NRA}$ Provirus

A. Production of HTLV-II$_{NRA}$ Clones

A complete molecular clone of the HTLV-II$_{NRA}$ provirus (_NRA19a) was cloned from a genomic library prepared from restriction enzyme, Sau 3A, partially-digested genomic DNA from the HTLV-II$_{NRA}$ infected cell line, NRA-P. [Rosenblatt et al., *New Engl. J. Med.*, 315:372–377 (1986)]. Sau 3A digested genomic DNA was size fractionated on a sodium chloride gradient, and inserts measuring 8 to 23 kb were subcloned into the Sau 3A site of _EMBL3 (Stratagene, LaJolla, Calif.). Transformants were packaged using Gigapack Plus® (Stratagene, LaJolla, Calif.) and transformed into LE392 (Stratagene, LaJolla, Calif.). Approximately 106 phage plaques in a restrictive bacterial host strain of *E. coli* (Strain LE 392, Stratagene, LaJolla, Calif.) were screened using a 4.7 kb BamHI fragment of HTLV-II$_{Mo}$ clone pH6neo (pH6 B5.0) and were rescreened with a 3.5 kb BamHI 3' fragment from pH6neo (pH6 B3.5). [Chen et al., *Nature*, 305:502–505 (1983)]. Clones that hybridized to both probes were isolated. The largest of the clones, designated _NRA19a, was found to contain complete gag, pol, env, tax and rex coding sequences. This clone was digested with BamHI and resultant fragments subcloned into PM13 SK+ Bluescript vector (Stratagene, LaJolla, Calif.) yielding the following three clones: PM13.NRA1.5 (1.5 kb including partial 5' LTR and gag); PM13.NRA3.3 (3.3 kb including 3' gag and pol); and PM13.NRA3.5 (3.5 kb including partial 3' pol and tax/rex).

B. Subcloning

HTLV-II clone PM13.NRA 3.3 was digested with XbaI and clone PM13.NRA3.5 was digested with ClaI to generate the restriction fragments illustrated in FIG. 1. Fragments were subcloned into M13, mp18, and mp19 (all obtained from Pharmacia Biotech, Inc., Piscataway, N.J.). Complementary orientations were screened by direct gel electrophoresis and complementation testing on ethidium bromide stained gels. [Sambrook et al., *Molecular Cloning, a Laboratory Manual*, Second Edition, Cold Spring Harbor Laboratory Press, 4.39–4.43 (1989)].

C. Nucleotide Sequencing

Figure 2C:
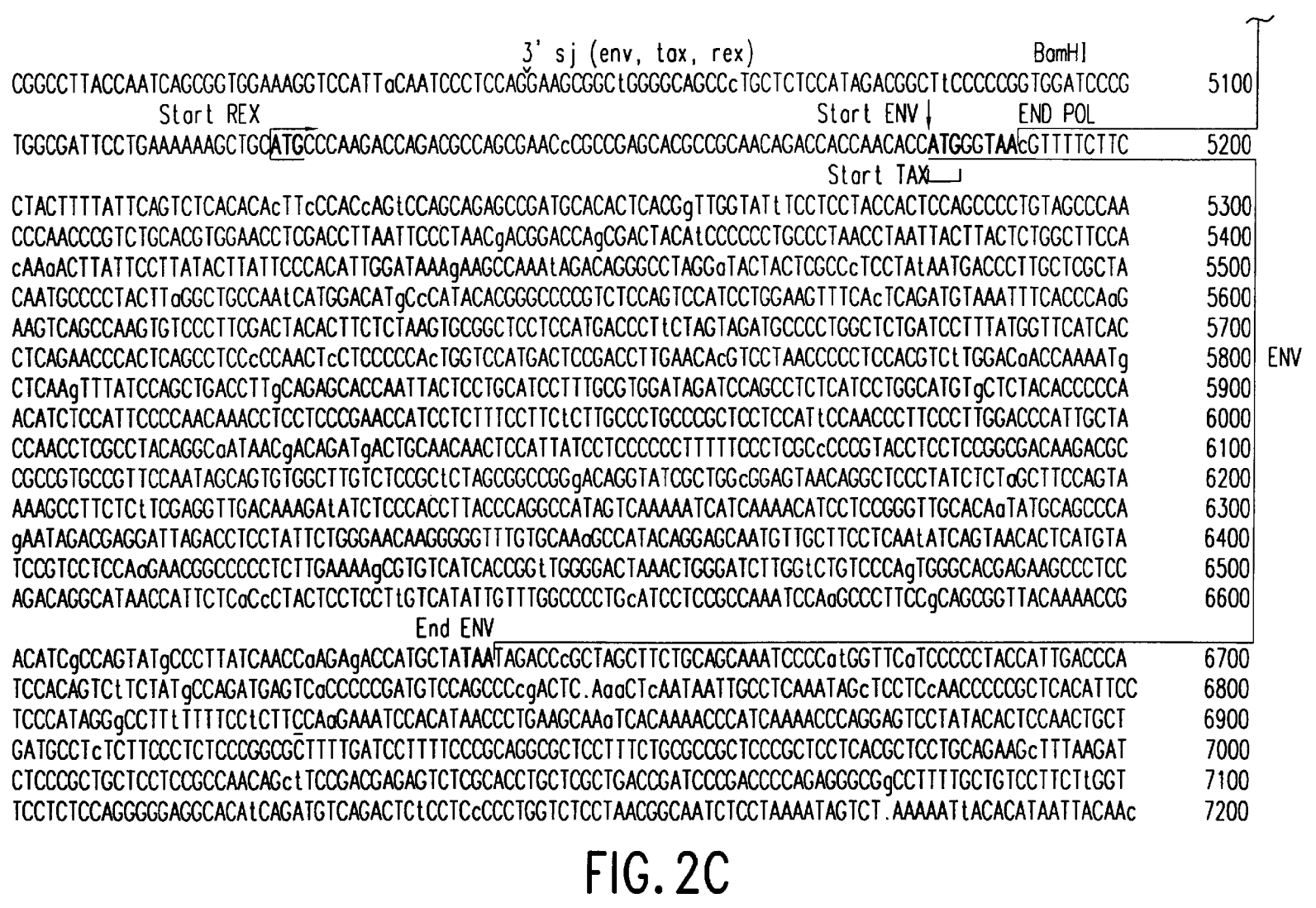

Sanger dideoxy sequence walking strategy [Sanger et al., *Proc. Natl. Acad. Sci. USA*, 74:5463–5467 (1977)] was performed using M13 forward primers (United States Biochemical Corp., Cleveland, Ohio). Sequencing reactions were performed with Sequenase® version 2.0 protocol (United States Biochemical, Cleveland, Ohio) using [_$^{32}$P] ATP signal incorporation (Amersham, Arlington Heights, Ill.). Sequences were resolved on 1 meter 6% and 4% polyacrylamide/8M urea gels [Barker et al., *Plant Mol. Bio.*, 2:335–350 (1983)] and data were transcribed from autoradiograms into Intelligenetics Suite software (Intelligenetics, Mountain View, Calif.) for assembly and analysis. The complete nucleotide sequence of HTLV-II$_{NRA}$ provirus consisted of 8957 bases and is shown in FIG. 2 and SEQ ID NO. 1 in the SEQUENCE LISTING below.

Example 3

Comparison of HTLV-II$_{NRA}$ and HTLV-II$_{Mo}$ Genomes

Sequence alignment between proviral genomes of HTLV-II isolate Mo (8952 nucleotides) and isolate NRA was performed. The HTLV-II$_{NRA}$ complete genome was aligned to the HTLV-II$_{Mo}$ sequence (GenBank accession number M10060) using the GCG software package [Devereux et al., *Nucleic Acids. Res.*, 12:387 (1984)] and the GAP alignment program [Needleman et al., *J. Mol. Biol.*, 48:443–453 (1970)]. Overall percent homology between the two isolates was 95.2% with 430 nucleotide changes, 8 deletions and 10 insertions in HTLV-II$_{NRA}$ as compared to HTLV-II$_{Mo}$. Table 4a below shows the nucleotide homology in the 5' LTR region.

TABLE 4a

Comparison of LTR sequence data for HTLV-II isolates Mo and NRA.

| GENOMIC REGION | | LTR | REX RESPONSIVE ELEMENT | CIS ACTING REPRESSIVE ELEMENT | 2ND CIS ACTING REPRESSIVE ELEMENT |
|---|---|---|---|---|---|
| NUCLEOTIDE REGION | Mo | 1–763 | 405–520 | 520–630 | 645–750 |
| | NRA | 1–766 | 400–525 | 520–635 | 640–755 |
| TOTAL BASES | Mo | 763 | 116 | 111 | 106 |
| | NRA | 766 | 126 | 116 | 116 |
| NT CHANGES IN NRA VS MO | | 47/766 (6.1%) | 6/126 (4.8%) | 7/116 (6.0%) | 11/116 (9.5%) |
| DELETIONS | | 6 | 0 | 4 | 0 |
| INSERTIONS | | 9 | 10 | 9 | 10 |

TABLE 4a-continued

Comparison of LTR sequence data for HTLV-II isolates Mo and NRA.

| GENOMIC REGION | LTR | REX RESPONSIVE ELEMENT | CIS ACTING REPRESSIVE ELEMENT | 2ND CIS ACTING REPRESSIVE ELEMENT |
|---|---|---|---|---|
| % NT HOMOLOGY | 719/766 (93.7%)* | 120/126 (94.8%)* | 109/116 (93.4%)* | 105/116 (89.6%)* |

(*) reflects indenty based on UW GCG gap program.

As indicated in Table 4a, alignment of the LTR region of HTLV-II$_{Mo}$ (763 bases) and HTLV-II$_{NRA}$ (766 bases) showed overall nucleotide homology of 93.7% with 47 base changes and 15 gaps (6 bases found in HTLV-II$_{Mo}$ only and 9 bases found in HTLV-II$_{NRA}$ only). Homology was 94.8% for the rex responsive element, 93.4% for the first cis acting repressive element (CRS) and only 89.6% for the second cis acting repressor sequence.

Percent nucleotide and amino acid homology for the major open reading frames gag, protease, and pol are shown in Table 4b below.

TABLE 4b

Comparison of sequence data for open reading frames gag, protease, and pol of HTLV-II isolates Mo and NRA.

| GENOMIC REGION | | GAG P19 | GAG P24 | GAG P15 | PROTEASE | POL (PRECURSOR) |
|---|---|---|---|---|---|---|
| NUCLEOTIDE REGION | Mo | 807–1214 | 1215–1856 | 1857–2108 | 2078–2613 | 2239–5187 |
| | NRA | 810–1217 | 1218–1859 | 1860–2111 | 2081–2616 | 2242–5190* |
| TOTAL BASES | Mo | 408 | 642 | 252 | 536 | 2949 |
| | NRA | 408 | 642 | 252 | 536 | 2949 |
| NT CHANGES IN NRA VS MO | | 19/408 (4.7%) | 25/642 (3.9%) | 10/252 (4.0%) | 24/536 (4.5%) | 144/2949 (4.9%) |
| % NT HOMOLOGY | | 389/408 (95.3%) | 617/642 (96.1%) | 242/252 (96.0%) | 512/536 (95.5%) | 2805/2949 (95.1%) |
| TOTAL AMINO ACIDS | | 136 | 214 | 84 | 178 | 983 |
| AA CHANGES IN NRA VS MO | | 1/136 (0.7%) | 3/214 (1.4%) | 3/84 (3.6%) | 6/178 (3.4%) | 37/983 (3.8%) |
| % AA HOMOLOGY | | 135/136 (99.3%) | 211/214 (98.6%) | 81/84 (96.4%) | 172/178 (96.6%) | 946/983 (96.2%) |

(*) Pol start is at nt 2437.

Table 4b shows that the gag precursor consisted of 1302 nucleotides with an overall identity of 95.3%, 96.1% and 96.0% for the p19, p24 and p15 gene products, respectively. The gene coded for 434 amino acids with homology of 99.3% for p19, 98.6% for p24 and 96.4% for p15. The protease gene contained 536 bases. Homology with HTLV-II$_{Mo}$ was 95.5% at the nucleotide level and 96.6% for the 178 amino acids. The pol precursor was composed of 2949 nucleotides encoding 983 amino acids. Identity to HTLV-II$_{Mo}$ was 95.1% for the nucleotide sequence and 96.2% for the 983 amino acids.

Percent nucleotide and amino acid homology for env is shown in Table 4c. The env gene encoded for 487 amino acids including gp46 and p21e. Homology between HTLV-II$_{NRA}$ and HTLV-II$_{Mo}$ was 95.5% for nucleotides 5183 to 6643 and 6.9% at the amino acid level.

TABLE 4c

Comparison of sequence data for env open reading frames of HTLV-II isolates Mo and NRA.

| GENOMIC REGION | | ENV Polyprotein | ENV P21E |
|---|---|---|---|
| NUCLEOTIDE REGION | Mo | 5180–6640 | 6104–6640 |
| | NRA | 5183–6643 | 6107–6643 |
| TOTAL BASES | Mo | 1461 | 537 |
| | NRA | 1461 | 537 |

TABLE 4c-continued

Comparison of sequence data for env open reading frames of HTLV-II isolates Mo and NRA.

| GENOMIC REGION | ENV Polyprotein | ENV P21E |
|---|---|---|
| NT CHANGES IN NRA VS MO | 65/1461 (4.5%) | 25/537 (4.7%) |
| % NT HOMOLOGY | 1396/1461 (95.5%) | 512/537 (95.3%) |
| TOTAL AMINO ACIDS | 487 | 179 |
| AA CHANGES IN NRA VS MO | 15/487 (3.1%) | 5/179 (2.8%) |
| % AA HOMOLOGY | 472/487 (96.9%) | 174/179 (97.2%) |

TABLE 4d

Comparison of sequence data for open reading frames env, tax, and rex of HTLV-II isolates Mo and NRA.

| GENOMIC REGION | | TAX | REX | UNTRANSLATED ENV TO TAX |
|---|---|---|---|---|
| NUCLEOTIDE | Mo | 5180–5183, | 5121–5183, | 6641–7213 |
| REGION | NRA | 7214–8205 | 7214–7663 | 6644–7215 |
|  |  | 5183–5186, | 5124–5186, |  |
|  |  | 7216–8282 | 7216–7665 |  |
| TOTAL | Mo | 4, 992 | 63, 450 | 573 |
| BASES | NRA | 4, 1067 | 63, 450 | 572 |
| NT CHANGES IN NRA VS MO | | 40/1071 (3.7%) | 11/513 (2.1%) | 30/572 (5.2%) |
| % NT HOMOLOGY | | 1031/1071 (96.2%) | 502/513 (97.8%) | 542/572 (94.8%) 2 DELETIONS 1 INSERTION |
| TOTAL AMINO ACIDS | | 332 357 | 171 |  |
| AA CHANGES IN NRA VS MO | | 7/357 (2.0%) | 9/171 (5.3%) |  |
| % AA HOMOLOGY | | 350/357 (97.9%)*^ | 162/171 (94.7%) |  |

(*) Reflects % identity based on UW GCG gap program.
(^) Reflections % identity with or without 25 additional amino acids in NRA.

The tax/rex coding sequences partially overlap and encode proteins required for viral transcription and mRNA processing. Percent nucleotide and amino acid homology for env is shown in Table 4d. The tax gene of HTLV-II$_{NRA}$ consisted of 1071 nucleotides from bases 7216 to 8282 and included an initiation codon at bases 5183 to 5186. Identity with HTLV-II$_{Mo}$ was 96.2% at the nucleotide level and 97.9% for the amino acids. In HTLV-II$_{NRA}$, an additional 25 amino acids at the 3' end of the tax/rex open reading frame was present and extended into the 3' LTR (nucleotide positions 8208 to 8282). For this region, 2 base changes and one amino acid substitution occurred. Rex was encoded by nucleotides 5124 to 5186 and 7216 to 7665. Homology for the 513 base sequence of rex was 97.8% for nucleotides and 94.7% for amino acids.

In the untranslated env to tax/rex region (Table 4d), identity for the 572 nucleotides from the end of env to the start of tax/rex (bases 6644 to 7215) was 94.8% including 2 deletions and one insertion.

Example 4

Genetic Variation within the Envelope Gene of HTLV-II Isolates

A. Methods and Materials

1. United States Donor Samples

As part of a U.S. multi-site prevalence study of HTLV infection [Lee et al., Lancet, 337:1435–1439 (1991)], routine blood donors who had been identified and confirmed as anti-HTLV-I/II seropositive were contacted for study participation and informed consent. Plasma and peripheral blood lymphocytes ("PBL") were collected from 50 ml of freshly drawn heparinized blood by a Ficoll-Hypaque density gradient. Lymphocytes were cryopreserved and DNA was later extracted for PCR. Following differentiation by PCR, HTLV-II infected subjects with available lymphocytes were selected for further study.

2. United States IVDU

Plasma and packed red blood cells were obtained from consenting anti-HTLV seropositive intravenous drug user ("IVDU") subjects by plasmapheresis at Serologicals, Inc., Pensacola, Fla. Lymphocytes were collected by Ficoll-Hypaque density gradient and cryopreserved for DNA extraction. HTLV-II infected subjects were selected by PCR.

3. Italian IVDU

Whole blood or plasma and cryopreserved lymphocytes were received from different seropositive IVDU populations in Milano, Italy and from male Caucasian IVDU inmates in a state prison in Rome, Italy. Lymphocytes were harvested from whole blood as described above and were either cryopreserved or placed in continuous cell culture.

4. Continuous Culture of PBL's

Fresh or cryopreserved PBL's from 8 US donors, 10 US IVDU and 16 Italian IVDU were placed in continuous culture. Twenty million donor PBL's, at a concentration of 1 million cells/ml, and 5 million PHA-stimulated umbilical cord blood lymphocytes (Advanced Biotechnologies, Inc., Columbia, Md.) were resuspended in RPMI 1640 media (GIBCO BRL, Gaithersburg, Md.) containing 20% heat inactivated fetal bovine serum and 10% interleukin 2 (IL-2) (Advanced Biotechnologies, Inc., Columbia, Md.). Cells were incubated at 37° C. in the presence of 6% $CO_2$ and were replenished regularly with RPMI 1640 culture media containing 10% IL-2. Five million fresh PHA-stimulated cord blood lymphocytes were added to the cultures at days 7, 14, and 21. At day 40 of culture, IL-2 concentration was gradually decreased until cells were IL-2 independent. Cultures were maintained for 8 to 12 weeks and were cryopreserved at various intervals during expansion.

5. Cell Line Controls

Cloned HTLV-II$_{Mo}$ control DNA was obtained from cell line 729 containing plasmid pH6neo [Rosenblatt et al., N. Engl. J. Med., 313:372–377 (1986)]. HTLV-II$_{NRA}$ control proviral DNA was obtained from cultured PBL's of patient NRA. [Rosenblatt et al., N. Engl. J. Med., 313:372–377 (1986)].

6. HTLV Serology

Initially, serum was screened for antibodies to HTLV-I/II by an enzyme immunoassay ("EIA") (Abbott Laboratories, Chicago, Ill.). The EIA used purified, sonicated and detergent disrupted HTLV-I virions from HUT 102-B2 cell line (Advanced Biotechnologies, Inc., Bethesda, Md.) as the antigen source.

EIA reactive samples were then evaluated by Western blot. Western blot strips were prepared using the HTLV-I antigen described above. Viral proteins were separated electrophoretically on 12% polyacrylamide gels followed by transfer to nitrocellulose. Test sera were exposed to the strips overnight followed by incubation of strips with biotin labeled goat-anti-human IgG and peroxidase labeled streptavidin (Kirkegaard & Perry, Gaithersburg, Md.). Color development was visualized by incubation of the strips with a substrate solution of 4-chloro-1-napthol and hydrogen peroxide. Samples were considered confirmed if antibodies were present to HTLV gene products core p24 and envelope gp46.

Samples exhibiting no reactivity to virus specific bands were considered non-confirmed and required no further testing. Samples exhibiting reactivity with only one band were classified as indeterminate and were further tested by a radioimmunoprecipitation assay (RIPA): $^{35}$S-methionine and $^{35}$S-cysteine (Amersham Life Sciences, Arlington Heights, Ill.) were used to metabolically label HTLV-I infected HUT 102-B2 cells which were then disrupted by detergent and clarified by centrifugation. Serum samples were incubated with the cell lysate and protein-A sepharose (Pharmacia, Piscataway, N.J.) overnight at 4° C. Complexes of protein-A sepharose, antigen and antibody were washed with a series of high and low salt buffers, disrupted by boiling and loaded onto 12% polyacrylamide gels. Following electrophoresis, gels were fixed, incubated with fluorophor, dried and autoradiographed. Samples were considered confirmed if antibodies to HTLV core p24 and envelope gp61 were present by either RIPA alone or a combination of Western blot and RIPA.

Serum samples from study subjects were also tested for antibodies to HTLV-I or -II using a series of synthetic peptide-coated polystyrene beads in a solid phase EIA. Each peptide represented 20 to 30 amino acids from HTLV-I or -II envelope regions, respectively. The assay conditions were the same as for the HTLV screening EIA.

A semi-automated dot blot confirmatory immunoassay (Matrix) was also used for confirmation. The antigens in the test array included highly purified HTLV-I viral p19, recombinant p24, recombinant p21e and synthetic peptides specific for HTLV-I or -II envelope bound to nitrocellulose in a small cassette. Serum or plasma diluted 100-fold was incubated in the cassette for 30 minutes, followed by thirty minute incubations with biotin labeled anti-human IgG (Kirkegaard & Perry, Gaithersburg, Md.), alkaline phosphatase labeled anti-biotin (Kirkegaard & Perry, Gaithersburg, Md.), and BCIP/NBT substrate (Sigma, St. Louis, Mo.). After each step, unbound reagent was removed by a 20 minute automated wash step. Following the final step, reflectance or intensity of reactions was determined by an optical reader. Samples were considered confirmed if positive signals developed to both gag p24 and env p21e.

7. Screening PCR

To discriminate HTLV-I and II, DNA from available PBL's was prepared by phenol/chloroform extraction and evaluated by PCR to detect viral specific HTLV tax/rex, gag p19, or env p21e sequences. $^{35}$P labeled PCR amplified products were digested with restriction enzymes, separated by polyacrylamide gel electrophoresis and visualized by autoradiography as previously described. [Lee et al., Science, 244:471–475 (1989); Lee et al., Lancet, 337:1435–1439 (1991)].

8. Characterization of HTLV-II in United States and Italian Isolates

Plasmas from 8 US donors, 10 US IVDU, and 16 Italian IVDU were evaluated for presence of antibodies to HTLV-I/II by Western blot, RIPA, Matrix and synthetic peptides. All US subjects were HTLV seropositive and confirmed by Western blot/RIPA and Matrix. Of the 16 Italian IVDU, 14 (87.5%) individuals were seropositive and confirmed, while 2 (12.5%) were indeterminate due to absence of env gp61 antibodies. However, all 16 Italian IVDU were confirmed by Matrix with antibodies to gag p24 and env p21e. The US donors, 9/10 (90%) US IVDU and 12/16 (75%) Italian IVDU had antibodies to HTLV-II gp46 synthetic peptide.

PCR evaluation of DNA extracted from culture lymphocytes confirmed that all US donors and US IVDU specimens used in this study were HTLV-II infected. Of the seropositive Italian IVDU, HTLV-II provirus was detected by PCR in 8/16 lymphocyte cultures.

9. Enzyme Restriction Mapping of PCR Amplified Products

DNA from culture PBL's or from cell lines Mo and NRA was prepared by phenol/chloroform extraction. Sequence variation in the HTLV-II envelope region was evaluated using two pairs of oligonucleotide primers specific for HTLV-II gp46. The positions of primers corresponded to nucleotide numbers in an entire proviral genome of HTLV-$II_{Mo}$. The first pair, identified as 82/88, defined a 539 base sequence from nucleotide 5323 to 5861. The second pair, 85/86, defined a 434 base sequence from nucleotide 5618 to 6051. Nucleotide positions of the primers were as follows: #82 (5323–5342), #88 (complementary to 5842-5861), #85 (5681–5637), and #86 (complementary to 6032–6051). In total, 729/924 nucleotides (78.9%) of the gp46 gene were amplified. The upstream oligonucleotide primer was labeled at the 5' end with [__$^{32}$P] ATP in all experiments. Conditions for amplification were as previously reported [Lee et al., Science, 244:471–475 (1989)].

To evaluate sequence variation between HTLV-II isolates, aliquots of PCR amplified product were subjected to restriction enzyme digestion followed by 8% polyacrylamide gel electrophoresis and autoradiography.

10. DNA Sequencing of United States and Italian Isolates

DNA sequencing of HTLV-II gp46 amplified sequences was performed by the Sanger dideoxy-mediated chain termination method [Sanger et al., Proc. Natl. Acad. Sci. USA, 74:5463–5467 (1977)] using Sequenase Version 2.0 (United States Biochemical, Cleveland, Ohio) with minor modifications. To sequence the region of relevant restriction sites, a third primer pair was used. Pair 81/85A defined a region from nucleotides 5291–5610. The position for primer #81 was 5279–5298 and #85A was complementary to nucleotides 5618–5637. DNA from HTLV-II isolates was PCR amplified for 40 cycles using one primer of the pair (described above) labeled at the 5-' end with [__$^{32}$P]-ATP. PCR product was separated by 8% polyacrylamide gel electrophoresis and autoradiographed to identify the position of the relevant amplified product. The radiolabeled DNA was eluted from the gel with 0.5M ammonium acetate, 1 mm EDTA Ph 8.0 by overnight incubation at 37° C. on a rocking platform. DNA was recovered by ethanol precipitation in the presence of 0.3M sodium acetate and dried overnight under vacuum conditions. Samples were reconstituted with distilled water and denatured to single strand DNA by treatment with 0.4M NaOH, 0.4 mm EDTA for 30 minutes at 37° C. DNA was again collected by ethanol precipitation and vacuum dried. After reconstitution of the samples, dideoxy-sequencing was performed using 5' end labeled [__$^{32}$P]-ATP primer that was unlabeled during the initial amplification step. By alternating the labeled primer, DNA could be sequenced from both stands for overlapping reads. Samples were resolved on 40 cm long 6% acrylamide/urea sequencing gels at 1500 volts for 1.5 hours.

B. Comparison of Genetic Variation

PCR primers were chosen for regions of sequence homology between the two prototypes. To map potential variation among HTLV-II isolates, proviral DNA extracted from HTLV-$II_{Mo}$ and HTLV-$II_{NRA}$ control cell lines and from cultured cells of 8 US donors, 10 US IVDU and 7 Italian IVDU was amplified by PCR for two overlapping gp46 regions followed by restriction enzyme digestion of amplified sequences. With primer pair 82/88, the 539 nt PCR amplified product of HTLV-$II_{Mo}$ prototype displayed the following size enzyme digestion products: Taq I (295 nt), Hph I (259 nt), Apa I (224 nt), Fnu 4HI (193 nt), Bbv I (179 nt), Rsa I (140 nt), and Hae III (132 nt). A second pattern was observed with the HTLV-$II_{NRA}$ prototype. The 539 nt PCR amplified product was not affected by Rsa I, an enzyme that cleaves between 5'-GT AC-3' sequences at base 5462, defined by numbered positions in a complete HTLV-$II_{Mo}$ proviral genome. A third digestion pattern was observed for proviral DNA of Italian IVDU. Cleavage of the 539 nt PCR amplified product by Rsa I resulted in a digestion product of 91 nt, or approximately 50 nt smaller than the expected sequence.

Enzyme restriction mapping for a second HTLV-II gp46 PCR amplified region of 434 nt defined by primers 85/86 showed a different pattern. For HTLV-II$_{Mo}$ isolate, digestion products had the following sizes: Rsa I (266 nt), Alu I (195 nt), Hinf I (127 nt) and Mbo I (60 nt). HTLV-II$_{NRA}$ and Italian IVDU proviral DNA were not susceptible to cleavage by Rsa I at base position 5883.

Both Mo and NRA-like isolates were found among US donors and IVDU. 5/8 US donors and 6/10 US IVDU resembled the HTLV-II$_{Mo}$ prototype. 3/8 US donors and 2/10 US IVDU were similar to the HTLV-II$_{NRA}$ prototype. No amplification of gp46 was seen with two of the US IVDU. Of 7 Italian IVDU tested, all looked like NRA type isolates by enzyme mapping of the 434 nt product generated by primers 85/86. All seven Italian IVDU differed from both Mo and NRA prototypes by showing the third distinct digestion pattern when the 539 nt amplified product from primers 82/88 was enzyme digested. Digestion with RsaI yielded a 91 nucleotide product in all cases.

Sequencing of PCR generated DNA fragments was then performed to assess nucleotide and amino acid variation among isolates. Sequence data for 320 bases from positions 5291 through 5610, a region including the Rsa I restriction site at position 5462, was determined for 2 US donors, 3 US IVDU and 4 Italian IVDU. In this region of the genome, the two control cell lines that were sequenced, HTLV-II$_{NRA}$ and HTLV-II$_{Mo}$ (729pH6neo), differed by 13/320 bases (4.1%).

HTLV-II isolates from two US IVDU and one US donor showed no identity at the 13 variant positions when compared to HTLV-II$_{NRA}$. No base substitutions were seen for these three isolates when compared to sequenced Mo control cell line 729pH6neo proviral DNA. Six other HTLV-II isolates, including one US donor, one US IVDU and 4 Italian IVDU, differed by 2/320 (0.6%) bases when compared to sequenced proviral DNA from the NRA cell line control. Identity with HTLV-II$_{NRA}$ at variant nucleotide positions was either 12/13 or 11/13. Base substitution occurred at nucleotide positions 5371 and 5446 for one US donor, 5446 and 5575 for one US IVDU, and at 5413 and 5446 for 4 Italian IVDU isolates. Only the HTLV-II$_{NRA}$ isolate had a base change at variant position 5446. For the Italian IVDU, substitution of a G at position 5413 introduced a new Rsa I enzyme digestion site, a finding consistent with the digestion pattern observed by restriction mapping. In contrast, Italian IVDU differed from HTLV-II$_{Mo}$ by 13/320 (4.1%) nucleotides. Accordingly, the Italian IVDU isolates were closer in sequence to the prototypic HTLV-II$_{NRA}$ isolate than to HTLV-II$_{Mo}$.

We claim:

1. An article of manufacture, comprising:

a container;

a label on said container; and composition contained within said container;

wherein the composition is effective for detecting anti-HTLV-II antibody, the label on said container indicates that the composition can be used for detecting anti-HTLV-II antibody, and the effective agent in said composition comprises HTLV-II antigen selected from the group consisting of SEQ ID NO 13, and SEQ ID NO 15, and combinations thereof.

2. The article of manufacture of claim 1 wherein said label on said container further indicates directions for in vitro use of said composition.

3. A kit, comprising:

a first container, a label on said container, and a composition contained within said container; wherein the composition is effective for detecting anti-HTLV-II antibody, the label on said container indicates that the composition can be used for detecting anti-HTLV-II antibody, and the effective agent in said composition comprises HTLV-II antigen selected from the group consisting of SEQ ID NO 13, and SEQ ID NO 15, and combinations thereof; and a second container comprising isotonic diluent.

4. The kit of claim 3 wherein said HTLV-II antigen is attached to a solid phase.

5. The kit of claim 3 further comprising HTLV-I antigen.

6. A method for detecting anti-HTLV-II antibody in a test sample, comprising the following steps:

a) providing
  (i) a test sample suspected of containing anti-HTLV-II antibody,
  (ii) HTLV-II antigen, said antigen comprising a composition selected from the group of HTLV-II$_{NRA}$ envelope peptides consisting of SEQ ID NO 13, SEQ ID NO 15, and combinations thereof;
  (iii) an indicator reagent comprising a detectable label and a binding member specific for said antigen or antibody; and
  (iv) an HTLV-I Envelope control reagent;

b) forming a reaction mixture by contacting the test sample with said antigen and indicator reagent;

c) incubating the reaction mixture under conditions sufficient to form antigen/antibody/indicator reagent complexes; and d) detecting the labeled complexes and comparing to said control reagent, wherein the presence of said labelled complexes act as an indication of the presence of anti-HTLV-II antibody in said test sample.

7. The method of claim 6 wherein said HTLV-II antigen is attached to a solid phase.

8. The method of claim 7 wherein said solid phase is selected from the group consisting of beads, microparticles and microtiter plate wells.

9. The method of claim 6 wherein said detectable label is selected from the group consisting of enzymes, radioisotopes, chemiluminescent and fluorescent labels.

10. The method of claim 6 where said indicator reagent binding member comprises anti-human IgG antibody.

11. A method for detecting anti-HTLV-II antibody in a test sample, comprising the following steps:

a) providing
  (i) a test sample suspected of containing anti-HTLV-II antibody,
  (ii) HTLV-II antigen, said antigen comprising a composition selected from the group consisting of HTLV-II$_{NRA}$ envelope peptides consisting of SEQ ID NO 13, SEQ ID No 15, and combinations thereof;
  (iii) an indicator reagent comprising a detectable label and a binding member specific for said antigen or antibody; and
  (iv) an HTLV-I Envelope control reagent;

b) forming a reaction mixture by contacting the test sample with said antigen;

c) incubating the reaction mixture under conditions sufficient to form antigen/antibody complexes;

d) after incubating, determining the presence or amount of anti-HTLV-II antibody by
  (i) contacting the reaction mixture with the indicator reagent;
  (ii) incubating the reaction mixture and the indicator reagent under conditions sufficient to form antigen/antibody/indicator reagent complexes; and
  (iii) detecting the labeled complexes or the reacted indicator reagent and comparing to said control reagent, wherein the presence of said labelled complexes or reacted indicator reagent act as an indication of the presence of anti-HTLV-I antibody in said test sample.

12. The method of claim 11 wherein said HTLV-II antigen is attached to a solid phase.

13. The method of claim 11 wherein said solid phase is selected from the group consisting of beads, microparticles and microtiter wells.

14. The method of claim 11 wherein said detectable label is selected from the group consisting of enzymes, radioisotopes, chemiluminescent and fluorescent labels.

15. A method for detecting antibody to HTLV-I and/or HTLV-II in a test sample, comprising:

a) providing a test sample suspected of containing HTLV-I antibody and/or HTLV-II antibody;

b) contacting said test sample with HTLV-I antigen and HTLV-II antigen for a time and under conditions sufficient to form antigen/antibody complexes, said HTLV-I antigen comprising a composition selected from the group consisting of HTLV-I viral lysates, HTLV-I peptides, HTLV-I proteins, and combinations thereof, and said HTLV-II antigen comprising a composition selected from the group HTLV-II$_{NRA}$ envelope peptides consisting of SEQ ID NO 13, SEQ ID NO 15, and combinations thereof;

c) contacting said complexes with indicator reagent comprising a detectable label and a binding member specific for said antigens or said antibodies under conditions sufficient to form antigen/antibody/indicator reagent complexes; and d) detecting the labeled complexes as an indication of anti-HTLV-I antibody, anti-HTLV-II antibody, or both, in said test sample.

16. The method of claim 15 wherein said HTLV-I antigen and HTLV-II antigen are attached to a solid phase.

17. The method of claim 16 wherein said HTLV-I antigen and HTLV-II antigen are attached to a single solid phase.

18. The method of claim 15 wherein said detectable label is selected from the group consisting of enzymes, radioisotopes, chemiluminescent and fluorescent labels.

19. The method of claim 15 wherein said indicator reagent binding member comprises an anti-human IgG antibody.

20. The method of claim 15 wherein steps (b) and (c) are performed simultaneously.

21. The method of claim 16 wherein said HTLV-I antigen and HTLV-II antigen are attached to separate solid phases.

22. The method of claim 21 wherein said indicator reagent binding member comprises HTLV-I antigen and HTLV-II antigen.

23. The method of claim 22 wherein said indicator reagent detectable label comprises biotin.

\* \* \* \* \*

UNITED STATES PATENT AND TRADEMARK OFFICE
CERTIFICATE OF CORRECTION

PATENT NO. : 6,406,841 B1
DATED : June 18, 2002
INVENTOR(S) : Helen H. Lee et al.

It is certified that error appears in the above-identified patent and that said Letters Patent is hereby corrected as shown below:

<u>Column 80,</u>
Line 32, replace "anti-HTLV-I" with -- anti-HTLV-II --.

Signed and Sealed this

Fifth Day of August, 2003

JAMES E. ROGAN
*Director of the United States Patent and Trademark Office*